United States Patent
Ford et al.

(10) Patent No.: US 6,472,173 B1
(45) Date of Patent: Oct. 29, 2002

(54) CHEMOKINE RECEPTOR OBTAINED FROM A CDNA LIBRARY OF FETAL LIVER-SPLEEN

(75) Inventors: John Ford, San Mateo, CA (US); George Yeung, Mountainview, CA (US)

(73) Assignee: Hyseq Inc, Sunnyvale, CA (US)

( * ) Notice: Subject to any disclaimer, the term of this patent is extended or adjusted under 35 U.S.C. 154(b) by 0 days.

(21) Appl. No.: 09/409,778

(22) Filed: Sep. 22, 1999

Related U.S. Application Data

(63) Continuation of application No. 09/236,166, filed on Jan. 22, 1999, now abandoned, which is a continuation of application No. 09/106,800, filed on Jun. 29, 1998, now abandoned.

(51) Int. Cl.[7] .................. C12N 15/12; C12N 15/63; C12N 5/00; C07H 21/04
(52) U.S. Cl. ............... 435/69.1; 435/320.1; 435/325; 536/23.5
(58) Field of Search ............ 536/23.5; 435/320.1, 435/325, 69.1

(56) References Cited

U.S. PATENT DOCUMENTS

| | | | |
|---|---|---|---|
| 5,440,021 A | 8/1995 | Chuntharapai et al. | 530/388.22 |
| 5,591,618 A | 1/1997 | Chantry et al. | 435/194 |
| 5,691,188 A | 11/1997 | Pausch et al. | 435/254.2 |
| 5,739,029 A | 4/1998 | King et al. | 435/254.21 |
| 5,744,324 A | 4/1998 | Lester et al. | 435/69.1 |
| 5,747,267 A | 5/1998 | Mulvihill et al. | 435/7.21 |
| 5,750,370 A | 5/1998 | Li et al. | 435/69.1 |

FOREIGN PATENT DOCUMENTS

| | | |
|---|---|---|
| EP | 0 899 332 | 3/1999 |
| WO | WO 94 12635 | 6/1994 |

OTHER PUBLICATIONS

Barritt, et al., "An Evaluation of Strategies Available for the Identification of GTP–Binding Proteins Required in Intracellular Signalling Pathways," Cell. Signal. 9:207–218 No. 3/4 (1997).
Carmerci, et al., "Identification of a gene (GPR30) with homology to the G–protein–coupled receptor superfamily associated with estrogen receptor expression in breast cancer," Genomics 45:607–617 (1997).
Chidiac, "Rethinking Receptor–G Protein–Effector Interactions," Biochemical Pharmacology 55:549–556 (1998).
Dohlmann, et al., "Model Systems for the Study of Seven–Transmembrane–Segment Receptors," Annu. Rev. Biochem. 60:653–88 (1991).
Feng, et al., "Cloning of a novel member of the G protein–coupled receptor family related to peptide receptors," Biochem. Biophys. Res. Commun. 231:651–654 (1997).

Grady, et al., "Turning off the signal: mechanisms that attenuate signaling by G protein–coupled receptors," Am. J. Physiol. 273:G586–601(1997).
Kvingedal, et al., "A novel putative G–protein–coupled receptor expressed in lung, heart and lymphoid tissue," FEBS Lett. 407:59–62 (1997).
Lefkowitz, R.J., "G Protein–Coupled Receptor Kinases," Cell 74:409–412 (1993).
Milligan, et al., "Biochemical Approaches to Examine the Specificity of Interactions Between Receptors and Guanine Nucleotide Binding Proteins," J. of Receptor & Signal Transduction Research 15:253–265 (1995).
O'Dowd, et al., "Discovery of three novel G–proteincoupled receptor genes, "Genomics 47:310–313 (1998).
Owman, et al., "Cloning and characterization of human cDNA encoding a novel heptahelix receptor derived from B cells and expressed in Burkitts lymphoma," Biochem. Biophys. Res. Commun. 228:285:292 (1996).
Power, et al., "Cloning and characterization of human chemokine receptors," Trends in Pharmacological Sciences, GB, Elsevier Trends Journal, 17:209–213 (1996).
Probst, et al., "Sequence Alignment of the G–Protein Coupled Receptor Superfamily," DNA and Cell Biology, 11:1–20 (1992).
International Search Report in PCT/US99/12829.
Smith, et al., "Contrasting Genetic Influence of CCR2 and CCR5 Variants on HIV–1 Infection and Disease Progression," Science 277:959–964 (1997).
Doerks et al. Protein annotation: detective work for function prediction. Trends in Genetics. Jun. 1998, vol. 14, No. 6, pp. 248–250.*
Mikayama T. Molecular cloning and functional expression of a cDNA encoding glycosylation–inhibiting factor. Proc. Natl. Acad. Sci. USA vol. 90, pp. 10056–10060, 1993.*
Voet et al. Biochemistry. 1990. John Wiley & Sons, Inc.. pp. 126–128 and 228–234.*
Bowie et al. Deciphering the Message in Protein Sequences: Tolerance to Amino Acid Substitutions. Science. vol. 247, pp. 1306–1310, 1990.*
Brenner et al. Errors in Genome Annotation. Trends in Genetics 1999, 15:132–133.*

* cited by examiner

Primary Examiner—David S. Romeo
Assistant Examiner—Joseph F. Murphy
(74) Attorney, Agent, or Firm—Marshall, Gerstein & Borun

(57) ABSTRACT

The invention provides novel polynucleotides isolated from cDNA libraries of human fetal liver-spleen and fetal liver as well as polypeptides encoded by these polynucleotides. The polypeptide is a human chemokine receptor that is a member of a family of G protein-coupled receptors characterized by seven transmembrane domains. Other aspects of the invention include vectors containing polynucleotides of the invention and related host cells as well a processes for producing chemokine receptor polypeptides, and antibodies specific for such polypeptides.

9 Claims, 5 Drawing Sheets

GTCATCATCTCGCGAGGGAAGCCCGGGGACGCACACTACCTGGGGCTACTGCA
CTTTGTGAAGGATTTCTCCAAACTCCTGGCCTTCTCCAGCAGCTTTGTGACAC
CACTTCTCTACCGCTACATGAACCAGAGCTTCCCCAGCAAGCTCCAACGGCTG
ATGAAAAAGCTGCCCTGCGGGGACCGGCACTGCTCCCCGGACCACATGGGGGT
GCAGCAGGTGCTGGCGTAGGCGGCCCAGCCCTCCTGGGGAGACGTGACTCTGG
TGGACGCAGAGCACTTAGTTACCCTGGACGCTCCC(SEQ ID NO: 1)

CGCAGGTCCTCACCAGAGCTCTGGTGGCCACCTCTGTCCCGCCATGCTGCTCA
CCGACAGTGGCCAGGGCCCACAGCACAAGAGGCTTGGGCCACAAAGTAAAGGG
TCTCGGAGCCTCACCGGCCGCCATGTGGAGCTGCAGCTGGTTCAACGGCACAR
GGCTGGTGGAGGAGCTGMCTGCCTGCCARGACCTGCAGCTGGGGCTGTCACTG
TTGTCGCTGCTGGGCCTGGTGGTGGGCGTGCCAGTGGGCCTGTGCTACAACGC
CCTGCTGGTGCTGGCCAACCTACACAGCAAGGCCAGCATGACCATGCCGGACG
TGTACTTTGTCAACATGGCAGTGGCAGGCCTGGTGCTCAGCGCCCTGGCCCCT
GTGCACCTGCTCGGCCCCCGAGCTCCCGGTGGGCGCTGTGGAGTGTGGGCGG
CGAAGTCCACGTGGCACTGCAGATCCCCTTCAATGTGTCCTCACTGGTGGCCA
TGTACTCCACCGCCCTGCTGAGCCTCGACCACTACATCGAGCGTGCACTGCCG
CGGACCTACATGGCCAGCGTGTACAACACGCGGCACGTGTGCGGCTTCGTGTG
GGGTGGCGCGCTGCTGACCAGCTTCTCCTCGCTGCTCTTCTACATCTGCAGCC
ATGTGTCCACCCGCGCGCTAGAGTGCGCCAAGATGCAGAACGCAGAAGCTGCC
GACGCCACGCTGGTGTTCATCGGCTACGTGGTGCCAGCACTGGCCACCCTCTA
CGCGCTGGTGCTACTCTCCCGCGTCCGCAGGGAGGACACGCCCCTGGACCGGG
ACACGGGCCGGCTGGAGCCCTCGGCACACAGGCTGCTGGTGGCCACCGTGTGC
ACGCAGTTTGGGCTCTGGACGCCACACTATCTGATCCTGCTGGGGCACACGGT
CATCATCTCGCGAGGGAAGCCCGTGGACGCACACTACCTGGGGCTACTGCACT
TTGTGAAGGATTTCTCCAAACTCCTGGCCTTCTCCAGCAGCTTTGTGACACCA
CTTCTCTACCGCTACATGAACCAGAGCTTCCCCAGCAAGCTCCAACGGCTGAT
GAAAAAGCTGCCCTGCGGGGACCGGCACTGCTCCCCGGACCACATGGGGGTGC
AGCAGGTGCTGGCGTAGGCGGCCCAGCCCTCCTGGGGAGACGTGACTCTGGTG
GACGCAGAGCACTTAGTTACCCTGGACGCTCCCCACATCCTTCCAGAAGGAGA
CGAGCTGCTGGAAGAGAAGCAGGAGGGGTGTTTTTCTTGAAGTTTCCTTTTTC
CCACAAATGCCACTCTTGGGCCAAGGCTGTGGTCCCCGTGGCTGGCATCTGGC
TTGAGTCTCCCCGAGGCCTGTGCGTCTCCAAACACGCAGCTCAAGGTCCACA
TCTGCAAAAGCCTCCTCGCCTTCAGCCTCCTCAGCATTCAGTTTGTCAATGAA
GTGATGAAAGCTTARAGCCAGTATTTATACTTTGTGGTTAAAATACTTGATTC
CCCCTTGTTTATTTTACAAAAACAGATGTTTCCTAGAAAAATGACAAATAGTA
AAATGAACAAAACCCTACGAAAGAATGGCAACAGCCAGGGTGGCGGCCCTGCA
GTGGGCGGCGTGTGCTACAAGGCC (SEQ ID NO: 2)

FIG. 1

MWSCSWFNGTXLVEELXACXDLQLGLSLLSLLGLVVGVPVGLCYNALLVLANLHSKASMTMPDV
YFVNMAVAGLVLSALAPVHLLGPPSSRWALWSVGGEVHVALQIPFNVSSLVAMYSTALLSLDHY
IERALPRTYMASVYNTRHVCGFVWGGALLTSFSSLLFYICSHVSTRALECAKMQNAEAADATLV
FIGYVVPALATLYALVLLSRVRREDTPLDRDTGRLEPSAHRLLVATVCTQFGLWTPHYLILLGH
TVIISRGKPVDAHYLGLLHFVKDFSKLLAFSSSFVTPLLYRYMNQSFPSKLQRLMKKLPCGDRH
CSPDHMGVQQVLA (SEQ ID NO: 3)

FIG. 2

```
1   M----WSCSWFNGTXLVEELXA---------------CQ    SEQ ID NO: 3
1   MEDFNMESDSFEDFWKGEDLSNYSYSSTLPPFLLDAAPCE   IL-8 RII.seq 21  DLQLGLS-----------LLSLLGLVVGVPVGLCYNALL    SEQ ID NO: 3
41  PESLEINKYFVVIIYALVFLLSLLG----------NSLV    IL-8 RII.seq 49  VLANLHSKASMTMPDVYFVNMAVAGLVLSALAPVHLLGPP   SEQ ID NO: 3
70  MLVILYSRVGRSVTDVYLLNLALADLLFALTLPI------   IL-8 RII.seq 89  SSRWALWSVGG-------EVHVALQIPFNVSSLVAMYST    SEQ ID NO: 3
104 ---WAASKVNGWIFGTFLCKVSLLKE------VNFYSG    IL-8 RII.seq 121 ALL----SLDHYIERA-LPRTYMASVYNTRHVCGFVWGGA   SEQ ID NO: 3
134 ILLLACISVDRYLAIVHATRTLTQKRYLVKFICLSIWGLS   IL-8 RII.seq 156 LLTSFSSLLFYICSHVSTRALECAKMQNAEAAD-ATLVFI   SEQ ID NO: 3
174 LLLALPVLLFRRTVYSSNVSPACYEDMGNNTANWRMLLRI   IL-8 RII.seq 195 -----GYVVPALATLY----ALVLLSRVRREDTPLDRDTG   SEQ ID NO: 3
214 LPQSFGFIVPLLIMLFCYGFTLRTLFKAHMGQKH------   IL-8 RII.seq 226 RLEPSAHRLLVATVCTQFGL-WTPHYLILLGHTVIISR--   SEQ ID NO: 3
248 ----RAMRVIFAVV-LIFLLCWLPYNLVLLADTLMRTQVI   IL-8 RII.seq 263 ----------GKPVDAHYLGLLHFVKDFSKLLAFSSSFVT   SEQ ID NO:3
283 QETCERRNHIDRAILDA-------------TEILGILHSCLN   IL-8 RII.seq 293 PLLYRYMNQSFPSKLQRLMK-------KLPCGDRHCSPD    SEQ ID NO: 3
311 PLIYAFIGQKFRHGLLKILAIHGLISKDSLPKDSRPSFVG   IL-8 RII.seq 325 HMGVQQVLA                                  SEQ ID NO: 3
351 SSSGHTSTTL                                 IL-8 RII.seq
```

DECORATION 'DECORATION #1': BOX RESIDUES THAT MATCH SEQ ID NO: 3 EXACTLY.

FIG. 3

SEQ ID NO 3
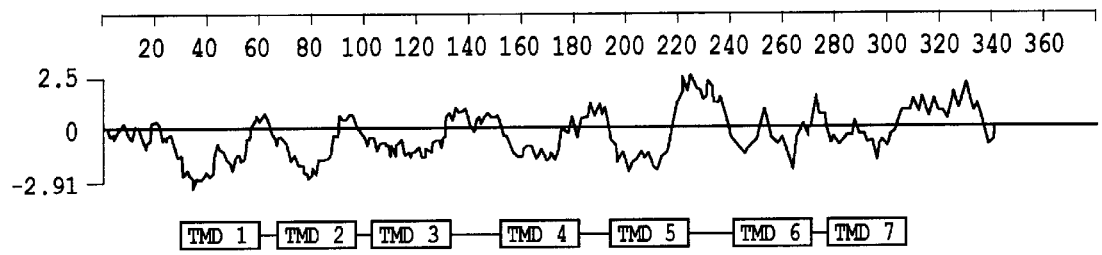
INTERLEUKIN-8 RECEPTOR TYPE II
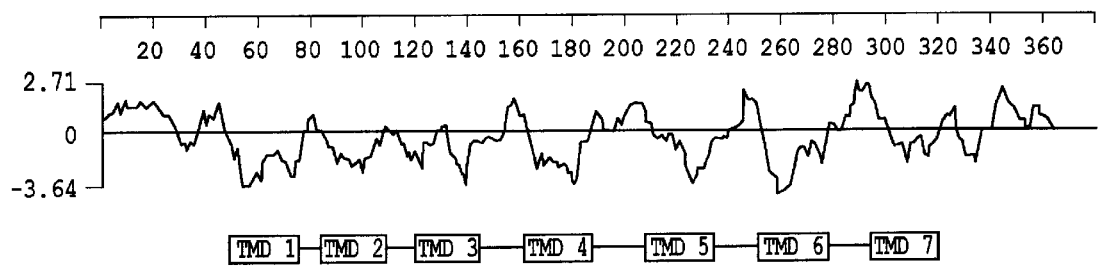
FIGURE X: ALIGNMENT OF THE TRANSMEMBRANE DOMAINS BETWEEN SEQ ID NO 3 AND INTERLEUKIN-8 RECEPTOR TYPE II BASED ON THE HYDROPHILICITY PROFILE USING THE KYTE-DOOLITTLE METHOD. THE ASSIGNMENT OF THE TRANSMEMBRANE DOMAINS IN INTERLEUKIN-8 RECEPTOR IS DERIVED FROM GENEBANK ANNOTATIONS.
FIG. 4

SEQ ID NO: 5                    123 LSLDHYIER 131
                                    +S+D Y+
SEQ ID NO: 6 (IL-8 RECEPTOR)    140 ISVDRYLAI 148

FIG. 5

SEQ ID NO: 7
PHOSPHORYLATION SITES ON IL-8 RECEPTOR TYPE II    349 VGSSSGHT 356

SEQ ID NO: 8
POTENTIAL PHOSPHORYLATION SITES ON SEQ ID NO: 3   285 AFSSSFVT 292

FIG. 6

```
                         SEQUENCE LISTING

<160> NUMBER OF SEQ ID NOS:  25

<210> SEQ ID NO 1
<211> LENGTH: 300
<212> TYPE: DNA
<213> ORGANISM: Homo sapiens

<400> SEQUENCE: 1
gtcatcatct cgcgagggaa gcccggggac gcacactacc tggggctact gcactttgtg       60
aaggatttct ccaaactcct ggccttctcc agcagctttg tgacaccact tctctaccgc      120
tacatgaacc agagcttccc cagcaagctc caacggctga tgaaaaagct gccctgcggg      180
gaccggcact gctccccgga ccacatgggg gtgcagcagg tgctggcgta ggcggcccag      240
ccctcctggg gagacgtgac tctggtggac gcagagcact tagttaccct ggacgctccc      300

<210> SEQ ID NO 2
<211> LENGTH: 1614
<212> TYPE: DNA
<213> ORGANISM: Homo sapiens
<220> FEATURE:
<221> NAME/KEY: CDS
<222> LOCATION: (129)...(1127)

<400> SEQUENCE: 2
cgcaggtcct caccagagct ctggtggcca cctctgtccc gccatgctgc tcaccgacag       60
tggccagggc ccacagcaca agaggcttgg gccacaaagt aaagggtctc ggagcctcac      120 cggccgcc atg tgg agc tgc agc tgg ttc aac ggc aca rgg ctg gtg gag      170
         Met Trp Ser Cys Ser Trp Phe Asn Gly Thr Xaa Leu Val Glu
          1               5                  10 gag ctg mct gcc tgc car gac ctg cag ctg ggg ctg tca ctg ttg tcg      218
Glu Leu Xaa Ala Cys Xaa Asp Leu Gln Leu Gly Leu Ser Leu Leu Ser
 15                  20                  25                  30 ctg ctg ggc ctg gtg gtg ggc gtg cca gtg ggc ctg tgc tac aac gcc      266
Leu Leu Gly Leu Val Val Gly Val Pro Val Gly Leu Cys Tyr Asn Ala
                 35                  40                  45 ctg ctg gtg ctg gcc aac cta cac agc aag gcc agc atg acc atg ccg      314
Leu Leu Val Leu Ala Asn Leu His Ser Lys Ala Ser Met Thr Met Pro
             50                  55                  60 gac gtg tac ttt gtc aac atg gca gtg gca ggc ctg gtg ctc agc gcc      362
Asp Val Tyr Phe Val Asn Met Ala Val Ala Gly Leu Val Leu Ser Ala
         65                  70                  75
```

```
ctg gcc cct gtg cac ctg ctc ggc ccc ccg agc tcc cgg tgg gcg ctg        410
Leu Ala Pro Val His Leu Leu Gly Pro Pro Ser Ser Arg Trp Ala Leu
     80              85                  90 tgg agt gtg ggc ggc gaa gtc cac gtg gca ctg cag atc ccc ttc aat        458
Trp Ser Val Gly Gly Glu Val His Val Ala Leu Gln Ile Pro Phe Asn
 95             100                 105                 110 gtg tcc tca ctg gtg gcc atg tac tcc acc gcc ctg ctg agc ctc gac        506
Val Ser Ser Leu Val Ala Met Tyr Ser Thr Ala Leu Leu Ser Leu Asp
                115                 120                 125 cac tac atc gag cgt gca ctg ccg cgg acc tac atg gcc agc gtg tac        554
His Tyr Ile Glu Arg Ala Leu Pro Arg Thr Tyr Met Ala Ser Val Tyr
        130                 135                 140 aac acg cgg cac gtg tgc ggc ttc gtg tgg ggt ggc gcg ctg ctg acc        602
Asn Thr Arg His Val Cys Gly Phe Val Trp Gly Gly Ala Leu Leu Thr
            145                 150                 155 agc ttc tcc tcg ctg ctc ttc tac atc tgc agc cat gtg tcc acc cgc        650
Ser Phe Ser Ser Leu Leu Phe Tyr Ile Cys Ser His Val Ser Thr Arg
160                 165                 170 gcg cta gag tgc gcc aag atg cag aac gca gaa gct gcc gac gcc acg        698
Ala Leu Glu Cys Ala Lys Met Gln Asn Ala Glu Ala Ala Asp Ala Thr
175                 180                 185                 190 ctg gtg ttc atc ggc tac gtg gtg cca gca ctg gcc acc ctc tac gcg        746
Leu Val Phe Ile Gly Tyr Val Val Pro Ala Leu Ala Thr Leu Tyr Ala
                195                 200                 205 ctg gtg cta ctc tcc cgc gtc cgc agg gag gac acg ccc ctg gac cgg        794
Leu Val Leu Leu Ser Arg Val Arg Arg Glu Asp Thr Pro Leu Asp Arg
            210                 215                 220 gac acg ggc cgg ctg gag ccc tcg gca cac agg ctg ctg gtg gcc acc        842
Asp Thr Gly Arg Leu Glu Pro Ser Ala His Arg Leu Leu Val Ala Thr
        225                 230                 235 gtg tgc acg cag ttt ggg ctc tgg acg cca cac tat ctg atc ctg ctg        890
Val Cys Thr Gln Phe Gly Leu Trp Thr Pro His Tyr Leu Ile Leu Leu
    240                 245                 250 ggg cac acg gtc atc atc tcg cga ggg aag ccc gtg gac gca cac tac        938
Gly His Thr Val Ile Ile Ser Arg Gly Lys Pro Val Asp Ala His Tyr
255                 260                 265                 270 ctg ggg cta ctg cac ttt gtg aag gat ttc tcc aaa ctc ctg gcc ttc        986
Leu Gly Leu Leu His Phe Val Lys Asp Phe Ser Lys Leu Leu Ala Phe
                275                 280                 285 tcc agc agc ttt gtg aca cca ctt ctc tac cgc tac atg aac cag agc       1034
Ser Ser Ser Phe Val Thr Pro Leu Leu Tyr Arg Tyr Met Asn Gln Ser
            290                 295                 300 ttc ccc agc aag ctc caa cgg ctg atg aaa aag ctg ccc tgc ggg gac       1082
Phe Pro Ser Lys Leu Gln Arg Leu Met Lys Lys Leu Pro Cys Gly Asp
        305                 310                 315 cgg cac tgc tcc ccg gac cac atg ggg gtg cag cag gtg ctg gcg            1127
Arg His Cys Ser Pro Asp His Met Gly Val Gln Gln Val Leu Ala
    320                 325                 330 taggcggccc agccctcctg gggagacgtg actctggtgg acgcagagca cttagttacc     1187
ctggacgctc cccacatcct tccagaagga gacgagctgc tggaagagaa gcaggagggg     1247 tgttttctt gaagtttcct ttttcccaca atgccactc ttgggccaag gctgtggtcc       1307
ccgtggctgg catctggctt gagtctcccc gaggcctgtg cgtctcccaa acacgcagct    1367
caaggtccac atctgcaaaa gcctcctcgc cttcagcctc ctcagcattc agtttgtcaa    1427
tgaagtgatg aaagcttara gccagtattt atactttgtg gttaaaatac ttgattcccc    1487
cttgtttatt ttcaaaaaac agatgttttcc tagaaaaatg acaaatagta aaatgaacaa   1547
```
aaccctacga aagaatggca acagccaggg tggcggccct gcagtgggcg gcgtgtgcta 1607 caaggcc 1614

<210> SEQ ID NO 3
<211> LENGTH: 333
<212> TYPE: PRT
<213> ORGANISM: Homo sapiens
<220> FEATURE:
<221> NAME/KEY: VARIANT
<222> LOCATION: (1)...(333)
<223> OTHER INFORMATION: Xaa = Any Amino Acid

<400> SEQUENCE: 3

```
Met Trp Ser Cys Ser Trp Phe Asn Gly Thr Xaa Leu Val Glu Glu Leu
 1               5                  10                  15

Xaa Ala Cys Xaa Asp Leu Gln Leu Gly Leu Ser Leu Leu Ser Leu Leu
            20                  25                  30

Gly Leu Val Val Gly Val Pro Gly Leu Cys Tyr Asn Ala Leu Leu
        35                  40                  45

Val Leu Ala Asn Leu His Ser Lys Ala Ser Met Thr Met Pro Asp Val
    50                  55                  60

Tyr Phe Val Asn Met Ala Val Ala Gly Leu Val Leu Ser Ala Leu Ala
65                  70                  75                  80

Pro Val His Leu Leu Gly Pro Pro Ser Ser Arg Trp Ala Leu Trp Ser
                85                  90                  95

Val Gly Gly Glu Val His Val Ala Leu Gln Ile Pro Phe Asn Val Ser
            100                 105                 110

Ser Leu Val Ala Met Tyr Ser Thr Ala Leu Leu Ser Leu Asp His Tyr
        115                 120                 125

Ile Glu Arg Ala Leu Pro Arg Thr Tyr Met Ala Ser Val Tyr Asn Thr
    130                 135                 140

Arg His Val Cys Gly Phe Val Trp Gly Gly Ala Leu Leu Thr Ser Phe
145                 150                 155                 160

Ser Ser Leu Leu Phe Tyr Ile Cys Ser His Val Ser Thr Arg Ala Leu
                165                 170                 175

Glu Cys Ala Lys Met Gln Asn Ala Glu Ala Ala Asp Ala Thr Leu Val
            180                 185                 190

Phe Ile Gly Tyr Val Val Pro Ala Leu Ala Thr Leu Tyr Ala Leu Val
        195                 200                 205

Leu Leu Ser Arg Val Arg Arg Glu Asp Thr Pro Leu Asp Arg Asp Thr
    210                 215                 220

Gly Arg Leu Glu Pro Ser Ala His Arg Leu Leu Val Ala Thr Val Cys
225                 230                 235                 240

Thr Gln Phe Gly Leu Trp Thr Pro His Tyr Leu Ile Leu Leu Gly His
                245                 250                 255

Thr Val Ile Ile Ser Arg Gly Lys Pro Val Asp Ala His Tyr Leu Gly
            260                 265                 270

Leu Leu His Phe Val Lys Asp Phe Ser Lys Leu Leu Ala Phe Ser Ser
        275                 280                 285

Ser Phe Val Thr Pro Leu Leu Tyr Arg Tyr Met Asn Gln Ser Phe Pro
    290                 295                 300

Ser Lys Leu Gln Arg Leu Met Lys Lys Leu Pro Cys Gly Asp Arg His
305                 310                 315                 320

Cys Ser Pro Asp His Met Gly Val Gln Gln Val Leu Ala
                325                 330
```

```
<210> SEQ ID NO 4
<211> LENGTH: 360
<212> TYPE: PRT
<213> ORGANISM: Homo sapiens

<400> SEQUENCE: 4

Met Glu Asp Phe Asn Met Glu Ser Asp Ser Phe Glu Asp Phe Trp Lys
 1               5                   10                  15

Gly Glu Asp Leu Ser Asn Tyr Ser Tyr Ser Ser Thr Leu Pro Pro Phe
                20                  25                  30

Leu Leu Asp Ala Ala Pro Cys Glu Pro Glu Ser Leu Glu Ile Asn Lys
            35                  40                  45

Tyr Phe Val Val Ile Ile Tyr Ala Leu Val Phe Leu Leu Ser Leu Leu
50                  55                  60

Gly Asn Ser Leu Val Met Leu Val Ile Leu Tyr Ser Arg Val Gly Arg
65                  70                  75                  80

Ser Val Thr Asp Val Tyr Leu Leu Asn Leu Ala Leu Ala Asp Leu Leu
                85                  90                  95

Phe Ala Leu Thr Leu Pro Ile Trp Ala Ala Ser Lys Val Asn Gly Trp
            100                 105                 110

Ile Phe Gly Thr Phe Leu Cys Lys Val Val Ser Leu Leu Lys Glu Val
        115                 120                 125

Asn Phe Tyr Ser Gly Ile Leu Leu Leu Ala Cys Ile Ser Val Asp Arg
130                 135                 140

Tyr Leu Ala Ile Val His Ala Thr Arg Thr Leu Thr Gln Lys Arg Tyr
145                 150                 155                 160

Leu Val Lys Phe Ile Cys Leu Ser Ile Trp Gly Leu Ser Leu Leu Leu
                165                 170                 175

Ala Leu Pro Val Leu Leu Phe Arg Arg Thr Val Tyr Ser Ser Asn Val
            180                 185                 190

Ser Pro Ala Cys Tyr Glu Asp Met Gly Asn Asn Thr Ala Asn Trp Arg
        195                 200                 205

Met Leu Leu Arg Ile Leu Pro Gln Ser Phe Gly Phe Ile Val Pro Leu
210                 215                 220

Leu Ile Met Leu Phe Cys Tyr Gly Phe Thr Leu Arg Thr Leu Phe Lys
225                 230                 235                 240

Ala His Met Gly Gln Lys His Arg Ala Met Arg Val Ile Phe Ala Val
                245                 250                 255

Val Leu Ile Phe Leu Leu Cys Trp Leu Pro Tyr Asn Leu Val Leu Leu
            260                 265                 270

Ala Asp Thr Leu Met Arg Thr Gln Val Ile Gln Glu Thr Cys Glu Arg
        275                 280                 285

Arg Asn His Ile Asp Arg Ala Leu Asp Ala Thr Glu Ile Leu Gly Ile
290                 295                 300

Leu His Ser Cys Leu Asn Pro Leu Ile Tyr Ala Phe Ile Gly Gln Lys
305                 310                 315                 320

Phe Arg His Gly Leu Leu Lys Ile Leu Ala Ile His Gly Leu Ile Ser
                325                 330                 335

Lys Asp Ser Leu Pro Lys Asp Ser Arg Pro Ser Phe Val Gly Ser Ser
            340                 345                 350

Ser Gly His Thr Ser Thr Thr Leu
        355                 360

<210> SEQ ID NO 5
```

```
<211> LENGTH: 9
<212> TYPE: PRT
<213> ORGANISM: Homo sapiens

<400> SEQUENCE: 5

Leu Ser Leu Asp His Tyr Ile Glu Arg
 1               5

<210> SEQ ID NO 6
<211> LENGTH: 9
<212> TYPE: PRT
<213> ORGANISM: Homo sapiens

<400> SEQUENCE: 6

Ile Ser Val Asp Arg Tyr Leu Ala Ile
 1               5

<210> SEQ ID NO 7
<211> LENGTH: 8
<212> TYPE: PRT
<213> ORGANISM: Homo sapiens

<400> SEQUENCE: 7

Val Gly Ser Ser Ser Gly His Thr
 1               5

<210> SEQ ID NO 8
<211> LENGTH: 8
<212> TYPE: PRT
<213> ORGANISM: Homo sapiens

<400> SEQUENCE: 8

Ala Phe Ser Ser Ser Phe Val Thr
 1               5

<210> SEQ ID NO 9
<211> LENGTH: 15
<212> TYPE: DNA
<213> ORGANISM: Artificial Sequence
<220> FEATURE:
<223> OTHER INFORMATION: Exemplary oligonucleotide primer used in
      sequence assembly process
<221> NAME/KEY: misc_feature
<222> LOCATION: (8)...(8)
<223> OTHER INFORMATION: n = A, T, C, G or 1-(2-deoxy-D-ribfuranosyl)-
      3-nitropyrrole

<400> SEQUENCE: 9 ccttttttntt tttgg                                              15

<210> SEQ ID NO 10
<211> LENGTH: 15
<212> TYPE: DNA
<213> ORGANISM: Artificial Sequence
<220> FEATURE:
<223> OTHER INFORMATION: Exemplary oligonucleotide primer used in
      sequence assembly process
<221> NAME/KEY: misc_feature
<222> LOCATION: (8)...(8)
<223> OTHER INFORMATION: n = A, T, C, G or 1-(2-deoxy-D-ribfuranosyl)-
      3-nitropyrrole

<400> SEQUENCE: 10
ccaaaaanaa aaagg                                               15

<210> SEQ ID NO 11
<211> LENGTH: 12
```

```
<212> TYPE: DNA
<213> ORGANISM: Artificial Sequence
<220> FEATURE:
<223> OTHER INFORMATION: Exemplary nucleotide hybridization sequence
      used in sequence assembly process

<400> SEQUENCE: 11
aaaaaatttt tt                                                         12

<210> SEQ ID NO 12
<211> LENGTH: 12
<212> TYPE: DNA
<213> ORGANISM: Artificial Sequence
<220> FEATURE:
<223> OTHER INFORMATION: Exemplary nucleotide hybridization sequence
      used in sequence assembly process

<400> SEQUENCE: 12
aaaaattttt ta                                                         12

<210> SEQ ID NO 13
<211> LENGTH: 11
<212> TYPE: DNA
<213> ORGANISM: Artificial Sequence
<220> FEATURE:
<223> OTHER INFORMATION: Exemplary nucleotide hybridization sequence
      used in sequence assembly process

<400> SEQUENCE: 13 aaaaatttttt t                                                         11

<210> SEQ ID NO 14
<211> LENGTH: 12
<212> TYPE: DNA
<213> ORGANISM: Artificial Sequence
<220> FEATURE:
<223> OTHER INFORMATION: Exemplary nucleotide hybridization sequence
      used in sequence assembly process

<400> SEQUENCE: 14
aaaaattttt tc                                                         12

<210> SEQ ID NO 15
<211> LENGTH: 12
<212> TYPE: DNA
<213> ORGANISM: Artificial Sequence
<220> FEATURE:
<223> OTHER INFORMATION: Exemplary nucleotide hybridization sequence
      used in sequence assembly process

<400> SEQUENCE: 15
aaaaattttt tg                                                         12

<210> SEQ ID NO 16
<211> LENGTH: 12
<212> TYPE: DNA
<213> ORGANISM: Artificial Sequence
<220> FEATURE:
<223> OTHER INFORMATION: Exemplary nucleotide hybridization sequence
      used in sequence assembly process

<400> SEQUENCE: 16
taaaaatttt tt                                                         12

<210> SEQ ID NO 17
<211> LENGTH: 12
<212> TYPE: DNA
```

```
<213> ORGANISM: Artificial Sequence
<220> FEATURE:
<223> OTHER INFORMATION: Exemplary nucleotide hybridization sequence
      used in sequence assembly process

<400> SEQUENCE: 17
caaaaatttt tt                                                              12

<210> SEQ ID NO 18
<211> LENGTH: 12
<212> TYPE: DNA
<213> ORGANISM: Artificial Sequence
<220> FEATURE:
<223> OTHER INFORMATION: Exemplary nucleotide hybridization sequence
      used in sequence assembly process

<400> SEQUENCE: 18
gaaaaatttt tt                                                              12

<210> SEQ ID NO 19
<211> LENGTH: 11
<212> TYPE: DNA
<213> ORGANISM: Artificial Sequence
<220> FEATURE:
<223> OTHER INFORMATION: Exemplary nucleotide hybridization sequence
      used in sequence assembly process

<400> SEQUENCE: 19
aaaaaatttt t                                                               11

<210> SEQ ID NO 20
<211> LENGTH: 21
<212> TYPE: DNA
<213> ORGANISM: Artificial Sequence
<220> FEATURE:
<223> OTHER INFORMATION: Exemplary oligonucleotide primer used in
      sequence assembly process

<400> SEQUENCE: 20
cagcaggtgc tggcgtaggc g                                                    21

<210> SEQ ID NO 21
<211> LENGTH: 21
<212> TYPE: DNA
<213> ORGANISM: Artificial Sequence
<220> FEATURE:
<223> OTHER INFORMATION: Exemplary oligonucleotide primer used in
      sequence assembly process

<400> SEQUENCE: 21
gactctggtg gagcgagagc a                                                    21

<210> SEQ ID NO 22
<211> LENGTH: 21
<212> TYPE: DNA
<213> ORGANISM: Artificial Sequence
<220> FEATURE:
<223> OTHER INFORMATION: Exemplary oligonucleotide primer used in
      sequence assembly process

<400> SEQUENCE: 22
ggggagacgt gactctggtg g                                                    21

<210> SEQ ID NO 23
<211> LENGTH: 21
<212> TYPE: DNA
<213> ORGANISM: Artificial Sequence
```

-continued

```
<220> FEATURE:
<223> OTHER INFORMATION: Exemplary oligonucleotide primer used in
      sequence assembly process

<400> SEQUENCE: 23
accttgagct gcgtgtttgg g                                          21

<210> SEQ ID NO 24
<211> LENGTH: 25
<212> TYPE: DNA
<213> ORGANISM: Artificial Sequence
<220> FEATURE:
<223> OTHER INFORMATION: Exemplary oligonucleotide primer used in
      sequence assembly process

<400> SEQUENCE: 24
atgaattcta atacgactca ctata                                      25

<210> SEQ ID NO 25
<211> LENGTH: 21
<212> TYPE: DNA
<213> ORGANISM: Artificial Sequence
<220> FEATURE:
<223> OTHER INFORMATION: Exemplary oligonucleotide primer used in
      sequence assembly process

<400> SEQUENCE: 25
cgcctacgcc agcacctgct g                                          21
```

CHEMOKINE RECEPTOR OBTAINED FROM A CDNA LIBRARY OF FETAL LIVER-SPLEEN

RELATED APPLICATIONS

This patent application is a continuation of U.S. patent application Ser. No. 09/236,166 filed Jan. 22, 1999, now abandonded, which is a continuation of U.S. patent application Ser. No. 09/106,800 filed Jun. 29, 1998, now abandoned, both of which are incorporated by reference herein in their entirety.

1. FIELD OF THE INVENTION

This invention relates in general to novel polynucleotides isolated from cDNA libraries of human fetal liver-spleen and fetal liver and to polypeptides encoded by these polynucleotides. In particular, the invention relates to a human chemokine receptor that is a member of a family of G protein-coupled receptors characterized by seven transmembrane domains.

2. BACKGROUND

It is well established that many medically significant biological processes are mediated by proteins participating in signal transduction pathways that involve GTP-binding proteins (termed "G proteins") and/or second messengers, e.g., cAMP (Lefkowitz, Nature, 351:353–354 (1991)). Examples include "G protein-coupled receptors," such as rhodopsin and the receptors for the adrenergic ligands and dopamine (Kobilka, B. K., et al., PNAS 84:46–50 (1987); Kobilka, B. K., et al., Science 238:650–656 (1987); Bunzow, J. R. et al., Nature 336:783–787 (1988)); G proteins themselves; effector proteins, e.g., phospholipase C, adenylyl cyclase, and phosphodiesterase; and actuator proteins, e.g., protein kinase A and protein kinase C (Simon, M. I., et al., Science, 252:802–8 (1991)).

In the inactive state, the membrane-associated G protein is a heterotrimer of alpha, beta, and gamma subunits in which the alpha subunit is bound to GDP. The binding of a ligand to a G protein-coupled receptor stimulates a receptor-G protein interaction that results in the exchange of GDP for GTP on the alpha subunit. The alpha subunit then dissociates from the beta-gamma subunits and interacts with an effector. In the case of epinephrine, for example, a G protein couples the beta-adrenergic receptor to adenylyl cyclase, stimulating the production of cAMP. The resultant rise in cAMP levels activates the cAMP-dependent protein kinase A, which phosphorylates and activates glycogen phosphorylase kinase. The latter, in turn, phosphorylates glycogen phosphorylase, producing a characteristic hormone-stimulated increase in enzymatic activity. Hydrolysis of GTP to GDP, catalyzed by the G protein itself, returns the G protein to its basal, inactive form. Thus, the G protein serves a dual role in signal transduction, namely, as an intermediate that relays the signal from receptor to effector, and as a clock that controls the duration of the signal.

G protein-coupled receptors mediate the actions of a wide variety of extracellular signals including light, odorants, peptide hormones, and neurotransmitters and have been identified in organisms as evolutionarily divergent as yeast and humans. (See generally, Dolman et al., Ann. Rev. Biochem. 60:653–699 (1991).) Many G protein-coupled receptors share a similar topological motif consisting of seven hydrophobic (and potentially alpha-helical) regions predicted to span the lipid bilayer. Indeed, the transmembrane domains of such receptors are generally the most highly conserved regions of the proteins. Structure-function analyses carried out on the $\alpha_2$-, $\beta_1$-, and $\beta_2$-adrenergic receptors have shown that the fourth transmembrane segment (TMS IV) contains domains that contribute to the binding selectivity of various agonists and antagonists. TMS VII was shown modulate binding to receptor antagonists. Domains responsible for G protein binding are found the region of the protein encompassing TMS V and TMS VI along with the connecting cytoplasmic loop. These studies also implicate the cytoplasmic loops near TMS's V–VII as determinants of G protein coupling and specificity.

Many 7-TMS receptors include a number of conserved cysteine residues. In both rhodopsin and the $\beta_2$-adrenergic receptor, cysteines located in the C-terminal domain distal to TMS VII are covalently modified by palmitoylation. The $\beta_2$-adrenergic receptor has been shown to contain two disulfide bonds that are required for normal ligand binding. Site-directed mutagenesis has revealed that four cysteines are essential for proper cell surface expression and ligand binding. Similar studies of rhodopsin indicate that, as in the $\beta_2$-adrenergic receptor, a disulfide bond in a hydrophilic loop is critical for directing and/or stabilizing interactions that form the ligand binding domain. By contrast, the yeast $\alpha$-factor receptor has only two cysteine residues, both of which may be replaced by site-directed mutagenesis without any adverse effect on receptor function.

7-TMS receptors also share the ability to become desensitized, a process by which the receptors become refractory to further stimulation after an initial response, despite the continued presence of the original stimulus. Desensitization results from a reduction in the number of cell surface receptors or from an attenuation of the interaction between the receptor and the G protein (i.e., receptor-G protein "uncoupling"). Many G protein-coupled receptors of the seven-transmembrane-segment class (hereafter "7-TMS receptors") are rapidly uncoupled after exposure to agonists, a process regulated, at least in part, by phosphorylation.

The 7-TMS receptor family includes receptors for members of the chemokine family of inflammatory cytokines, such as interleukin-8 (hereafter IL-8). The name "chemokine" is derived from the ability of these proteins to stimulate chemotaxis of leukocytes. Indeed, chemokines comprise the main attractants for inflammatory cells during inflammatory and immune responses. See generally, Baggiolini et al., Advances in Immunology, 55:97–179 (1994). Chemokines have been shown to recruit a wide range of leukocytes to sites of infection, inflammation, and disease. For example, chemokines have been shown to be directly involved in the inflammatory process associated with conditions such as allergies (J Clin Invest Oct. 1, 1997; 100(7):1657–1666 Teixeira MM et al.), asthma (J Immunol Nov. 1, 1997;159 (9):4593–4601 Lamkhioued B, et al.), arthritis (J Exp Med Jul. 7, 1997;186(1):131–137 Gong J H et al.), gastric inflammation (Physiol Pharmacol September 1997; 48 (3):405–413 Watanabe N et al.), injury (Eur J Neurosci Jul. 9, 1997;9(7): 1422–1438 Bartholdi D, Schwab M E), transplantation rejection (Transplantation Jun. 27, 1997;63(12) :1807–1812 Fairchild R L et al.) and autoimmune disorders (J Neuroimmunol July 1997;77(1):17–26 Miyagishi R et al).

Members of the chemokine family generally exhibit 20–70% amino acid identity to one another and contain several highly-conserved cysteine residues. Chemokines can be classified into various subclasses or subfamilies by virtue of the position and spacing of a set of conserved cysteines, designated C-X-C (e.g., IL-8), C-C (e.g., RANTES) and C (e.g., lymphotactin). The C-X-C subfamily has the first two conserved cysteines separated by one amino acid, and the genes encoding the C-X-C subfamily are predominantly located on human chromosome 4. The C-C subfamily has two adjacent cysteines, and the genes encoding the C-C subfamily are predominantly located on human chromosome 17. The C subfamily has one of the first two conserved cysteines, and the genes encoding the C subfamily are predominantly located on human chromosome 17.

C-X-C chemokines IL-8, GROα, GROβ, GROγ, ENA-78, NAP-2, PF4, and γIP10 form a subfamily of neutrophil chemoattractants. IL-8, GROα, and NAP-2 have been shown to compete for similar binding sites on neutrophils and elicit similar biological effects. At least two IL-8 receptors have been characterized, and their genes have been mapped to chromosome 2q34–35. One, designated IL-8 receptor type I, has been shown to bind GROα and NAP-2, in addition to IL-8. IL-8 acts on neutrophils to induce chemotaxis, hydrogen peroxide production, and exocytosis of intracellular granules, which is associated with an increase in the number of certain neutrophil receptors, such as the CR3 (C3bi) adhesion receptor. IL-8 also induces chemotaxis in basophils and lymphocytes, T lymphocytes, in particular. GROα and NAP-2 elicit effects in neutrophils similar to those elicited by IL-8.

3. SUMMARY OF THE INVENTION

The invention is based on polynucleotides isolated from cDNA libraries prepared from human fetal liver-spleen and fetal liver. This polynucleotide encodes a novel chemokine receptor having the amino acid sequence shown in FIG. 2 (SEQ ID NO:3). The invention provides a polynucleotide including a nucleotide sequence that is substantially equivalent to this polynucleotide. Polynucleotides according to the invention can have at least about 80%, more typically at least about 90%, and even more typically at least about 95%, sequence identity to a polynucleotide encoding a polypeptide including SEQ ID NO:3. The invention also provides the complement of the polynucleotide including a nucleotide sequence that has at least about 80%, more typically at least about 90%, and even more typically at least about 95%, sequence identity to a polynucleotide encoding a polypeptide including SEQ ID NO:3. In one embodiment, the polynucleotide of the invention includes a polynucleotide encoding a polypeptide including SEQ ID NO:3. In a variation of this embodiment, the polynucleotide includes a polynucleotide selected from SEQ ID NOs: 1 and 2. The polynucleotide can be DNA (genomic, cDNA, amplified, or synthetic) or RNA.

Polynucleotides according to the invention have numerous applications in a variety of techniques known to those skilled in the art of molecular biology. These techniques include use as hybridization probes, use as oligomers for PCR, use for chromosome and gene mapping, use in the recombinant production of protein, and use in generation of anti-sense DNA or RNA, their chemical analogs and the like. In exemplary embodiments, the polynucleotides are used in diagnostics as expressed sequence tags for identifying expressed genes or, as well known in the art and exemplified by Vollrath et al., Science 258:52–59 (1992), as expressed sequence tags for physical mapping of the human genome.

A polynucleotide according to the invention can be joined to any of a variety of other nucleotide sequences by well-established recombinant DNA techniques (cf Sambrook J et al. (1989) Molecular Cloning: A Laboratory Manual, Cold Spring Harbor Laboratory, NY). Useful nucleotide sequences for joining to polypeptides include an assortment of vectors, e.g., plasmids, cosmids, lambda phage derivatives, phagemids, and the like, that are well known in the art. Accordingly, the invention also provides a vector including a polynucleotide of the invention and a host cell containing the polynucleotide. In general, the vector contains an origin of replication functional in at least one organism, convenient restriction endonuclease sites, and a selectable marker for the host cell. Vectors according to the invention include expression vectors, replication vectors, probe generation vectors, and sequencing vectors. A host cell according to the invention can be a prokaryotic or eukaryotic cell and can be a unicellular organism or part of a multicellular organism.

An additional aspect of the invention is a process for producing a polypeptide in which a host cell containing a suitable expression vector that includes a polynucleotide of the invention is cultured under conditions that allow expression of the encoded polypeptide. The polypeptide can be recovered from the culture, conveniently from the culture medium, and further purified.

The invention further provides a polypeptide including an amino acid sequence that is substantially equivalent to SEQ ID NO:3. Polypeptides according to the invention can has at least about 80%, more typically at least about 90%, and even more typically at least about 95%, sequence identity to SEQ ID NO:3. In one embodiment, the polypeptide includes the amino acid sequence of SEQ ID NO:3.

The polypeptides according to the invention can be used in a variety of conventional procedures and methods that are currently applied to other proteins. For example, a polypeptide of the invention can be used to generate an antibody which specifically binds the polypeptide. The polypeptides of the invention are also useful for identifying the presence of and/or purifying a member of the IL-8 subfamily of chemokines. The polypeptides of the invention can also be used as molecular weight markers, and as a food supplement.

Another aspect of the invention is an antibody that specifically binds the polypeptide of the invention. Such antibodies can be either monoclonal or polyclonal antibodies, as well fragments thereof and humanized forms or fully human forms, such as those produced in transgenic animals. The invention further provides a hybridoma that produces an antibody according to the invention. Antibodies of the invention are useful for detection and/or purification of the polypeptides of the invention as well as diagnosis or therapy of activated or inflamed cells and/or tissues. In addition, the polypeptides and antibodies of the invention are useful in methods for preventing neutropenia, preventing inflammatory or other immune responses, and inhibiting disease states associated with the hyperproliferative states of progenitor cells.

BRIEF DESCRIPTION OF THE DRAWINGS

FIG. 1 shows polynucleotide sequences according to the invention. SEQ ID NO:1 was obtained from the b$^2$HFLS20W cDNA library using standard pcr, sequencing by hybridization signature analysis, and single pass gel sequencing technology. SEQ ID NO:2 is an extended version of SEQ ID NO:1 which was obtained as described in Example 33. A—adenosine; C—cytosine; G—guanosine; T—thymine; and N—any of the four bases.

FIG. 2 shows an amino acid sequence corresponding to the polynucleotide sequence of SEQ ID NO:2. This sequence is designated as SEQ ID NO:3. The open reading frame encoding SEQ ID NO:3 begins at nucleotide 129 (numbered from the 5' end) of SEQ ID NO:2. A—Alanine; R—Arginine; N—Asparagine; D—Aspartic Acid; C—Cysteine; E—Glutamic Acid; Q—Glutamine; G—Glycine; H—Histidine; I—Isoleucine; L—Leucine; K—Lysine; M—Methionine; F—Phenylalanine; P—Proline; S—Serine; T—Threonine; W—Tryptophan; Y—Tyrosine; V—Valine; X—any of the twenty amino acids.

FIG. 3 shows the sequence alignment of SEQ ID NO:3 with the IL-8 receptor type II (SEQ ID NO:4, labeled Il-8 RII.seq). The amino acid residues are designated as for FIG. 2. Gaps are indicated by dashes; residues that are identical between the two sequences are boxed.

FIG. 4 shows an alignment of the transmembrane domains of SEQ ID NO:3 and IL-8 receptor type II (SEQ ID NO:4) based on the hydrophilicity profiles determined using the Kyte-Doolittle method. Amino acid residue number is indicated above each profile, and the transmembrane domains are indicated underneath (TMD 1-7). Hydrophilicity is indicated on the y-axis (postive numbers indicate a hydrophilic character, and negative numbers indicate a hydrophobic character. The assignment of transmembrane domains in the IL-8 receptor type II (SEQ ID NO:4) is derived from Genebank annotations.

FIG. 5 shows a highly conserved region of the IL-8 receptor type II (SEQ ID NO:6 which corresponds to amino acids 140 to 148 of SEQ ID NO:4, labeled Il-8 receptor) located at the second intracellular loop between the third and fourth transmembrane domains. This region has been implicated in the signalling of G protein-coupled receptors. The corresponding region of SEQ ID NO:3 (SEQ ID NO:5 which corresponds to amino acids 123 to 131 of SEQ ID NO:3) is shown above this sequence. The serine (S), aspartate (D), and tyrosine (Y) residues that are identical between the two sequences are indicated. Conservative amino acid substitutions are indicated with a "+." The amino acid number of the first and last amino acids in these regions is indicated.

FIG. 6 shows the in vivo phosphorylation sites of the IL-8 receptor type II (SEQ ID NO:7 which corresponds to amino acids 349 to 356 of SEQ ID NO:4), which is involved in the desensitization of this receptor. The phosphorylated residues are underlined. Potential phosphylation sites are also shown for SEQ ID NO:3 (SEQ ID NO:8 which corresponds to amino acids 285 to 292 of SEQ ID NO:3).

6. DETAILED DESCRIPTION

The invention relates to novel nucleic acid sequences isolated from the b²HFLS20W cDNA library prepared from human fetal liver-spleen tissue, as described in Bonaldo et al., Genome Res. 6:791–806 (1996), using standard pcr, SBH sequence signature analysis, and Sanger sequencing techniques. The inserts of the library were amplified with pcr using primers specific for the vector sequences which flank the inserts. These inserts were analyzed by SBH to produce signatures for grouping together related insert clones. Single representative clones from each group were then selected for sequencing. The 5' sequence of the inserts was then deduced using a primer specific for M13 in a typical Sanger sequencing protocol. The present invention further includes isolated polypeptides, proteins and nucleic acid molecules which are substantially equivalent to those herein described.

6.1 Definitions

The term "nucleotide sequence" refers to a heteropolymer of nucleotides or the sequence of of these nucleotides. The terms "nucleic acid" and "polynucleotide" are also used interchangeably herein to refer to a heteropolymer of nucleotides. Generally, nucleic acid segments provided by this invention may be assembled from fragments of the genome and short oligonucleotide linkers, or from a series of oligonucleotides, to provide a synthetic nucleic acid which is capable of being expressed in a recombinant transcriptional unit comprising regulatory elements derived from a microbial or viral operon.

An "oligonucleotide fragment" or a "polynucleotide fragment", "portion," or "segment" is a stretch of polypeptide nucleotide residues which is long enough to use in polymerase chain reaction (PCR) or various hybridization procedures to identify or amplify identical or related parts of mRNA or DNA molecules.

"Oligonucleotides" or "nucleic acid probes" are prepared based on the cDNA sequence provided in the present invention. Oligonucleotides comprise portions of the DNA sequence having at least about 15 nucleotides and usually at least about 20 nucleotides. Nucleic acid probes comprise portions of the sequence having fewer nucleotides than about 6 kb, usually fewer than about 1 kb. After appropriate testing to eliminate false positives, these probes may be used to determine whether mRNAs are present in a cell or tissue or to isolate similar nucleic acid sequences from chromosomal DNA as described by Walsh P S et al (1992 PCR Methods Appl 1:241–250).

The term "probes" includes naturally occurring or recombinant single- or double-stranded nucleic acids or chemically synthesized nucleic acids. They may be labeled by nick translation, Klenow fill-in reaction, PCR or other methods well known in the art. Probes of the present invention, their preparation and/or labeling are elaborated in Sambrook J et al (1989) Molecular Cloning: A Laboratory Manual, Cold Spring Harbor Laboratory, NY; or Ausubel F M et al (1989) Current Protocols in Molecular Biology, John Wiley & Sons, New York N.Y., both incorporated herein by reference.

The term "stringent" is used to refer to conditions that are commonly understood in the art as stringent. An exemplary set of conditions include a temperature of 60–70° C., (preferably about 65° C.) and a salt concentration of 0.70 M to 0.80 M (preferably about 0.75M). Further exemplary conditions include, hybridizing conditions that (1) employ low ionic strength and high temperature for washing, for example, 0.015 M NaCl/0.0015 M sodium citrate/0.1% SDS at 50(C.; (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42(C; or (3) employ 50% formamide, 5×SSC (0.75 M NaCl, 0.075 M Sodium pyrophosphate, 5×Denhardt's solution, sonicated salmon sperm DNA (50 g/ml), 0.1% SDS, and 10% dextran sulfate at 42(C, with washes at 42(C in 0.2×SSC and 0.1% SDS.

The term "recombinant," as used herein, means that a polypeptide or protein is derived from recombinant (e.g., microbial or mammalian) expression systems. "Microbial" refers to recombinant polypeptides or proteins made in bacterial or fungal (e.g., yeast) expression systems. As a product, "recombinant microbial" defines a polypeptide or protein essentially free of native endogenous substances and unaccompanied by associated native glycosylation. Polypeptides or proteins expressed in most bacterial cultures, e.g., *E. coli,* will be free of glycosylation modifications; polypeptides or proteins expressed in yeast will have a glycosylation pattern different from that expressed in mammalian cells.

The term "recombinant expression vehicle or vector" refers to a plasmid or phage or virus or vector, for expressing a polypeptide from a DNA (RNA) sequence. The expression vehicle can comprise a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription initiation and termination sequences. Structural units intended for use in yeast or eukaryotic expression systems preferably include a leader sequence enabling extracellular secretion of translated protein by a host cell. Alternatively, where recombinant protein is expressed without a leader or transport sequence, it may include an N-terminal methionine residue. This residue may or may not be subsequently cleaved from the expressed recombinant protein to provide a final product.

"Recombinant expression system" means host cells which have stably integrated a recombinant transcriptional unit into chromosomal DNA or carry the recombinant transcriptional unit extrachromosomally. The cells can be prokaryotic or eukaryotic. Recombinant expression systems as defined herein will express heterologous polypeptides or proteins upon induction of the regulatory elements linked to the DNA segment or synthetic gene to be expressed.

The term "open reading frame," ORF, means a series of triplets coding for amino acids without any termination codons and is a sequence translatable into protein.

The term "expression modulating fragment," EMF, means a series of nucleotide molecules which modulates the expression of an operably linked ORF or EMF.

As used herein, a sequence is said to "modulate the expression of an operably linked sequence" when the expression of the sequence is altered by the presence of the EMF. EMFs include, but are not limited to, promoters, and promoter modulating sequences (inducible elements). One class of EMFs are fragments which induce the expression or an operably linked ORF in response to a specific regulatory factor or physiological event.

As used herein, an "uptake modulating fragment," UMF, means a series of nucleotide molecules which mediate the uptake of a linked DNA fragment into a cell. UMFs can be readily identified using known UMFs as a target sequence or target motif with the computer-based systems described above.

The presence and activity of a UMF can be confirmed by attaching the suspected UMF to a marker sequence. The resulting nucleic acid molecule is then incubated with an appropriate host under appropriate conditions and the uptake of the marker sequence is determined. As described above, a UMF will increase the frequency of uptake of a linked marker sequence.

"Active" refers to those forms of the polypeptide which retain the biologic and/or immunologic activities of any naturally occurring polypeptide.

"Naturally occurring polypeptide" refers to polypeptides produced by cells that have not been genetically engineered and specifically contemplates various polypeptides arising from post-translational modifications of the polypeptide including, but not limited to, acetylation, carboxylation, glycosylation, phosphorylation, lipidation and acylation.

"Derivative" refers to polypeptides chemically modified by such techniques as ubiquitination, labeling (e.g., with radionuclides or various enzymes), pegylation (derivatization with polyethylene glycol) and insertion or substitution by chemical synthesis of amino acids such as ornithine, which do not normally occur in human proteins.

"Recombinant variant" refers to any polypeptide differing from naturally occurring polypeptides by amino acid insertions, deletions, and substitutions, created using recombinant DNA techniques. Guidance in determining which amino acid residues may be replaced, added or deleted without abolishing activities of interest, such as cellular trafficking, may be found by comparing the sequence of the particular polypeptide with that of homologous peptides and minimizing the number of amino acid sequence changes made in regions of high homology.

Preferably, amino acid "substitutions" are the result of replacing one amino acid with another amino acid having similar structural and/or chemical properties, such as the replacement of a leucine with an isoleucine or valine, an aspartate with a glutamate, or a threonine with a serine, i.e., conservative amino acid replacements. "Insertions" or "deletions" are typically in the range of about 1 to 5 amino acids. The variation allowed may be experimentally determined by systematically making insertions, deletions, or substitutions of amino acids in a polypeptide molecule using recombinant DNA techniques and assaying the resulting recombinant variants for activity.

As used herein, "substantially equivalent" can refer both to nucleotide and amino acid sequences, for example a mutant sequence, that varies from a reference sequence by one or more substitutions, deletions, or additions, the net effect of which does not result in an adverse functional dissimilarity between the reference and subject sequences. Typically, such a mutant sequence varies from one of those listed herein by no more that about 20% (i.e., the number of substitutions, additions, and/or deletions in a mutant sequence, as compared to the corresponding listed sequence, divided by the total number of residues in the mutant sequence is about 0.2 or less). Such a mutant sequence is said to have 80% sequence identity to the listed sequence. In one embodiment, a mutant sequence of the invention varies from a listed sequence by no more than 10% (90% sequence identity), and in a variation of this embodiment, by no more than 5% (95% sequence identity). For the purposes of the present invention, sequences having substantially equivalent biological activity and substantially equivalent expression characteristics are considered substantially equivalent. For the purposes of determining equivalence, truncation of the mature sequence should be disregarded.

Where desired an expression vector may be designed to contain a "signal or leader sequence" which will direct the polypeptide through the membrane of a cell. Such a sequence may be naturally present on the polypeptides of the present invention or provided from heterologous protein sources by recombinant DNA techniques.

A polypeptide "fragment," "portion," or "segment" is a stretch of amino acid residues of at least about 5 amino acids, often at least about 7 amino acids, typically at least about 9 to 13 amino acids, and, in various embodiments, at least about 17 or more amino acids. To be active, any polypeptide must have sufficient length to display biologic and/or immunologic activity.

Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations in the polypeptide sequence may be reflected in the polypeptide or domains of other peptides added to the polypeptide to modify the properties of any part of the polypeptide, to change characteristics such as ligand-binding affinities, interchain affinities, or degradation/turnover rate.

"Activated" cells as used in this application are those which are engaged in extracellular or intracellular membrane trafficking, including the export of neurosecretory or enzymatic molecules as part of a normal or disease process.

The term "purified" as used herein denotes that the indicated nucleic acid or polypeptide is present in the substantial absence of other biological macromolecules, e.g., polynucleotides, proteins, and the like. In one embodiment, the polynucleotide or polypeptide is purified such that it constitutes at least 95% by weight, more preferably at least 99.8% by weight, of the indicated biological macromolecules present (but water, buffers, and other small molecules, especially molecules having a molecular weight of less than 1000 daltons, can be present).

The term "isolated" as used herein refers to a nucleic acid or polypeptide separated from at least one other component (e.g., nucleic acid or polypeptide) present with the nucleic acid or polypeptide in its natural source. In one embodiment, the nucleic acid or polypeptide is found in the presence of (if anything) only a solvent, buffer, ion, or other component normally present in a solution of the same. The terms "isolated" and "purified" do not encompass nucleic acids or polypeptides present in their natural source.

The term "infection" refers to the introduction of nucleic acids into a suitable host cell by use of a virus or viral vector.

The term "transformation" means introducing DNA into a suitable host cell so that the DNA is replicable, either as an extrachromosomal element, or by chromosomal integration.

The term "transfection" refers to the taking up of an expression vector by a suitable host cell, whether or not any coding sequences are in fact expressed.

The term "intermediate fragment" means a nucleic acid between 5 and 1000 bases in length, and preferably between 10 and 40 bp in length.

Each of the above terms is meant to encompasses all that is described for each, unless the context dictates otherwise.

6.2 Sequencing by Hybridization

SBH is a well developed technology that may be practiced by a number of methods known to those skilled in the art. Specifically, techniques related to sequencing by hybridization of the following documents is incorporated by reference herein: Drmanac et al., U.S. Pat. No. 5,202,231 (hereby incorporated by reference herein)—Issued Apr. 13, 1993; Drmanac et al., U.S. Pat. No. 5,525,464 (hereby incorporated by reference herein)—Issued Jun. 11, 1996; Drmanac, PCT Patent Appln. No. WO 95/09248 (hereby incorporated by reference); Drmanac et al., *Genomics*, 4, 114–128 (1989); Drmanac et al., *Proceedings of the First Int'l. Conf. Electrophoresis Supercomputing Human Genome Cantor* et al. eds, World Scientific Pub. Co., Singapore, 47–59 (1991); Drmanac et al., *Science*, 260, 1649–1652 (1993); Lehrach et al., *Genome Analysis: Genetic and Physical Mapping*, 1, 39–81 (1990), Cold Spring Harbor Laboratory Press; Drmanac et al., *Nucl. Acids Res.*, 4691 (1986); Stevanovic et al., *Gene*, 79, 139 (1989); Panusku et al., *Mol. Biol. Evol.*, 1, 607 (1990); Nizetic et al., *Nucl. Acids Res.*, 19, 182 (1991); Drmanac et al., *J. Biomol. Struct. Dyn.*, 5, 1085 (1991); Hoheisel et al., *Mol. Gen.*, 4, 125–132 (1991); Strezoska et al., *Proc. Nat'l. Acad. Sci.* (USA), 88, 10089 (1991); Drmanac et al., *Nucl. Acids Res.*, 19, 5839 (1991); and Drmanac et al., *Int. J. Genome Res.*, 1, 59–79 (1992).

Format 1 SBH is appropriate for the simultaneous analysis of a large set of samples. Parallel scoring of thousands of samples on large arrays may be performed are in thousands of independent hybridization reactions using small pieces of membranes. The identification of DNA may involve 1–20 probes per reaction and the identification of mutations may in some cases involve more than 1000 probes specifically selected or designed for each sample. For identification of the nature of the mutated DNA segments, specific probes may be synthesized or selected for each mutation detected in the first round of hybridizations.

DNA samples may be prepared in small arrays which may be separated by appropriate spacers, and which may be simultaneously tested with probes selected from a set of oligonucleotides which may be arrayed in multiwell plates. Small arrays may consist of one or more samples. DNA samples in each small array may include mutants or individual samples of a sequence. Consecutive small arrays may be organized into larger arrays. Such larger arrays may include replication of the same small array or may include arrays of samples of different DNA fragments. A universal set of probes includes sufficient probes to analyze a DNA fragment with prespecified precision, e.g. with respect to the redundancy of reading each base pair ("bp"). These sets may include more probes than are necessary for one specific fragment, but may include fewer probes than are necessary for testing thousands of DNA samples of different sequence.

DNA or allele identification and a diagnostic sequencing process may include the steps of:

1) Selection of a subset of probes from a dedicated, representative or universal set to be hybridized with each of a plurality small arrays;
2) Adding a first probe to each subarray on each of the arrays to be analyzed in parallel;
3) Performing hybridization and scoring of the hybridization results;
4) Stripping off previously used probes;
5) Repeating hybridization, scoring and stripping steps for the remaining probes which are to be scored;
5) Processing the obtained results to obtain a final analysis or to determine additional probes to be hybridized;
6) Performing additional hybridizations for certain subarrays; and
7) Processing complete sets of data and computing obtaining a final analysis.

This approach provides fast identification and sequencing of a small number of nucleic acid samples of one type (e.g. DNA, RNA), and also provides parallel analysis of many sample types in the form of subarrays by using a presynthesized set of probes of manageable size. Two approaches have been combined to produce an efficient and versatile process for the determination of DNA identity, for DNA diagnostics, and for identification of mutations.

For the identification of known sequences, a small set of shorter probes may be used in place of a longer unique probe. In this approach, although there may be more probes to be scored, a universal set of probes may be synthesized to cover any type of sequence. For example, a full set of 6-mers includes only 4,096 probes, and a complete set of 7-mers includes only 16,384 probes.

Full sequencing of a DNA fragment may be performed with two levels of hybridization. One level is hybridization of a sufficient set of probes that cover every base at least once. For this purpose, a specific set of probes may be synthesized for a standard sample. The results of hybridization with such a set of probes reveal whether and where mutations (differences) occur in non-standard samples. To determine the identity of the changes, additional specific probes may be hybridized to the sample.

In another embodiment, all probes from a universal set may be scored. A universal set of probes allows scoring of a relatively small number of probes per sample in a two step process without an undesirable expenditure of time. The hybridization process may involve successive probings, in a first step of computing an optimal subset of probes to be hybridized first and, then, on the basis of the obtained results, a second step of determining additional probes to be scored from among those in a universal set.

In SBH sequence assembly, K-1 oligonucleotides which occur repeatedly in analyzed DNA fragments due to chance or biological reasons may be subject to special consideration. If there is no additional information, relatively small fragments of DNA may be fully assembled in as much as every base pair is read several times.

6.2.1 Solving Branch Points for Sequence Assembly

In the assembly of relatively longer fragments, ambiguities may arise due to the repeated occurrence in a set of positively-scored probes of a K-1 sequence (i.e., a sequence shorter than the length of the probe). This problem does not exist if mutated or similar sequences have to be determined (i.e., the K-1 sequence is not identically repeated). Knowledge of one sequence may be used as a template to correctly assemble a sequence known to be similar (e.g. by its presence in a database) by arraying the positive probes for the unknown sequence to display the best fit on the template.

Within DNA, the location of certain probes may be interchangeable when determined by overlapping the sequence data, resulting in an ambiguity as to the position of the partial sequence. Although the sequence information is determined by SBH, either: (i) long read length, single-pass gel sequencing at a fraction of the cost of complete gel sequencing; or (ii) comparison to related sequences, may be used to order hybridization data where such ambiguities ("branch points") occur. In addition, segments in junk DNA (which is not found in genes) may be repeated many times in tandem. Although the sequence of the segments is determined by SBH, single-pass gel sequencing may be used to determine the number of tandem repeats where tandemly-repeated segments occur. As tandem repeats occur rarely in protein-encoding portions of a gene, the gel-sequencing step will be performed only when a commercial value for the sequence is determined.

6.2.2 Sequencing of Mutants

The use of an array of sample arrays avoids consecutive scoring of many oligonucleotides on a single sample or on a small set of samples. This approach allows the scoring of more probes in parallel by manipulation of only one physical object. Subarrays of DNA samples 1000 bp in length may be sequenced in a relatively short period of time. If the samples are spotted at 50 subarrays in an array and the array is reprobed 10 times, 500 probes may be scored. In screening for the occurrence of a mutation, approximately 335 probes may be used to cover each base three times. If a mutation is present, several covering probes will be affected. The use of information about the identity of negative probes may map the mutation with a two base precision. To solve a single base mutation mapped with this precision, an additional 15 probes may be employed. These probes cover any base combination for two questionable positions (assuming that deletions and insertions are not involved). These probes may be scored in one cycle on 50 subarrays which contain a given sample. In the implementation of a multiple label color scheme (i.e., multiplexing), two to six probes, each having a different label such as a different fluorescent dye, may be used as a pool, thereby reducing the number of hybridization cycles and shortening the sequencing process.

In more complicated cases, there may be two close mutations or insertions. They may be handled with more probes. For example, a three base insertion may be solved with 64 probes. The most complicated cases may be approached by several steps of hybridization, and the selecting of a new set of probes on the basis of results of previous hybridizations.

If subarrays to be analyzed include tens or hundreds of samples of one type, then several of them may be found to contain one or more changes (mutations, insertions, or deletions). For each segment where mutation occurs, a specific set of probes may be scored. The total number of probes to be scored for a type of sample may be several hundreds. The scoring of replica arrays in parallel facilitates scoring of hundreds of probes in a relatively small number of cycles. In addition, compatible probes may be pooled. Positive hybridizations may be assigned to the probes selected to check particular DNA segments because these segments usually differ in 75% of their constituent bases.

By using a larger set of longer probes, longer targets may be conveniently analyzed. These targets may represent pools of shorter fragments such as pools of exon clones.

6.2.3 Identification of Heterozygotes Using SBH

A specific hybridization scoring method may be employed to define the presence of heterozygotes (sequence variants) in a genomic segment to be sequenced from a diploid chromosomal set. Two variations are where: i) the sequence from one chromosome represents a basic type and the sequence from the other represents a new variant; or, ii) both chromosomes contain new, but different variants. In the first case, the scanning step designed to map changes gives a maximal signal difference of two-fold at the heterozygotic position. In the second case, there is no masking, but a more complicated selection of the probes for the subsequent rounds of hybridizations may be indicated.

Scoring two-fold signal differences required in the first case may be achieved efficiently by comparing corresponding signals with controls containing only the basic sequence type and with the signals from other analyzed samples. This approach allows determination of a relative reduction in the hybridization signal for each particular probe in a given sample. This is significant because hybridization efficiency may vary more than two-fold for a particular probe hybridized with different DNA fragments having the same full match target. In addition, heterozygotic sites may affect more than one probe depending upon the number of oligonucleotide probes. Decrease of the signal for two to four consecutive probes produces a more significant indication of heterozygotic sites. Results may be checked by testing with small sets of selected probes among which one or few probes selected to give a full match signal which is on average eight-fold stronger than the signals coming from mismatch-containing duplexes.

Partitioned membranes allow a very flexible organization of experiments to accommodate relatively larger numbers of samples representing a given sequence type, or many different types of samples represented with relatively small numbers of samples. A range of 4–256 samples can be handled with particular efficiency. Subarrays within this range of numbers of dots may be designed to match the configuration and size of standard multiwell plates used for storing and labelling oligonucleotides. The size of the subarrays may be adjusted for different number of samples, or a few standard subarray sizes may be used. If all samples of a type do not fit in one subarray, additional subarrays or membranes may be used and processed with the same probes. In addition, by adjusting the number of replicas for each subarray, the time for completion of identification or sequencing process may be varied.

6.2.4 Signature Analysis with SBH

Obtaining information about the degree of hybridization exhibited for a set of only about 200 oligonucleotides probes (about 5% of the effort required for complete sequencing) defines a unique signature of each gene and may be used for sorting the cDNAs from a library to determine if the library contains multiple copies of the same gene. By such signatures, identical, similar and different cDNAs can be distinguished and inventoried.

6.3 Format III Sequencing by Hybridization

In Format 3, a first set of oligonucleotide probes of known sequence is immobilized on a solid support under conditions which permit them to hybridize with nucleic acids having respectively complementary sequences. A labeled, second set of oligonucleotide probes is provided in solution. Both within the sets and between the sets the probes may be of the same length or of different lengths. A nucleic acid to be sequenced or intermediate fragments thereof may be applied to the first set of probes in double-stranded form (especially where a recA protein is present to permit hybridization under non-denaturing conditions), or in single-stranded form and under conditions which permit hybrids of different degrees of complementarity (to example, under conditions which discriminate between full match and one base pair mismatch hybrids). The nucleic acid to be sequenced or intermediate fragments thereof may be applied to the first set of probes before, after or simultaneously with the second set of probes. A ligase or other means of causing chemical bond formation between adjacent, but not between nonadjacent, probes may be applied before, after or simultaneously with the second set of probes. After permitting adjacent probes to be chemically bended, fragments and probes which are not immobilized to the surface by chemical bonding to a member of the first set of probe are washed away, for example, using a high temperature (up to 100 degrees C.) wash solution which melts hybrids. The bound probes from the second set may then be detected using means appropriate to the label employed (which may be chemiluminescent, fluorescent, radioactive, enzymatic or densitometric, for example).

Herein, nucleotide bases "match" or are "complementary" if they form a stable duplex by hydrogen bonding under specified conditions. For example, under conditions commonly employed in hybridization assays, adenine ("A") matches thymine ("T"), but not guanine ("G") or cytosine ("C"). Similarly, G matches C, but not A or T. Other bases which will hydrogen bond in less specific fashion, such as inosine or the Universal Base ("M"base, Nichols et al 1994), or other modified bases, such as methylated bases, for example, are complementary to those bases for which they form a stable duplex under specified conditions. A probe is said to be "perfectly complementary" or is said to be a "perfectly match" if each base in the probe forms a duplex by hydrogen bonding to a base in the nucleic acid to be sequenced. Each base in a probe that does not form a stable duplex is said to be a "mismatch" under the specified hybridization conditions.

A list of probes may be assembled wherein each probe is a perfect match to the nucleic acid to be sequenced. The probes on this list may then be analyzed to order them in maximal overlap fashion. Such ordering may be accomplished by comparing a first probe to each of the other probes on the list to determine which probe has a 3' end which has the longest sequence of bases identical to the sequence of bases at the 5' end of a second probe. The first and second probes may then be overlapped, and the process may be repeated by comparing the 5' end of the second probe to the 3' end of all of the remaining probes and by comparing the 3' end of the first probe with the 5' end of all of the remaining probes. The process may be continued until there are no probes on the list which have not been overlapped with other probes. Alternatively, more than one probe may be selected from the list of positive probes, and more than one set of overlapped probes ("sequence nucleus") may be generated in parallel. The list of probes for either such process of sequence assembly may be the list of all probes which are perfectly complementary to the nucleic acid to be sequenced or may be any subset thereof.

The 5' and 3' ends of sequence nuclei may be overlapped to generate longer stretches of sequence. Where ambiguities arise in sequence assembly due to the availability of alternative proper overlaps with probes or sequence nuclei, hybridization with longer probes spanning the site of overlap alternatives, competitive hybridization, ligation of alternative end to end pairs of probes spanning the site of ambiguity or single pass gel analysis (to provide an unambiguous framework for sequence assembly) may be used.

By employing the above procedures, one may obtain any desired level of sequence, from a pattern of hybridization (which may be correlated with the identity of a nucleic acid sample to serve as a signature for identifying the nucleic acid sample) to overlapping or non-overlapping probes up through assembled sequence nuclei and on to complete sequence for an intermediate fragment or an entire source DNA molecule (e.g. a chromosome).

Sequencing may generally comprise the following steps:

(a) contacting an array of immobilized oligonucleotide probes with a nucleic acid fragment under conditions effective to allow a fragment with a sequence complementary to that of an immobilized probe to form a primary complex with the immobilized probe such that the fragment has a hybridized and a non-hybridized portion;

(b) contacting a primary complex with a set of labeled oligonucleotide probes in solution under conditions effective to allow a primary complex including an unhybridized sequence complementary to that of a labeled probe to hybridize to the labeled probe, thereby forming a secondary complex wherein the fragment is hybridized with both an immobilized probe and a labeled probe;

(c) removing from a secondary complex any labeled probe that has not hybridized adjacent to an immobilized probe;

(d) detecting the presence of adjacent labeled and unlabeled probes by detecting the presence of the label; and (e) determining a nucleotide sequence of the fragment by connecting the known sequence of the immobilized and labeled probes.

In this embodiment of SBH, ligation may be implemented by a chemical ligating agent (e.g. water-soluble carbodiimide or cyanogen bromide). A ligase enzyme, such as the commercially available $T_4$ DNA ligase from $T_4$ bacteriophage, may be employed. The washing conditions which are selected to distinguish between adjacent versus nonadjacent labeled and immobilized probes are selected to make use of the difference in stability of continuously stacked or ligated adjacent probes.

6.4 Hybridization Conditions

Hybridization and washing conditions may be selected to detect substantially perfect match hybrids (such as those wherein the fragment and probe hybridize at six out of seven positions), or may be selected to permit detection only of perfect match hybrids by the use of more stringent hybridization conditions.

Suitable hybridization conditions may be routinely determined by optimization procedures or pilot studies. Such procedures and studies are routinely conducted by those skilled in the art to establish protocols for use in a laboratory. See e.g., Ausubel et al., Current Protocols in Molecular Biology, Vol. 1–2, John Wiley & Sons (1989); Sambrook et al., Molecular Cloning A Laboratory Manual, 2nd Ed., Vols. 1–3, Cold Springs Harbor Press (1989); and Maniatis et al., Molecular Cloning: A Laboratory Manual, Cold Spring Harbor Laboratory Cold Spring Harbor, N.Y. (1982), all of which are incorporated by reference herein. For example, conditions such as temperature, concentration of components, hybridization and washing times, buffer components, and their pH and ionic strength may be varied.

In embodiments wherein the labeled and immobilized probes are not physically or chemically linked, detection may rely solely on washing steps of controlled stringency. Under such conditions, adjacent probes remain hybridized due to a stability afforded by stacking interactions. Conditions may be varied to optimize the process as described above.

6.5 Probes and Labeling of Probes

Oligonucleotide probes may be labeled with fluorescent dyes, chemiluminescent systems, radioactive labels (e.g., $^{35}S$, $^{3}H$, $^{32}P$ or $^{33}P$) or with isotopes detectable by mass spectrometry, by any of a variety of methods that are well known in the art.

Other variations include the use of modified oligonucleotides to increase specificity or efficiency, cycling hybridizations to increase the hybridization signal, for example by performing a hybridization cycle under conditions (e.g. temperature) optimally selected for a first set of labeled probes followed by hybridization under conditions optimally selected for a second set of labeled probes.. Shifts in reading frame may be determined by using mixtures (preferably mixtures of equimolar amounts) of probes ending in each of the four nucleotide bases A, T, C and G.

6.6 Preparation of Sample Nucleic Acid

Where a nucleic acid molecule of unknown sequence is longer than about 45 or 50 bp, the molecule may be fragmented and the sequences of the fragments determined. Fragmentation may be accomplished by restriction enzyme digestion, shearing or NaOH. Fragments may be separated by size (e.g. by gel electrophoresis) to obtain a preferred fragment length of about ten to forty bps.

Oligonucleotides may be immobilized, by a number of methods known to those skilled in the art, such as laser-activated photodeprotection attachment through a phosphate group using reagents such as a nucleoside phosphoramidite or a nucleoside hydrogen phosphorate. Glass, nylon, silicon and fluorocarbon supports may be used.

Oligonucleotides may be organized into an array or arrays including all or a subset of all probes of a given length, or of sets of probes of selected lengths. Hydrophobic partitions may be used to separate probes or arrays of probes. Arrays may be designed for various applications (e.g. mapping, partial sequencing, sequencing of targeted regions for diagnostic purposes, mRNA sequencing and large scale sequencing). A specific chip may be designed to be dedicated to a particular application by selecting a combination and arrangement of probes on a substrate.

For example, 1000 immobilized probe arrays of all oligonucleotide probes 5 bases in length (each array containing 1000 distinct probes) may be constructed. A second set of 1000 oligonucleotide probes may be labeled, and one of each labeled probe may be applied to an array of immobilized probes along with a fragment to be sequenced. In this example, 1000 of the arrays would be combined in a large superarray, or "superchip." In those instances where an immobilized probe and one of the labeled probes hybridize end-to-end along a nucleic acid fragment., the two probes are joined, for example by ligation, and, after washing to remove unbound label, 10-mers complementary to the sample fragment are detected by the correlation of the presence of a label at a point in an array having an immobilized probe of known sequence to which was applied a labeled probe of known sequence. The sequence of the sample fragment is simply the sequence of the immobilized probe continued in the sequence of the labeled probe. In this way, all one million possible 10-mers may be tested by a combinatorial process which employs only 5-mers and which thus involves one thousandth of the amount of effort for oligonucleotide synthesis and quality control.

A nucleic acid sample to be sequenced may be fragmented or otherwise treated (for example, by the use of recA) to avoid hindrance to hybridization from secondary structure in the sample. The sample may be fragmented by, for example, digestion with a restriction enzyme such as the Cvi JI, physical shearing (e.g. by ultrasound ), or by NaOH treatment. The resulting fragments may be separated oby gel electrophoresis and fragments of an appropriate length, such as between about 10 bp and about 40 bp, may be extracted from the gel.

For example, a reusable Format 3 SBH array may be produced by introducing a specifically cleavable bond between the probes and then by cleaving the bond after detection. The labeled probes may be ribonucleotides or a ribonucleotide may be used as the joining base in the labeled probe so that this probe may subsequently be removed by RNAse or uracil-DNA glycosylate treatment. In addition, bonds produced by chemical ligation may be selectively cut.

6.7 Nucleic Acids of the Invention

The sequences falling within the scope of the present invention are not limited to the specific sequences herein described, but also include allelic and species variations thereof. Allelic and species variations can be routinely determined by comparing the sequence provided in SEQ ID NOs:1–2, a representative fragment thereof, or a nucleotide sequence at least 99.9% identical to SEQ ID NO:1–2 with a sequence from another isolate of the same species. Furthermore, to accommodate codon variability, the invention includes nucleic acid molecules coding for the same amino acid sequences as do the specific ORFs disclosed herein. In other words, in the coding region of an ORF, substitution of one codon for another which encodes the same amino acid is expressly contemplated.

Any specific sequence disclosed herein can be readily screened for errors by resequencing a particular fragment, such as an ORF, in both directions (i.e., sequence both strands).

The present invention further provides recombinant constructs comprising a nucleic acid having the sequence of any one of SEQ ID NOs: 1–2 or a fragment thereof. The recombinant constructs of the present invention comprise a vector, such as a plasmid or viral vector, into which a nucleic acid having the sequence of any one of SEQ ID NOs 1–2 or a fragment thereof is inserted, in a forward or reverse orientation. In the case of a vector comprising one of the ORFs of the present invention, the vector may further comprise regulatory sequences, including for example, a promoter, operably linked to the ORF. For vectors comprising the EMFs and UMFs of the present invention, the vector may further comprise a marker sequence or heterologous ORF operably linked to the EMF or UMF. Large numbers of suitable vectors and promoters are known to those of skill in the art and are commercially available for generating the recombinant constructs of the present invention. The following sectors are provided by way of example. Bacterial: pBs, phagescript, PsiX174, pBluescript SK, pBs KS, pNH8a, pNH16a, pNH18a, pNH46a (Stratagene); pTrc99A, pKK223-3, pKK233-3, pDR540, pRIT5 (Pharmacia). Eukaryotic: pWLneo, pSV2cat, pOG44, PXTI, pSG (Stratagene) pSVK3, pBPV, pMSG, pSVL (Pharmacia).

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, and trc. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

Generally, recombinant expression vectors will include origins of replication and selectable markers permitting transformation of the host cell, e.g., the ampicillin resistance gene of *E. coli* and *S. cerevisiae* TRP 1 gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM 1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced or derepressed by appropriate means (e.g., temperature shift or chemical induction) and cells are cultured for an additional period. Cells are typically harvested by centrifugation, disrupted by physical or chemical means, and the resulting crude extract retained for further purification.

Included within the scope of the nucleic acid sequences of the invention are nucleic acid sequences that hybridize under stringent conditions to a fragment of the DNA sequences in FIG. 1, which fragment is greater than about 10 bp, preferably 20–50 bp, and even greater than 100 bp.

In accordance with the invention, polynucleotide sequences which encode the novel nucleic acids, or functional equivalents thereof, may be used to generate recombinant DNA molecules that direct the expression of that nucleic acid, or a functional equivalent thereof, in appropriate host cells.

The nucleic acid sequences of the invention are further directed to sequences which encode variants of the described nucleic acids. These amino acid sequence variants may be prepared by methods known in the art by introducing appropriate nucleotide changes into a native or variant polynucleotide. There are two variables in the construction of amino acid sequence variants: the location of the mutation and the nature of the mutation. The amino acid sequence variants of the nucleic acids are preferably constructed by mutating the polynucleotide to give an amino acid sequence that does not occur in nature. These amino acid alterations can be made at sites that differ in the nucleic acids from different species (variable positions) or in highly conserved regions (constant regions). Sites at such locations will typically be modified in series, e.g., by substituting first with conservative choices (e.g., hydrophobic amino acid to a different hydrophobic amino acid) and then with more distant choices (e.g., hydrophobic amino acid to a charged amino acid), and then deletions or insertions may be made at the target site.

Amino acid sequence deletions generally range from about 1 to 30 residues, preferably about 1 to 10 residues, and are typically contiguous. Amino acid insertions include amino- and/or carboxyl-terminal fusions ranging in length from one to one hundred or more residues, as well as intrasequence insertions of single or multiple amino acid residues. Intrasequence insertions may range generally from about 1 to 10 amino residues, preferably from 1 to 5 residues. Examples of terminal insertions include the heterologous signal sequences necessary for secretion or for intracellular targeting in different host cells.

In a preferred method, polynucleotides encoding the novel nucleic acids are changed via site-directed mutagenesis. This method uses oligonucleotide sequences that encode the polynucleotide sequence of the desired amino acid variant, as well as a sufficient adjacent nucleotide on both sides of the changed amino acid to form a stable duplex on either side of the site of being changed. In general, the techniques of site-directed mutagenesis are well known to those of skill in the art and this technique is exemplified by publications such as, Edelman et al., *DNA* 2:183 (1983). A versatile and efficient method for producing site-specific changes in a polynucleotide sequence was published by Zoller and Smith, *Nucleic Acids Res.* 10:6487–6500 (1982).

PCR may also be used to create amino acid sequence variants of the novel nucleic acids. When small amounts of template DNA are used as starting material, primer(s) that differs slightly in sequence from the corresponding region in the template DNA can generate the desired amino acid variant. PCR amplification results in a population of product DNA fragments that differ from the polynucleotide template encoding the polypeptide at the position specified by the primer. The product DNA fragments replace the corresponding region in the plasmid and this gives the desired amino acid variant.

A further technique for generating amino acid variants is the cassette mutagenesis technique described in Wells et al., *Gene* 34:315 (1985); and other mutagenesis techniques well known in the art, such as, for example, the techniques in Sambrook et al., supra, and *Current Protocols in Molecular Biology,* Ausubel et al.

Due to the inherent degeneracy of the genetic code, other DNA sequences which encode substantially the same or a functionally equivalent amino acid sequence may be used in the practice of the invention for the cloning and expression of these novel nucleic acids. Such DNA sequences include those which are capable of hybridizing to the appropriate novel nucleic acid sequence under stringent conditions.

6.8 Hosts

The present invention further provides host cells containing SEQ ID NOs:1–2 of the present invention, wherein the nucleic acid has been introduced into the host cell using known transformation, transfection or infection methods. The host cell can be a higher eukaryotic host cell, such as a mammalian cell, a lower eukaryotic host cell, such as a yeast cell, or the host cell can be a prokaryotic cell, such as a bacterial cell. Introduction of the recombinant construct into the host cell can be effected by calcium phosphate transfection, DEAE, dextran mediated transfection, or electroporation (Davis, L. et al., *Basic Methods in Molecular Biology* (1986)).

The host cells containing one of SEQ ID NOs:1–2 of the present invention, can be used in conventional manners to produce the gene product encoded by the isolated fragment (in the case of an ORF) or can be used to produce a heterologous protein under the control of the EMF.

Any host/vector system can be used to express one or more of the ORFs of the present invention. These include, but are not limited to, eukaryotic hosts such as HeLa cells, Cv-1 cell, COS cells, and Sf9 cells, as well as prokaryotic host such as *E. coli* and *B. subtilis.* The most preferred cells are those which do not normally express the particular polypeptide or protein or which expresses the polypeptide or protein at low natural level.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., in *Molecular Cloning: A Laboratory Manual,* Second Edition, Cold Spring Harbor, N.Y. (1989), the disclosure of which is hereby incorporated by reference.

Various mammalian cell culture systems can also be employed to express recombinant protein. Examples of mammalian expression systems include the COS-7 lines of monkey kidney fibroblasts, described by Gluzman, *Cell* 23:175 (1981), and other cell lines capable of expressing a compatible vector, for example, the C127, 3T3, CHO, HeLa and BHK cell tines. Mammalian expression vectors will comprise an origin of replication, a suitable promoter and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements.

Recombinant polypeptides and proteins produced in bacterial culture are usually isolated by initial extraction from cell pellets, followed by one or more salting-out, aqueous ion exchange or size exclusion chromatography steps. Protein refolding steps can be used, as necessary, in completing configuration of the mature protein. Finally, high performance liquid chromatography (HPLC) can be employed for final purification steps. Microbial cells employed in expression of proteins can be disrupted by any convenient method, including freeze-thaw cycling, sonication, mechanical disruption, or use of cell lysing agents.

6.9 Peptides

The present invention further provides isolated polypeptides encoded by the nucleic acid fragments of the present invention or by degenerate variants of the nucleic acid fragments of the present invention. By "degenerate variant" is intended nucleotide fragments which differ from a nucleic acid fragment of the present invention (e.g., an ORF) by nucleotide sequence but, due to the degeneracy of the Genetic Code, encode an identical polypeptide sequence. Preferred nucleic acid fragments of the present invention are the ORFs which encode proteins.

A variety of methodologies known in the art can be utilized to obtain any one of the isolated polypeptides or proteins of the present invention. At the simplest level, the amino acid sequence can be synthesized using commercially available peptide synthesizers. This is particularly useful in producing small peptides and fragments of larger polypeptides. Fragments are useful, for example, in generating antibodies against the native polypeptide. In an alternative method, the polypeptide or protein is purified from bacterial cells which naturally produce the polypeptide or protein. One skilled in the art can readily follow known methods for isolating polypeptides and proteins in order to obtain one of the isolated polypeptides or proteins of the present invention. These include, but are not limited to, immunochromatography, HPLC, size-exclusion chromatography, ion-exchange chromatography, and immuno-affinity chromatography. See, e.g., Scopes, *Protein Purification: Principles and Practice,* Springer-Verlag (1994); Sambrook, et al., in *Molecular Cloning: A Laboratory Manual;* Ausubel et al., *Current Protocols in Molecular Biology.*

The polypeptides and proteins of the present invention can alternatively be purified from cells which have been altered to express the desired polypeptide or protein. As used herein, a cell is said to be altered to express a desired polypeptide or protein when the cell, through genetic manipulation, is made to produce a polypeptide or protein which it normally does not produce or which the cell normally produces at a lower level. One skilled in the art can readily adapt procedures for introducing and expressing either recombinant or synthetic sequences into eukaryotic or prokaryotic cells in order to generate a cell which produces one of the polypeptides or proteins of the present invention.

The purified polypeptides are used in in vitro binding assays which are well known in the art to identify molecules which bind to the polypeptides. These molecules include but are not limited to, for e.g., small molecules, molecules from combinatorial libraries, antibodies or other proteins. The molecules identified in the binding assay are then tested for antagonist or agonist activity in in vivo tissue culture or animal models that are well known in the art. In brief, the molecules are titrated into a plurality of cell cultures or animals and then tested for either cell/animal death or prolonged survival of the animal/cells.

In addition, the binding molecules may be complexed with toxins, e.g., ricin or cholera, or with other compounds that are toxic to cells. The toxin-binding molecule complex is then targeted to the tumor or other cell by the specificity of the binding molecule for SEQ ID NOs:3–4.

6.10 Antibodies

In general, techniques for preparing polyclonal and monoclonal antibodies as well as hybridomas capable of producing the desired antibody are well known in the art (Campbell, A. M., *Monoclonal Antibodies Technology: Laboratory Techniques in Biochemistry and Molecular Biology*, Elsevier Science Publishers, Amsterdam, The Netherlands (1984); St. Groth et al., *J. Immunol.* 35:1–21 (1990); Kohler and Milstein, *Nature* 256:495–497 (1975)), the trioma technique, the human B-cell hybridoma technique (Kozbor et al., *Immunology Today* 4:72 (1983); Cole et al., in *Monoclonal Antibodies and Cancer Therapy*, Alan R. Liss, Inc. (1985), pp. 77–96).

Any animal (mouse, rabbit, etc.) which is known to produce antibodies can be immunized with a peptide or polypeptide of the invention. Methods for immunization are well known in the art. Such methods include subcutaneous or intraperitoneal injection of the polypeptide. One skilled in the art will recognize that the amount of the protein encoded by the ORF of the present invention used for immunization will vary based on the animal which is immunized, the antigenicity of the peptide and the site of injection.

The protein which is used as an immunogen may be modified or administered in an adjuvant in order to increase the protein's antigenicity. Methods of increasing the antigenicity of a protein are well known in the art and include, but are not limited to, coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz et al., *Exp. Cell Research.* 175:109–124 (1988)).

Hybridomas secreting the desired antibodies are cloned and the class and subclass is determined using procedures known in the art (Campbell, A. M., *Monoclonal Antibody Technology: Laboratory Techniques in Biochemistry and Molecular Biology*, Elsevier Science Publishers, Amsterdam, The Netherlands (1984)).

Techniques described for the production of single chain antibodies (U.S. Pat. No. 4,946,778) can be adapted to produce single chain antibodies to proteins of the present invention.

For polyclonal antibodies, antibody containing antiserum is isolated from the immunized animal and is screened for the presence of antibodies with the desired specificity using one of the above-described procedures.

The present invention further provides the above-described antibodies in delectably labeled form. Antibodies can be delectably labeled through the use of radioisotopes, affinity labels (such as biotin, avidin, etc.), enzymatic labels (such as horseradish peroxidase, alkaline phosphatase, etc.) fluorescent labels (such as FITC or rhodamine, etc.), paramagnetic atoms, etc. Procedures for accomplishing such labeling are well-known in the art, for example, see (Sternberger, L. A. et al., *J. Histochem. Cytochem.* 18:315 (1970); Bayer, E. A. et al., *Meth. Enzym.* 62:308 (1979); Engval, E. et al., *Immunol.* 109:129 (1972); Goding, J. W. *J. Immunol. Meth.* 13:215 (1976)).

The labeled antibodies of the present invention can be used for in vitro, in vivo, and in situ assays to identify cells or tissues in which a fragment of the polypeptide of interest is expressed. The antibodies may also be used directly in therapies or other diagnostics.

The present invention further provides the above-described antibodies immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir, D. M. et al., *"Handbook of Experimental Immunology"* 4th Ed., Blackwell Scientific Publications, Oxford, England, Chapter 10 (1986); Jacoby, W. D. et al., *Meth. Enzym.* 34 Academic Press, N.Y. (1974)). The immobilized antibodies of the present invention can be used for in vitro, in vivo, and in situ assays as well as for immuno-affinity purification of the proteins of the present invention.

6.11 Computer Readable Sequences

In one application of this embodiment, a nucleotide sequence of the present invention can be recorded on computer readable media. As used herein, "computer readable media" refers to any medium which can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. A skilled artisan can readily appreciate how any of the presently known computer readable mediums can be used to create a manufacture comprising computer readable medium having recorded thereon a nucleotide sequence of the present invention.

As used herein, "recorded" refers to a process for storing information on computer readable medium. A skilled artisan can readily adopt any of the presently known methods for recording information on computer readable medium to generate manufactures comprising the nucleotide sequence information of the present invention.

A variety of data storage structures are available to a skilled artisan for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. A skilled artisan can readily adapt any number of dataprocessor structuring formats (e.g. text file or database) in order to obtain computer readable medium having recorded thereon the nucleotide sequence information of the present invention.

By providing the nucleotide sequence of SEQ ID NOs:1–2, a representative fragment thereof, or a nucleotide sequence at least 99.9% identical to SEQ ID NOs:1–2 in computer readable form, a skilled artisan can routinely access the sequence information for a variety of purposes. Computer software is publicly available which allows a skilled artisan to access sequence information provided in a computer readable medium. The examples which follow demonstrate how software which implements the BLAST (Altschul et al., *J. Mol. Biol.* 215:403–410 (1990)) and BLAZE (Brutlag et al., *Comp. Chem.* 17:203–207 (1993)) search algorithms on a Sybase system is used to identify open reading frames (ORFs) within a nucleic acid sequence. Such ORFs may be protein encoding fragments and may be useful in producing commercially important proteins such as enzymes used in fermentation reactions and in the production of commercially useful metabolites.

As used herein, "a computer-based system" refers to the hardware means, software means, and data storage means used to analyze the nucleotide sequence information of the present invention. The minimum hardware means of the computer-based systems of the present invention comprises a central processing unit (CPU), input means, output means, and data storage means. A skilled artisan can readily appreciate that any one of the currently available computer-based systems are suitable for use in the present invention.

As stated above, the computer-based systems of the present invention comprise a data storage means having stored therein a nucleotide sequence of the present invention and the necessary hardware means and software means for supporting and implementing a search means. As used herein, "data storage means" refers to memory which can store nucleotide sequence information of the present invention, or a memory access means which can access manufactures having recorded thereon the nucleotide sequence information of the present invention.

As used herein, "search means" refers to one or more programs which are implemented on the computer-based system to compare a target sequence or target structural motif with the sequence information stored within the data storage means. Search means are used to identify fragments or regions of a known sequence which match a particular target sequence or target motif. A variety of known algorithms are disclosed publicly and a variety of commercially available software for conducting search means are and can be used in the computer-based systems of the present invention. Examples of such software includes, but is not limited to, MacPattern (EMBL), BLASTN and BLASTA (NPOLYPEPTIDEIA). A skilled artisan can readily recognize that any one of the available algorithms or implementing software packages for conducting homology searches can be adapted for use in the present computer-based systems.

As used herein, a "target sequence" can be any nucleic acid or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that searches for commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

6.12 Expression Modulating Sequences

EMF sequences can be identified within a genome by their proximity to the ORFs. An intergenic segment, or a fragment of the intergenic segment, from about 10 to 200 nucleotides in length, taken 5' from any ORF will modulate the expression of an operably linked 3' ORF in a fashion similar to that found with the naturally linked ORF sequence. As used herein, an "intergenic segment" refers to the fragments of a genome which are between two ORF(S) herein described. Alternatively, EMFs can be identified using known EMFs as a target sequence or target motif in the computer-based systems of the present invention.

The presence and activity of an EMF can be confirmed using an EMF trap vector. An EMF trap vector contains a cloning site 5' to a marker sequence. A marker sequence encodes an identifiable phenotype, such as antibiotic resistance or a complementing nutrition auxotrophic factor, which can be identified or assayed when the EMF trap vector is placed within an appropriate host under appropriate conditions. As described above, an EMF, will modulate the expression of an operably linked marker sequence. A more detailed discussion of various marker sequences is provided below.

A sequence which is suspected as being an EMF is cloned in all three reading frames in one or more restriction sites upstream from the marker sequence in the EMF trap vector. The vector is then transformed into an appropriate host using known procedures and the phenotype of the transformed host is examined under appropriate conditions. As described above, an EMF will modulate the expression of an operably linked marker sequence.

6.13 Triplex Helix Formation

In addition, the fragments of the present invention, as broadly described, can be used to control gene expression through triple helix formation or antisense DNA or RNA, both of which methods are based on the binding of a polynucleotide sequence to DNA or RNA. Polynucleotides suitable for use in these methods are usually 20 to 40 bases in length and are designed to be complementary to a region of the gene involved in transcription (triple helix-see Lee et al., *Nucl. Acids Res.* 6:3073 (1979); Cooney et al., *Science* 15241:456 (1988); and Dervan et al., *Science* 251:1360 (1991)) or to the mRNA itself (antisense-Olmno, *J. Neurochem.* 56:560 (1991); *Oligodeoxynucleotides as Antisense Inhibitors of Gene Expression,* CRC Press, Boca Raton, Fla. (1988)).

Triple helix-formation optimally results in a shut-off of RNA transcription from DNA, while antisense RNA hybridization blocks translation of an mRNA molecule into polypeptide. Both techniques have been demonstrated to be effective in model systems. Information contained in the sequences of the present invention is necessary for the design of an antisense or triple helix oligonucleotide.

6.14 Diagnostics Assays and Kits

The present invention further provides methods to identify the expression of one of the ORFs of the present invention, or homolog thereof, in a test sample, using a nucleic acid probe or antibodies of the present invention.

In detail, such methods comprise incubating a test sample with one or more of the antibodies or one or more of nucleic acid probes of the present invention and assaying for binding of the nucleic acid probes or antibodies to components within the test sample.

Conditions for incubating a nucleic acid probe or antibody with a test sample vary. Incubation conditions depend on the format employed in the assay, the detection methods employed, and the type and nature of the nucleic acid probe or antibody used in the assay. One skilled in the art will recognize that any one of the commonly available hybridization, amplification or immunological assay formats can readily be adapted to employ the nucleic acid probes or antibodies of the present invention. Examples of such assays can be found in Chard, T., *An Introduction to Radioimmunoassay and Related Techniques,* Elsevier Science Publishers, Amsterdam, The Netherlands (1986); Bullock, G. R. et al., *Techniques in Immunocytochemistry,* Academic Press, Orlando, Fla. Vol. 1 (1982), Vol. 2 (1983), Vol. 3 (1985); Tijssen, P., *Practice and Theory of immunoassays: Laboratory Techniques in Biochemistry and Molecular Biology,* Elsevier Science Publishers, Amsterdam, The Netherlands (1985).

The test samples of the present invention include cells, protein or membrane extracts of cells, or biological fluids such as sputum, blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily adapted in order to obtain a sample which is compatible with the system utilized.

In another embodiment of the present invention, kits are provided which contain the necessary reagents to carry out the assays of the present invention.

Specifically, the invention provides a compartment kit to receive, in close confinement, one or more containers which comprises: (a) a first container comprising one of the probes or antibodies of the present invention; and (b) one or more other containers comprising one or more of the following: wash reagents, reagents capable of detecting presence of a bound probe or antibody.

In detail, a compartment kit includes any kit in which reagents are contained in separate containers. Such containers include small glass containers, plastic containers or strips of plastic or paper. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the antibodies used in the assay, containers which contain wash reagents (such as phosphate buffered saline, Tris-buffers, etc.), and containers which contain the reagents used to detect the bound antibody or probe.

Types of detection reagents include labeled nucleic acid probes, labeled secondary antibodies, or in the alternative, if the primary antibody is labeled, the enzymatic, or antibody binding reagents which are capable of reacting with the labeled antibody. One skilled in the art will readily recognize that the disclosed probes and antibodies of the present invention can be readily incorporated into one of the established kit formats which are well known in the art.

6.15 Screening Assays

Using the isolated proteins of the present invention, the present invention further provides methods of obtaining and identifying agents which bind to a protein encoded by one of the ORFs from a nucleic acid with a sequence of one of SEQ ID NOs:1–2, or to a nucleic acid with a sequence of one of SEQ ID NOs:1–2.

In detail, said method comprises the steps of:
(a) contacting an agent with an isolated protein encoded by one of the ORFs of the present invention, or nucleic acid of the invention; and
(b) determining whether the agent binds to said protein or said nucleic acid.

The agents screened in the above assay can be, but are not limited to, peptides, carbohydrates, vitamin derivatives, or other pharmaceutical agents. The agents can be selected and screened at random or rationally selected or designed using protein modeling techniques.

For random screening, agents such as peptides, carbohydrates, pharmaceutical agents and the like are selected at random and are assayed for their ability to bind to the protein encoded by the ORF of the present invention.

Alternatively, agents may be rationally selected or designed. As used herein, an agent is said to be "rationally selected or designed" when the agent is chosen based on the configuration of the particular protein. For example, one skilled in the art can readily adapt currently available procedures to generate peptides, pharmaceutical agents and the like capable of binding to a specific peptide sequence in order to generate rationally designed antipeptide peptides, for example see Hurby et al., Application of Synthetic Peptides: Antisense Peptides," In *Synthetic Peptides, A User's Guide,* W.H. Freeman, NY (1992), pp. 289–307, and Kaspczak et al., *Biochemistry* 28:9230–8 (1989), or pharmaceutical agents, or the like.

In addition to the foregoing, one class of agents of the present invention, as broadly described, can be used to control gene expression through binding to one of the ORFs or EMFs of the present invention. As described above, such agents can be randomly screened or rationally designed/selected. Targeting the ORF or FMF allows a skilled artisan to design sequence specific or element specific agents, modulating the expression of either a single ORF or multiple ORFs which rely on the same EMF for expression control.

One class of DNA binding agents are agents which contain base residues which hybridize or form a triple helix formation by binding to DNA or RNA. Such agents can be based on the classic phosphodiester, ribonucleic acid backbone, or can be a variety of sulfhydryl or polymeric derivatives which have base attachment capacity.

Agents suitable for use in these methods usually contain 20 to 40 bases and are designed to be complementary to a region of the gene involved in transcription (triple helix-see Lee et al., *Nucl. Acids Res.* 6:3073 (1979); Cooney et al., *Science* 241:456 (1988); and Dervan et al., *Science*

251:1360 (1991)) or to the mRNA itself (antisense—Okano, J. Neurochem. 56:560 (1991); Oligodeoxynucleotides as Antisense Inhibitors of Gene Expression, CRC Press, Boca Raton, Fla. (1988)). Triple helix-formation optimally results in a shut-off of RNA transcription from DNA, while antisense RNA hybridization blocks translation of an mRNA molecule into polypeptide. Both techniques have been demonstrated to be effective in model systems. Information contained in the sequences of the present invention is necessary for the design of an antisense or triple helix oligonucleotide and other DNA binding agents.

Agents which bind to a protein encoded by one of the ORFs of the present invention can be used as a diagnostic agent, in the control of bacterial infection by modulating the activity of the protein encoded by the ORF. Agents which bind to a protein encoded by one of the ORFs of the present invention can be formulated using known techniques to generate a pharmaceutical composition.

6.16 Use of Nucleic Acids as Probes

Another aspect of the subject invention is to provide for polypeptide-specific nucleic acid hybridization probes capable of hybridizing with naturally occurring nucleotide sequences. The hybridization probes of the subject invention may be derived from the nucleotide sequence of the SEQ ID NOs:1–2.

PCR as described U.S. Pat. Nos. 4,683,195 and 4,965,188 provides additional uses for oligonucleotides based upon the nucleotide sequences. Such probes used in PCR may be of recombinant origin, may be chemically synthesized, or a mixture of both. The probe will comprise a discrete nucleotide sequence for the detection of identical sequences or a degenerate pool of possible sequences for identification of closely related genomic sequences.

Other means for producing specific hybridization probes for nucleic acids include the cloning of nucleic acid sequences into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

The nucleotide sequences may be used to construct hybridization probes for mapping their respective genomic sequences. The nucleotide sequence provided herein may be mapped to a chromosome or specific regions of a chromosome using well known genetic and/or chromosomal mapping techniques. These techniques include in situ hybridization, linkage analysis against known chromosomal markers, hybridization screening with libraries or flow-sorted chromosomal preparations specific to known chromosomes, and the like. The technique of fluorescent in situ hybridization of chromosome spreads has been described, among other places, in Verma et al (1988) Human Chromosomes: A Manual of Basic Techniques, Pergamon Press, New York N.Y.

Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of a nucleic acid on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

The nucleotide sequence may be used to produce purified polypeptides using well known methods of recombinant DNA technology. Among the many publications that teach methods for the expression of genes after they have been isolated is Goeddel (1990) Gene Expression Technology, Methods and Enzymology, Vol 185, Academic Press, San Diego. Polypeptides may be expressed in a variety of host cells, either prokaryotic or eukaryotic. Host cells may be from the same species from which a particular polypeptide nucleotide sequence was isolated or from a different species. Advantages of producing polypeptides by recombinant DNA technology include obtaining adequate amounts of the protein for purification and the availability of simplified purification procedures.

Each sequence so obtained was compared to sequences in GenBank using a search algorithm developed by Applied Biosystems and incorporated into the INHERIT™ 670 Sequence Analysis System. In this algorithm, Pattern Specification Language (developed by TRW Inc., Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

Alternatively, BLAST, which stands for Basic Local Alignment Search Tool, is used to search for local sequence alignments (Altschul S F (1993) J Mol Evol 36:290–300; Altschul, S F et al (1990) J Mol Biol 215:403–10). BLAST produces alignments of both nucleotide and amino acid sequences to determine sequence similarity. Because of the local nature of the alignments, BLAST is especially useful in determining exact matches or in identifying homologs. Whereas it is ideal for matches which do not contain gaps, it is inappropriate for performing motif-style searching. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

In addition, BLAST analysis was used to search for related molecules within the libraries of the LIFESEQ™ database. This process, an "electronic northern" analysis is analogous to northern blot analysis in that it uses one cellubrevin sequence at a time to search for identical or homologous molecules at a set stringency. The stringency of the electronic northern is based on "product score". The product score is defined as (% nucleotide or amino acid [between the query and reference sequences] in Blast multiplied by the % maximum possible BLAST score [based on the lengths of query and reference sequences]) divided by 100. At a product score of 40, the match will be exact within a 1–2% error; and at 70, the match will be exact. Homologous or related molecules can be identified by selecting those which show product scores between approximately 15 and 30.

6.17 SEQ ID NOs:1–3

Referring to FIG. 1, SEQ ID NO:1 is the nucleotide sequence of an expressed sequence tag corresponding to a polynucleotide isolated from a cDNA library of human fetal liver. SEQ ID NO:2 is an extended version of SEQ ID NO:1 obtained as described in Example 33. SEQ ID NO:2 encodes a polypeptide having the amino acid sequence of SEQ ID NO:3 (shown in FIG. 2). Protein database searches with the BLAST algorithm aligns SEQ ID NO 3 with interleukin-8receptor (IL-8R) family members. The level of homology between SEQ ID NO:3 and IL-8R family members is consistent with that between other members of this family, i.e., on the order of about 25% identical amino acids between family members. In particular, FIG. 3 shows the amino-acid alignment between SEQ ID NO:3 and IL-8R type II (SEQ ID NO:4) indicating that 87 out of 333 amino acid residues are identical (26% identical). SEQ ID NO:3 also has 28% identity with another member of this family, the IL-8 related receptor. The IL-8 related receptor has been shown to bind IL-8, and is 26% identical at the amino acid level to IL-8R type II (SEQ ID NO:4).

The IL-8R type II (SEQ ID NO:4) is is a 7-transmembrane G protein-coupled receptor. FIG. 4 presents the hydrophilicity profiles of both SEQ ID NO:3 and IL-8R type II (SEQ ID NO:4), which aligns hydrophobic sequences that correspond to transmembrane domains. The alignment shows a striking correspondence of the spacing of the transmembrane domains between the two proteins. Thus, SEQ ID NO:3 is structurally homologous to IL-8R type II (SEQ ID NO:4) in addition to sharing 26% amino acid sequence identity. These data indicate that SEQ ID NO:3 is a member of the IL-8R gene family, i.e., a C-X-C chemokine receptor, and more generally, a member of the 7-transmembrane receptor family.

A highly conserved region that is known to be critical for the signalling functions of G protein-coupled receptors is located at the second intracellular loop between the third and fourth transmembrane domains (Ballesteros, J. et al., 1998, J. Biol. Chem., 273, 10445–10453). This sequence is shown for the IL-8R type II in FIG. 5 (SEQ ID NO:6), together with the corresponding sequence in SEQ ID NO:3 (SEQ ID NO:5). FIGS. 3 and 5 demonstrate that the sequence between the third and fourth hydrophobic domains of SEQ ID NO:3 aligns well with the conserved region in IL-8R type II (SEQ ID NO:6).

Phosphorylation events in the carboxyl terminal domain of G protein-coupled receptors are involved in the desensitization of these receptors. The in vivo phosphorylation sites of IL-8R type II been identified in a region containing a triplet of serines (SEQ ID NO:7). The phosphorylation occurs on the outer two serines while the middle serine is not phosphorylated (FIG. 6) (Schraufstatter, I. U. et al., 1998, Biochem. Biophys. Res. Comm., 244, 243–248). Deletion of the sequence indicated in FIG. 6 specifically affects the ability of the IL-8R type II (SEQ ID NO:4) to desensitize but not other functions like G protein coupling, calcium mobilization and receptor internalization. A similar triplet of serines is also present on the carboxyl terminus of SEQ ID NO:3 (SEQ ID NO:8, FIG. 6), indicating that SEQ ID NO:3 contains phosphorylation sites that mediate desensitization.

The message encoding SEQ ID NO:3 is regulated in a tissue-specific manner. An expression study using a semi-quantatative PCR/Southern blot approach revealed a significant level of expression in macrophage and fetal liver. This expression profile implicates the gene as a developmental regulator or a regulator of a later stage of hematopoesis from this tissue.

6.18 Uses of Chemokine Receptor Polypeptides and Antibodies

Chemokines are potent stimulants of neutrophils causing rapid shape change, chemotaxis, respiratory bursts, and degranulation. Chemokines are also known to be potent chemoattractants for a variety of blood cell components, including monocytes, basophils, eosinophils, and lymphocytes, particularly T-lymphocytes. The polypeptides of the invention can be used to detect the presence of a chemokine in a sample. More specifically, a polypeptide of the invention that is capable of binding to a chemokine, such as IL-8 or a related ligand, can be labeled with a detectable label and contacted with the sample under conditions suitable for binding of the polypeptide to the chemokine. Bound label is then detected as an indication of the presence of the chemokine. For example, polypeptides of the invention can be used to monitor chemokine release at sites of infection or inflammation. The established correlation between chemokine expression and inflammatory conditions and disease states indicates that the polypeptides of the invention can used as diagnostic and prognostic indicators of such conditions. For example, the polypeptides and antibodies of the invention are useful in methods for screening patients with certain myelogenous leukemias as well as other hyperproliferative blood diseases.

Polypeptides of the invention that are capable of binding to a chemokine are also useful in modulating chemokine effects, e.g., inflammatory and immune responses. The polypeptides can be administered to the site of an inflammatory or immune response mediated by an IL-8-like chemokine, for example, such that the polypeptides compete with the corresponding native cell surface receptors for binding to the chemokine, thereby inhibiting chemokine action. The inhibition of pro-inflammatory effects of chemokines is useful in treating pathological conditions caused by the inflammatory response.

The polypeptides of the invention are also useful for making antibody substances that are specifically immunoreactive with chemokines. Antibodies and portions thereof (e.g., Fab fragments) which bind to the chemokines of the invention can act as chemokine agonists or antagonists. Chemokine agonist and antagonist antibodies can be used therapeutically, provided that such antibodies are sufficiently non-immunogenic. A variety of methods are available to reduce the immunogenicity of therapeutic proteins, such as, for example, conjugation to one or more molecules such as a polyalkylene glycol (e.g., polyethylene glycol). For administrations to humans, humanized or fully human antibodies are typically employed.

Chemokines promote the healing of wounds and accelerate recovery from conditions where inflammation is important to eradication of infection, such as, for example, pneumonia. Thus, the chemokine agonist antibodies of the invention are useful in promoting wound healing and recovery from such conditions.

As chemokines have also been shown to regulate proliferation and/or differentiation of hematopoietic stem and progenitor cells in vitro and in vivo, chemokine agonist antibodies are also useful in methods of treating neutropenia caused by, for example, chemotherapy-or radiation treatments. For example, chemokine agonist antibodies can be administered as adjunctive agents before and/or during chemotherapy or radiation therapy to protect myeloid progenitor cells from the cytotoxic effects of the chemotherapeutic agents or radiation. The agonist antibodies place myeloid cells into a myeloprotected, slow-cycling state, thereby inhibiting or decreasing cell damage that could otherwise be caused by cell-cycle active chemotherapy drugs such as cytosine arabinoside, 5-fluorouracil, or hydroxyurea. Treatment with chemokine agonist antibodies of the invention permits the administration of high doses of chemotherapeutics that would, in the absence of agonist antibody treatment, compromise the ability of the patient to generate mature functional blood cells. In addition, chemokine agonist antibodies can be used to prevent myeloid progenitor cells from becoming leukemic as the result of the administration of chemotherapeutic agents.

Chemokine agonist antibodies according to the invention are also useful for inhibiting hyperproliferative myeloid-based diseases such as chronic myelogenous leukemia, polycythemia vera, and hypernegakaryocytopoietic disorders. Hyperproliferative states in such disorders occur because the progenitor cells are unable to negatively regulate cell growth and replication. Administration of chemokine agonist antibodies inhibits cell replication, thereby reducing abnormal cell growth.

Chemokine antagonist antibodies can be used as described above for chemokine-binding polypeptides of the invention.

The polypeptides and antibodies of the invention are administered by any route that delivers an effective dosage to the desired site of action. The determination of a suitable route of administration and an effective dosage for a particular indication is within the level of skill in the art. In vivo murine studies with IL-8M1 have shown that effective suppression of progenitor cell proliferation occurs at dosages of approximately 10.0 to 0.01 μg per animal, although 1.0 to 0.01 μg per animal is preferred. Guitable dosage ranges for the polypeptides and antibodies of the invention can be extrapolated from these dosages or from similar studies in appropriate animal models. Dosages can then be adjusted as necessary by the clinician to provide maximal therapeutic benefit.

The chemokine receptor polypeptides of the invention are also useful for screening compounds for the ability to bind to one or more chemokine receptors. Binding assays can be carried out in any of a variety of formats, e.g., competitive or non-competitive, with the polypeptides free in solution, affixed to a solid support, borne on a cell surface or located intracellularly. One screening method utilizes eukaryotic or prokaryotic host cells which are stably transformed with recombinant nucleic acids expressing the chemokine receptor polypeptide. Compounds are screened against such transformed cells (either in viable or fixed form) in standard binding assays.

The present invention is illustrated in the following examples. Upon consideration of the present disclosure, one of skill in the art will appreciate that many other embodiments and variations may be made in the scope of the present invention. Accordingly, it is intended that the broader aspects of the present invention not be limited to the disclosure of the following examples.

EXAMPLE 1

Preparation of a Universal Set of Probes

Two types of universal sets of probes may be prepared. The first is a complete set (or at least a noncomplementary subset) of relatively short probes, for example all 4096 (or about 2000 non-complementary) 6-mers, or all 16,384 (or about 8,000 non-complementary) 7-mers. Full noncomplementary subsets of 8-mers and longer probes are less convenient inasmuch as they include 32,000 or more probes.

A second type of probe set is selected as a small subset of probes still sufficient for reading every bp in any sequence with at least with one probe. For example, 12 of 16 dimers are sufficient. A small subset for 7-mers, 8-mer and 9-mers for sequencing double stranded DNA may be about 3000, 10,000 and 30,000 probes, respectively.

Probes may be prepared using standard chemistry with one to three non-specified (mixed A,T,C and G) or universal (e.g. M base or inosine) bases at the ends. If radiolabelling is used, probes may have an OH group at the 5' end for kinasing by radiolabeled phosphorous groups. Alternatively, probes labeled with any compatible system, such as fluorescent dyes, may be employed. Other types of probes, such as PNA (Protein Nucleic Acids)or probes containing modified bases which change duplex stability also may be used.

Probes may be stored in bar-coded multiwell plates. For small numbers of probes, 96-well plates may be used; for 10,000 or more probes, storage in 384- or 864-well plates is preferred. Stacks of 5 to 50 plates are enough to store all probes. Approximately 5 pg of a probe may be sufficient for hybridization with one DNA sample. Thus, from a small synthesis of about 50 mg per probe, ten million samples may be analyzed. If each probe is used for every third sample, and if each sample is 1000 bp in length, then over 30 billion bases (10 human genomes) may be sequenced by a set of 5,000 probes.

EXAMPLE 2

Probes Having Modified Oligonucleotides

Modified oligonucleotides may be introduced into hybridization probes and used under appropriate conditions therefor. For example, pyrimidines with a halogen at the $C^5$-position may be used to improve duplex stability by influencing base stacking. 2,6-diaminopurine may be used to provide a third hydrogen bond in base pairing with thymnine, thereby thermally stabilizing DNA-duplexes. Using 2,5-diaminopurine may increase duplex stability to allow more stringent conditions for annealing, thereby improving the specificity of duplex formation, suppressing background problems and permitting the use of shorter oligomers.

The synthesis of the triphosphate versions of these modified nucleotides is disclosed by Hoheisel & Lehrach (1990).

One may also use the non-discriminatory base analogue, or universal base, as designed by Nichols et al. (1994). This new analogue, 1-(2-deoxy- -D-ribfuranosyl)-3-nitropyrrole (designated M), was generated for use in oligonucleotide probes and primers for solving the design problems that arise as a result of the degeneracy of the genetic code, or when only fragmentary peptide sequence data are available. This analogue maximizes stacking while minimizing hydrogen-bonding interactions without sterically disrupting a DNA duplex.

The M nucleoside analogue was designed to maximize stacking interactions using aprotic polar substituents linked to heteroaromatic rings, enhancing intra- and inter-stand stacking interactions to lessen the role of hydrogen bonding in base-pairing specificity. Nichols et al. (1994) favored 3-nitropyrrole 2-deoxyribonucleoside because of its structural and electronic resemblance to p-nitroaniline, whose derivatives are among the smallest known intercaltors of double-stranded DNA.

The dimethoxytrityl-protected phosphoramidite of nucleoside M is also available for incorporation into nucleotides used as primers for sequencing and polymerase chain reaction (PCR). Nichols et al. (1994) showed that a substantial number of nucleotides can be replaced by M without loss of primer specificity.

A unique property of M is its ability to replace long strings of contiguous nucleosides and still yield functional sequencing primers. Sequences with three, six and nine M substitutions have all been reported to give readable sequencing ladders, and PCR with three different M-containing primers all resulted in amplification of the correct product (Nichols et al., 1994).

The ability of 3-nitropyrrole-containing oligonucleotides to function as primers strongly suggests that a duplex structure must form with complementary strands. Optical thermal profiles obtained for the oligonucleotide pairs d(5-$C_2$-$T_5XT_5G_2$-3) (SEQ ID NO:9) and d(5-$C_2A_5YA_5G2$-3) (SEQ ID NO:10) (where X and Y can be A, C, G, T or M) were reported to fit the normal sigmoidal pattern observed for the DNA double-to single strand transition. The Tm values of the oligonucleotides containing X M base pairs (where X was A, C, G or T, and Y was M) were reported to all fall within a 3° C. range (Nichols et al., 1994).

EXAMPLE 3

Selection and Labeling of Probes

When an array of subarrays is produced, the sets of probes to be hybridized in each of the hybridization cycles on each of the subarrays is defined. For example, a set of 384 probes may be selected from the universal set, and 96 probings may be performed in each of 4 cycles. Probes selected to be hybridized in one cycle preferably have similar G+C contents.

Selected probes for each cycle are transferred to a 96-well plate and then are labeled by kinasing or by other labelling procedures if they are not labeled (e.g. with stable fluorescent dyes) before they are stored.

On the basis of the first round of hybridizations, a new set of probes may be defined for each of the subarrays for additional cycles. Some of the arrays may not be used in some of the cycles. For example, if only 8 of 64 patient samples exhibit a mutation and 8 probes are scored first for each mutation, then all 64 probes may be scored in one cycle and 32 subarrays are not used. These unused subarrays may then be treated with hybridization buffer to prevent drying of the filters.

Probes may be retrieved from the storing plates by any convenient approach, such as a single channel pipetting device, or a robotic station, such as a Beckman Biomek 1000 (Beckman Instruments, Fullerton, Calif.) or a Mega Two robot (Megamation, Lawrenceville, N.J.). A robotic station may be integrated with data analysis programs and probe managing programs. Outputs of these programs may be inputs for one or more robotic stations.

Probes may be retrieved one by one and added to subarrays covered by hybridization buffer. It is preferred that retrieved probes be placed in a new plate and labeled or mixed with hybridization buffer. The preferred method of retrieval is by accessing stored plates one by one and pipetting (or transferring by metal pins) a sufficient amount of each selected probe from each plate to specific wells in an intermediary plate. An array of individually addressable pipettes or pins may be used to speed up the retrieval process.

EXAMPLE 4

Preparation of Labeled Probes

The oligonucleotide probes may be prepared by automated synthesis, which is routine to those of skill in the art, for example, using an Applied Biosystems system. Alternatively, probes may be prepared using Genosys Biotechnologies Inc. Methods using stacks of porous Teflon wafers.

Oligonucleotide probes may be labeled with, for example, radioactive labels ($^{35}S$, $^{32}P$, $^{33}P$, and preferably, $^{33}P$) for arrays with 100–200 um or 100–400 um spots; non-radioactive isotopes (Jacobsen et al., 1990); or fluorophores (Brumbaugh et al., 1988). All such labeling methods are routine in the art, as exemplified by the relevant sections in Sambrook et al. (1989) and by further references such as Schubert et al. (1990), Murakami et al. (1991) and Cate et al. (1991), all articles being specifically incorporated herein by reference.

In regard to radiolabelling, the common methods are end-labeling using T4 polynucleotide kinase or high specific activity labeling using Klenow or even T7 polymerase. These are described as follows.

Synthetic oligonucleotides are synthesized without a phosphate group at their 5 termini and are therefore easily labeled by transfer of the $-^{32}P$ or $-^{33}P$ from [$-^{32}P$]ATP or [$-^{33}P$]ATP using the enzyme bacteriophage T4 polynucleotide kinase. If the reaction is carried out efficiently, the specificity activity of such probes can be as high as the specific activity of the [$-^{32}P$]ATP or [$-^{33}P$]ATP itself. The reaction described below is designed to label 10 pmoles of an oligonucleotide to high specific activity. Labeling of different amounts of oligonucleotide can easily be achieved by increasing or decreasing the size of the reaction, keeping the concentrations of all components constant.

A reaction mixture would be created using 1.0 ul of oligonucleotide (10 pmoles/ul); 2.0 ul of 10×bacteriophage T4 polynucleotide kinase buffer; 5.0 ul of [$-^{32}P$]ATP or [$-^{33}P$]ATP (sp. Act. 5000 Ci/mmole; 10 mCi/ml in aqueous solution) (10 pmoles); and 11.4 ul of water. Eight (8) units (~1 ul) of bacteriophage T4 polynucleotide kinase is added to the reaction mixture mixed well, and incubated for 45 minutes at 37° C. The reaction is heated for 10 minutes at 68° C. to inactivate the bacteriophage T4 polynucleotide kinase.

The efficiency of transfer of $^{32}P$ or $^{33}P$ to the oligonucleotide and its specific activity is then determined. If the specific activity of the probe is acceptable, it is purified. If the specific activity is too low, an additional 8 units of enzyme is added and incubated for a further 30 minutes at 37° C. before heating the reaction for 10 minutes at 68° C. to inactivate the enzyme.

Purification of radiolabeled oligonucleotides can be achieved by precipitation with ethanol; precipitation with cetylpyridinium bromide; by chromatography through bio-gel P-60; or by chromatography on a Sep-Pak $C_{18}$ column.

Probes of higher specific activities can be obtained using the Klenow fragment of E. coli. DNA polymerase I to synthesize a strand of DNA complementary to the synthetic oligonucleotide. A short primer is hybridized to an oligonucleotide template whose sequence is the complement of the desired radiolabeled probe. The primer is then extended using the Klenow fragment of E. coli DNA polymerase I to incorporate [-$^{32}$P] dNTPs or [-$^{33}$P] dNTPs in a template-directed manner. After the reaction, the template and product are separated by denaturation followed by electrophoresis through a polyacrylamide gel under denaturing conditions. With this method, it is possible to generate oligonucleotide probes that contain several radioactive atoms per molecule of oligonucleotide, if desired.

To use this method, one would mix in a microfuge tube the calculated amounts of [a-32P]dNTPs or [a-33P]dNTPs necessary to achieve the desired specific activity and sufficient to allow complete synthesis of all template strands. The concentration of dNTPs should not be less than 1 uM at any stage during the reaction. Then add to the tube the appropriate amounts of primer and template DNAs, with the primer being in three-to tenfold molar excess over the template.

0.1 volume of 10×Klenow buffer would then be added and mixed well. 2–4 units of the Klenow fragment of E. coli DNA polymerase I would then be added per 5 ul of reaction volume, mixed and incubated for 2–3 hours at 4° C. If desired, the process of the reaction may be monitored by removing small (0.1 ul) aliquots and measuring the proportion of radioactivity that has become precipitable with 10% trichloroacetic acid (TCA).

The reaction would be diluted with an equal volume of gel-loading buffer, heated to 80° C. for 3 minutes, and then the entire sample loaded on a denaturing polyacrylamide gel. Following electrophoresis, the gel is autoradiographed, allowing the probe to be localized and removed from the gel. Various methods for fluorphobic labeling are also available, as follows. Brumbaugh et al. (1988) describe the synthesis of fluorescently labeled primers. A deoxyuridine analog with a primary amine "linker arm" of 12 atoms attached at C-5 is synthesized. Synthesis of the analog consists of derivatizing 2-deoxyuridine through organometallic intermediates to give 5 (methyl propenoyl)-2-deoxyuridine. Reaction with dimethoxytrityl-chloride produces the corresponding 5-dimethoxytrityl adduct. The methyl ester is hydrolyzed, activated, and reacted with an appropriately monoacylated alkyl diamine. After purification, the resultant linker arm nucleosides are converted to nucleoside analogs suitable for chemical oligonucleotide synthesis.

Oligonucleotides would then be made that include one or two linker arm bases by using modified phosphoridite chemistry. To a solution of 50 nmol of the linker arm oligonucleotide in 25 ul of 500 mM sodium biocarbonate (pH 9.4) is added 20 ul of 300 mM FITC in dimethyl sulfoxide. The mixture is agitated at room temperature for 6 hrs. The oligonucleotide is separated from free FITC by elution form a 1×30 cm Sephadex G-25 column with 20 mM ammonium acetate (pH 6), combining fractions in the first UV-absorbing peak.

In general, fluorescent labeling of an oligonucleotide at it s 5-end initially involved two steps. First, a N-protected aminoalkyl phosphoramidite derivative is added to the 5-end of an oligonucleotide during automated DNA synthesis. After removal of all protecting groups, the NHS ester of an appropriate fluorescent dye is coupled to the 5-amino group overnight followed by purification of the labeled oligonucleotide from the excess of dye using reverse phase HPLC or PAGE.

Schubert et al. (1990) described the synthesis of a phosphoramidite that enables oligonucleotides labeled with fluorescein to be produced during automated DNA synthesis.

Murakami et al. also described the preparation of flurescein-labeled oligonucleotides.

Cate et al. (1991) describe the use of oligonucleotide probes directly conjugated to alkaline phosphatase in combination with a direct chemiluminescent substrate (AMPPD) to allow probe detection.

Labeled probes could readily be purchased form a variety of commercial sources, including GENSET, rather then synthesized.

Other labels include ligands which can serve as specific binding members to a labeled antibody, chemiluminesceis, enzymes, antibodies which can serve as a specific binding pair member for a labeled ligand and the like. A wide variety of labels have been employed in immunoassays which can readily be employed. Still other labels include antigens, groups with specific reactivity, and electrochemically detectable moeities.

In general, labeling of nucleic acids with electrophore mass labels ("EML") is described, for example, in Xu et al., J. Chromatography 764:95–102 (1997). Electrophores are compounds that can be detected with high sensitivity by electron capture mass spectrometry (EC-MS). EMLs can be attached to a probe using chemistry that is well known in the art for reversibly modifying a nucleotide (e.g., well known nucleotide synthesis chemistry teaches a variety of methods for attaching molecules to nucleotides as protecting groups). EMLs are detected using a variety of well known electron capture mass spectrometry devices (e.g., devices sold by Finnigan Corporation). Further, techniques that may be used in the detection of EMLs include, for example, fast atomic bombardment mass spectrometry (see, e.g., Koster et al., Biomedical Environ. Mass Spec. 14:111–116 (1987)); plasma desorption mass spectrometry; electrospray/ionspray (see, e.g., Fenn et al., J. Phys. Chem. 88:4451–59 (1984), PCT Appln. No. WO 90/14148, Smith et al., Anal. Chem. 62:882–89 (1990)); and matrix-assisted laser desorption/ionization (Hillenkamp, et al., "Matrix Assisted UV-Laser Desorption/Ionization: A New Approach to Mass Spectrometry of Large Biomolecules," *Biological Mass Spectrometry* (Burlingame and McCloskey, eds.), Elsevier Science Publishers, Amsterdam, pp. 49–60, 1990); Huth-Fehre et al., "Matrix Assisted Laser Desorption Mass Spectrometry of Oligodeoxythymidylic Acids," *Rapid Communications in Mass Spectrometry,* 6:209–13 (1992)).

In preferred embodiments, the EMLs are attached to a probe by a covalent bond that is light sensitive. The EML is released from the probe after hybridization with a target nucleic acid by a laser or other light source emitting the desired wavelength of light. The EML is then fed into a GC-MS (gas chromatogrph-mass spectrometer) or other appropiate device, and identified by its mass.

EXAMPLE 5

Preparation of Sequencing Chips and Arrays

A basic example is using 6-mers attached to 50 micron surfaces to give a chip with dimensions of 3×3 mm which can be combined to give an array of 20×20 cm. Another example is using 9-mer oligonucleotides attached to 10×10 microns surface to create a 9-mer chip, with dimensions of 5×5 mm. 4000 units of such chips may be used to create a 30×30 cm array. In an array in which 4,000 to 16,000 oligochips are arranged into a square array. A plate, or collection of tubes, as also depicted, may be packaged with the array as part of the sequencing kit.

The arrays may be separated physically from each other or by hydrophobic surfaces. One possible way to utilize the hydrophobic strip separation is to use technology such as the Iso-Grid Microbiology System produced by QA Laboratories, Toronto, Canada.

Hydrophobic grid membrane filters (HGMF) have been in use in analytical food microbiology for about a decade where they exhibit unique attractions of extended numerical range and automated counting of colonies. One commercially-available grid is ISO-GRID™ from QA Laboratories Ltd. (Toronto, Canada) which consists of a square (60×60 cm) of polysulfone polymer (Gelman Tuffryn HT-450, 0.45 u pore size) on which is printed a black hydrophobic ink grid consisting of 1600 (40×40) square cells. HGMF have previously been inoculated with bacterial suspensions by vacuum filtration and incubated on the differential or selective media of choice.

Because the microbial growth is confined to grid cells of known position and size on the membrane, the HGMF functions more like an MPN apparatus than a conventional plate or membrane filter. Peterkin et al. (1987) reported that these HGMFs can be used to propagate and store genomic libraries when used with a HGMF replicator. One such instrument replicates growth from each of the 1600 cells of the ISO-GRID and enables many copies of the master HGMF to be made (Peterkin et al., 1987).

Sharpe et al., (1989) also used ISO-GRID HGMF form QA Laboratories and an automated HGMF counter (MI-100 Interpreter) and RP-100 Replicator. They reported a technique for maintaining and screening many microbial cultures.

Peterkin and colleagues later described a method for screening DNA probes using the hydrophobic grid-membrane filter (Peterkin et al., 1989). These authors reported methods for effective colony hybridization directly on HGMFs. Previously, poor results had been obtained due to the low DNA binding capacity of the epoxysulfone polymer on which the HGMFs are printed. However, Peterkin et al. (1989) reported that the binding of DNA to the surface of the membrane was improved by treating the replicated and incubated HGMF with polyethyleneimine, a polycation, prior to contact with DNA. Although this early work uses cellular DNA attachment, and has a different objective to the present invention, the methodology described may be readily adapted for Format 3 SBH.

In order to identify useful sequences rapidly, Peterkin et al. (1989) used radiolabeled plasmid DNA from various clones and tested its specificity against the DNA on the prepared HGMFs. In this way, DNA from recombinant plasmids was rapidly screened by colony hybridization against 100 organisms on HGMF replicates which can be easily and reproducibly prepared.

Manipulation with small (2–3 mm) chips, and parallel execution of thousands of the reactions. The solution of the invention is to keep the chips and the probes in the corresponding arrays. In one example, chips containing 250,000 9-mers are synthesized on a silicon wafer in the form of 8×8 mM plates (15 uM/oligonucleotide, Pease et al., 1994) arrayed in 8×12 format (96 chips) with a 1 mM groove in between. Probes are added either by multichannel pipette or pin array, one probe on one chip. To score all 4000 6-mers, 42 chip arrays have to be used, either using different ones, or by reusing one set of chip arrays several times.

In the above case, using the earlier nomenclature of the application, F=9; P=6; and F+P=15. Chips may have probes of formula BxNn, where x is a number of specified bases B; and n is a number of non-specified bases, so that x=4 to 10 and n=1 to 4. To achieve more efficient hybridization, and to avoid potential influence of any support oligonucleotides, the specified bases can be surrounded by unspecified bases, thus represented by a formula such as (N)nBx(N)m.

EXAMPLE 6

Preparation of Support Bound Oligonucleotides

Oligonucleotides, i.e., small nucleic acid segments, may be readily prepared by, for example, directly synthesizing the oligonucleotide by chemical means, as is commonly practiced using an automated oligonucleotide synthesizer.

Support bound oligonucleotides may be prepared by any of the methods known to those of skill in the art using any suitable support such as glass, polystyrene or Teflon. One strategy is to precisely spot oligonucleotides synthesized by standard synthesizers. Immobilization can be achieved using passive adsorption (Inouye & Hondo, 1990); using UV light (Nagata et al., 1985; Dahlen et al., 1987; Morriey & Collins, 1989) or by covalent binding of base modified DNA (Keller et al., 1988; 1989); all references being specifically incorporated herein.

Another strategy that may be employed is the use of the strong biotip-streptavidin interaction as a linker. For example, Broude et al. (1994) describe the use of Biotinylated probes, although these are duplex probes, that are immobilized on streptavidin-coated magnetic beads. Streptavidin-coated beads may be purchased from Dynal, Oslo. Of course, this same linking chemistry is applicable to coating any surface with streptavidin. Biotinylated probes may be purchased from various sources, such as, e.g., Operon Technologies (Alameda, Calif.).

Nunc Laboratories (Naperville, Ill.) is also selling suitable material that could be used. Nunc Laboratories have developed a method by which DNA can be covalently bound to the microwell surface termed Covalink NH. CovaLink NH is a polystyrene surface grafted with secondary amino groups (>NH) that serve as bridge-heads for further covalent coupling. CovaLink Modules may be purchased from Nunc Laboratories. DNA molecules may be bound to CovaLink exclusively at the 5'-end by a phosphoramidate bond, allowing immobilization of more than 1 pmol of DNA (Rasmussen et al., 1991).

The use of CovaLink NH strips for covalent binding of DNA molecules at the 5'-end has been described (Rasmussen et al., 1991). In this technology, a phosphoramidate bond is employed (Chu et al., 1983). This is beneficial as immobilization using only a single covalent bond is preferred. The phosphoramidate bond joins the DNA to the CovaLink NH secondary amino groups that are positioned at the end of spacer arms covalently grafted onto the polystyrene surface through a 2 nm long spacer arm. To link an oligonucleotide to CovaLink NH via an phosphoramidate bond, the oligonucleotide terminus must have a 5'-end phosphate group. It is, perhaps, even possible for biotin to be covalently bound to CovaLink and then streptavidin used to bind the probes.

More specifically, the linkage method includes dissolving DNA in water (7.5 ng/ul) and denaturing for 10 min. at 95° C. and cooling on ice for 10 min. Ice-cold 0.1 M 1-methylimidazole pH 7.0 (1-MeIm$_7$), is then added to a final concentration of 10 mM 1-MeIm$_7$. A ss DNA solution is then dispensed into CovaLink NH strips (75 ul/well) standing on ice.

Carbodiimide 0.2 M 1-ethyl-3-(3-dimethylaminopropyl)-carbodiimide (EDC), dissolved in 10 mM 1-MeIm$_7$, is made fresh and 25 ul added per well. The strips are incubated for 5 hours at 50° C. After incubation the strips are washed using, e.g., Nunc-Immuno Wash; first the wells are washed 3 times, then they are soaked with washing solution for 5 min., and finally they are washed 3 times (where in the washing solution is 0.4 N NaOH, 0.25% SDS heated to 50° C.).

It is contemplated that a further suitable method for use with the present invention is that described in PCT Patent Application WO 90/03382 (Southern & Maskos), incorporated herein by reference. This method of preparing an oligonucleotide bound to a support involves attaching a nucleoside 3'-reagent through the phosphate group by a covalent phosphodiester link to aliphatic hydroxyl groups carried by the support. The oligonucleotide is then synthesized on the supported nucleoside and protecting groups removed from the synthetic oligonucleotide chain under standard conditions that do not cleave the oligonucleotide from the support. Suitable reagents include nucleoside phosphoramidite and nucleoside hydrogen phosphorate.

An on-chip strategy for the preparation of DNA probe for the preparation of DNA probe arrays may be employed. For example, addressable laser-activated photodeprotection may be employed in the chemical synthesis of oligonucleotides directly on a glass surface, as described by Fodor et al. (1991), incorporated herein by reference. Probes may also be immobilized on nylon supports as described by Van Ness et al. (1991); or linked to Teflon using the method of Duncan & Cavalier (1988); all references being specifically incorporated herein.

To link an oligonucleotide to a nylon support, as described by Van Ness et al. (1991), requires activation of the nylon surface via alkylation and selective activation of the 5'-amine of oligonucleotides with cyanuric chloride.

One particular way to prepare support bound oligonucleotides is to utilize the light-generated synthesis described by Pease et al., (1994, incorporated herein by reference). These authors used current photolithographic techniques to generate arrays of immobilized oligonucleotide probes (DNA chips). These methods, in which light is used to direct the synthesis of oligonucleotide probes in high-density, miniaturized arrays, utilize photolabile 5'-protected N-acyl-deoxynucleoside phosphoramidites, surface linker chemistry and versatile combinatorial synthesis strategies. A matrix of 256 spatially defined oligonucleotide probes may be generated in this manner and then used in the advantageous Format 3 sequencing, as described herein.

Of course, one could easily purchase a DNA chip, such as one of the light-activated chips described above, from a commercial source. In this regard, one may contact Affymetrix of Santa Clara, Calif. 95051, and Beckman.

EXAMPLE 7

Preparation of Nucleic Acid Fragments

The nucleic acids to be sequenced may be obtained from any appropriate source, such as cDNAs, genomic DNA, chromosomal DNA, microdissected chromosome bands, cosmid or YAC inserts, and RNA, including mRNA without any amplification steps. For example, Sambrook et al. (1989) describes three protocols for the isolation of high molecular weight DNA from mammalian cells (p. 9.14–9.23).

DNA fragments may be prepared as clones in M13, plasmid or lambda vectors and/or prepared directly from genomic DNA or cDNA by PCR or other amplification methods. Samples may be prepared or dispensed in multi-well plates. About 100–1000 ng of DNA samples may be prepared in 2–500 ml of final volume.

The nucleic acids would then be fragmented by any of the methods known to those of skill in the art including, for example, using restriction enzymes as described at 9.24–9.28 of Sambrook et al. (1989), shearing by ultrasound and NaOH treatment.

Low pressure shearing is also appropriate, as described by Schriefer et al. (1990, incorporated herein by reference). In this method, DNA samples are passed through a small French pressure cell at a variety of low to intermediate pressures. A lever device allows controlled application of low to intermediate pressures to the cell. The results of these studies indicate that low-pressure shearing is a useful alternative to sonic and enzymatic DNA fragmentation methods.

One particularly suitable way for fragmenting DNA is contemplated to be that using the two base recognition endonuclease, CviJI, described by Fitzgerald et al. (1992). These authors described an approach for the rapid fragmentation and fractionation of DNA into particular sizes that they contemplated to be suitable for shotgun cloning and sequencing. The present inventor envisions that this will also be particularly useful for generating random, but relatively small, fragments of DNA for use in the present sequencing technology.

The restriction endonuclease CviJI normally cleaves the recognition sequence PuGCPy between the G and C to leave blunt ends. Atypical reaction conditions, which alter the specificity of this enzyme (CviJI), yield a quasi-random distribution of DNA fragments form the small molecule pUC19 (2688 base pairs). Fitzgerald et al. (1992) quantitatively evaluated the randomness of this fragmentation strategy, using a CviJI digest of pUC19 that was size fractionated by a rapid gel filtration method and directly ligated, without end repair, to a lac Z minus M13 cloning vector. Sequence analysis of 76 clones showed that CviJI** restricts pyGCPy and PuGCPu, in addition to PuGCPy sites, and that new sequence data is accumulated at a rate consistent with random fragmentation.

As reported in the literature, advantages of this approach compared to sonication and agarose gel fractionation include: smaller amounts of DNA are required (0.2–0.5 ug instead of 2–5 ug); and fewer steps are involved (no preligation, end repair, chemical extraction, or agarose gel electrophoresis and elution are needed). These advantages are also proposed to be of use when preparing DNA for sequencing by Format 3.

Irrespective of the manner in which the nucleic acid fragments are obtained or prepared, it is important to denature the DNA to give single stranded pieces available for hybridization. This is achieved by incubating the DNA solution for 2–5 minutes at 80–90° C. The solution is then cooled quickly to 2° C. to prevent renaturation of the DNA fragments before they are contacted with the chip. Phosphate groups must also be removed from genomic DNA, as described in Example VI.

EXAMPLE 8

Preparation of DNA Arrays

Arrays may be prepared by spotting DNA samples on a support such as a nylon membrane. Spotting may be performed by using arrays of metal pins (the positions of which correspond to an array of wells in a microtiter plate) to repeated by transfer of about 20 nl of a DNA solution to a nylon membrane. By offset printing, a density of dots higher than the density of the wells is achieved. One to 25 dots may be accommodated in 1 mm$^2$, depending on the type of label used. By avoiding spotting in some preselected number of rows and columns, separate subsets (subarrays) may be formed. Samples in one subarray may be the same genomic segment of DNA (or the same gene) from different individuals, or may be different, overlapped genomic clones. Each of the subarrays may represent replica spotting of the same samples. In one example, a selected gene segment may be amplified from 64 patients. For each patient, the amplified gene segment may be in one 96-well plate (all 96 wells containing the same sample). A plate for each of the 64 patients is prepared. By using a 96-pin device, all samples may be spotted on one 8×12 cm membrane. Subarrays may contain 64 samples, one from each patient. Where the 96 subarrays are identical, the dot span may be 1 mm$^2$ and there may be a 1 mm space between subarrays.

Another approach is to use membranes or plates (available from NUNC, Naperville, Ill.) which may be partitioned by physical spacers e.g. a plastic grid molded over the membrane, the grid being similar to the sort of membrane applied to the bottom of multiwell plates, or hydrophobic strips. A fixed physical spacer is not preferred for imaging by exposure to flat phosphor-storage screens or x-ray films.

EXAMPLE 9

Hybridization and Scoring Process

Labeled probes may be mixed with hybridization buffer and pipetted, preferably by multichannel pipettes, to the subarrays. To prevent mixing of the probes between subarrays (if there are no hydrophobic strips or physical barriers imprinted in the membrane), a corresponding plastic, metal or ceramic grid may be firmly pressed to the membrane. Also, the volume of the buffer may be reduced to about 1 ml or less per mm$^2$. The concentration of the probes and hybridization conditions used may be as described previously except that the washing buffer may be quickly poured over the array of subarrays to allow fast dilution of probes and thus prevent significant cross-hybridization. For the same reason, a minimal concentration of the probes may be used and hybridization time extended to the maximal practical level. For DNA detection and sequencing, knowledge of a "normal" sequence allows the use of the continuous stacking interaction phenomenon to increase the signal. In addition to the labelled probe, additional unlabelled probes which hybridize back to back with a labelled one may be added in the hybridization reaction. The amount of the hybrid may be increased several times. The probes may be connected by ligation. This approach may be important for resolving DNA regions forming "compressions".

In the case of radiolabelled probes, images of the filters may be obtained, preferably by phosphorstorage technology. Fluorescent labels may be scored by CCD cameras, confocal microscopy or otherwise. In order to properly scale and integrate data from different hybridization experiments, raw signals are normalized based on the amount of target in each dot. Differences in the amount of target DNA per dot may be corrected for by dividing signals of each probe by an average signal for all probes scored on one dot. The normalized signals may be scaled, usually from 1–100, to compare data from different experiments. Also, in each subarray, several control DNAs may be used to determine an average background signal in those samples which do not contain a full match target. For samples obtained from diploid (polyploid) scores, homozygotic controls may be used to allow recognition of heterozygotes in the samples.

EXAMPLE 10

Hybridization with Oligonucleotides

Oligonucleotides were either purchased from Genosys Inc., Houston, Tex. or made on an Applied Biosystems 381A DNA synthesizer. Most of the probes used were not purified by HPLC or gel electrophoresis. For example, probes were designed to have both a single perfectly complementary target in interferon, a M13 clone containing a 921 bp Eco RI-Bgl II human B1-interferon fragment (Ohno and Tangiuchi, Proc. Natl. Acad. Sci. 74: 4370–4374 (1981)], and at least one target with an end base mismatch in M13 vector itself.

End labelling of oligonucleotides was performed as described [Maniatis et al., *Molecular Cloning. A Laboratory Manual,* Cold Spring Harbor Laboratory Cold Spring Harbor, N.Y. (1982)] in 10 ml containing T4-polynucleotide kinase (5 units Amersham), g$^{32P}$-ATP (3.3 pM, 10 mCi Amersham 3000 Ci/mM) and oligonucleotide (4 pM, 10 ng). Specific activities of the probes were 2.5–5×10 9 cpm/nM.

Single stranded DNA (2 to 4 ml in 0.5 NaOH, 1.5 M NaCl) was spotted on a Gene Screen membrane wetted with the same solution, the filters were neutralized in 0.05 M Na$_2$HPO$_4$ pH 6.5, baked in an oven at 80° C. for 60 min. and UV irradiated for 1 min. Then, the filters were incubated in hybridization solution (0.5 M Na$_2$HPO$_4$ pH 7.2, 7% sodium lauroyl sarcosine for 5 min at room temperature and placed on the surface of a plastic Petri dish. A drop of hybridization solution (10 ml, 0.5 M Na$_2$HPO$_4$ pH 7.2, 7% sodium lauroyl sarcosine) with a $^{32}$P end-labeled oligomer probe at 4 nM concentration was placed over 1–6 dots per filter, overlaid with a square piece of polyethylene (approximately 1×1 cm.), and incubated in a moist chamber at the indicated temperatures for 3 hr. Hybridization was stopped by placing the filter in 6×SSC washing solution for 3×5 minute at 0° C. to remove unhybridized probe. The filter was either dried, or further washed for the indicated times and temperatures, and autoradiographed. For discrimination measurements, the dots were excised from the dried filters after autoradiography [a phosphoimager (Molecular Dynamics, Sunnyvale, Calif.) may be used] placed in liquid scintillation cocktail and counted. The uncorrected ratio of cpms for IF and M13 dots is given as D.

The conditions reported herein allow hybridization with very short oligonucleotides but ensure discriminations between matched and mismatched oligonucleotides that are complementary to and therefore bind to a target nucleic acid. Factors which influence the efficient detection of hybridization of specific short sequences based on the degree of discriminations (D) between a perfectly complementary target and an imperfectly complementary target with a single mismatch in the hybrid are defined. In experimental tests, dot blot hybridization of twenty-eight probes that were 6 to 8 nucleotides in length to two M13 clones or to model oligonucleotides bound to membrane filters was accomplished. The principles guiding the experimental procedures are given below.

Oligonucleotide hybridization to filter bound target nucleic acids only a few nucleotides longer than the probe in conditions of probe excess is a pseudo-first order reaction with respect to target concentration. This reaction is defined by:

$$S_t/S_o = e^{-kh[OP]t}$$

Wherein $S_t$ and $S_0$ are target sequence concentrations at time t and $t_o$, respectively. (OP) is probe concentration and t is temperature. The rate constant for hybrid formation, $k_n$ increases only slightly in the 0° C. to 30° C. range (Porschke and Eigen, *J. Mol. Biol.* 62: 361 (1971); Craig et al., *J. Mol. Biol.* 62:383 (1971)]. Hybrid melting is a first order reaction with respect to hybrid concentration (here replaced by mass due to filter bound state) as shown in:

$$H_t/H_o = e^{-k_m t}$$

In this equation, $H_t$ and $H_o$ are hybrid concentrations at times t and $t_o$, respectively; $k_m$ is a rate constant for hybrid melting which is dependent on temperature and salt concentration [Ikuta et al., *Nucl. Acids Res.* 15: 797 (1987); Porsclike and Eigen, *J. Mol. Biol.* 62: 361 (1971); Craig et al., J. Mol. Biol. 62: 303 (1971)]. During hybridization, which is a strand association process, the back, melting, or strand dissociation, reaction takes place as well. Thus, the amount of hybrid formed in time is result of forward and back reactions. The equilibrium may be moved towards hybrid formation by increasing probe concentration and/or decreasing temperature. However, during washing cycles in large volumes of buffer, the melting reaction is dominant and the back reaction hybridization is insignificant, since the probe is absent. This analysis indicates workable Short Oligonucleotide Hybridization (SOH) conditions call be varied for probe concentration or temperature.

D or discrimination is defined in equation four:

$$D = H_p(t_w)/H_i(t_w)$$

$H_p(t_w)$ and $H_i(t_w)$ are the amounts hybrids remaining after a washing time, $t_w$, for the identical amounts of perfectly and imperfectly complementary duplex, respectively. For a given temperature, the discrimination D changes with the 10 length of washing time and reaches the maximal value when $H_i = B$ which is equation five.

The background, B, represents the lowest hybridization signal detectable in the system. Since any further decrease of $H_i$ may not be examined, D increases upon continued washing. Washing past $t_w$, just decreases $H_p$ relative to B, and is seen as a decrease in D. The optimal washing time, $t_w$, for imperfect hybrids, from equation three and equation five is:

$$t_w = -\ln(B/H_i(t_0))k_{m,i}$$

Since $H_p$ is being washed for the same $t_w$, combining equations, one obtains the optimal discrimination function:

$$D = e^{\ln(B/H_i(t_0))k_{m,p}/k_{m,i}} X H_p(t_0)/B$$

The change of D as a function, of T is important because of the choice of an optimal washing temperature. It is obtained by substituting the Arhenius equation which is:

$$K = Ae^{-Ea/RT}$$

into the previous equation to form the final equation:

$$D = H_p((t_0)/BX(B/H_i(t_0))^{(Ap/Ai)e(E_{a,i} - E_{a,p})/RT};$$

Wherein B is less than $H_i(t_0)$.

Since the activation energy for perfect hybrids, $E_{a,p}$, and the activation energy for imperfect hybrids, $E_{a,i}$, can be either equal, or $E_{a,i}$ less than $E_{a,p}$ D is temperature independent, or decreases with increasing temperature, respectively. This result implies that the search for stringent temperature conditions for good discrimination in SOH is unjustified. By washing at lower temperatures, one obtains equal or better discrimination, but the time of washing exponentially increases with the decrease of temperature. Discrimination more strongly decreases with T, if $H_i(t_O)$ increases relative to $H_p(t_0)$.

D at lower temperatures depends to a higher degree on the $H_p(t_0)/B$ ratio than on the $H_p(t_0)/H_i(t_0)$ ratio. This result indicates that it is better to obtain a sufficient quantity of $H_p$ in the hybridization regardless of the discrimination that can be achieved in this step. Better discrimination can then be obtained by washing, since the higher amounts of perfect hybrid allow more time for differential melting to show an effect. Similarly, using larger amounts of target nucleic acid a necessary discrimination can be obtained even with small differences between $K_{m,p}$ and $K_{m,i}$.

Extrapolated to a more complex situation than covered in this simple model, the result is that washing at lower temperatures is even more important for obtaining discrimination in the case of hybridization of a probe having many end-mismatches within a given nucleic acid target.

Using the described theoretical principles as a guide for experiments, reliable hybridizations have been obtained with probes six to eight nucleotides in length. All experiments were performed with a floating plastic sheet providing a film of hybridization solution above the filter. This procedure allows maximal reduction in the amount of probe, and thus reduced label costs in dot blot hybridizations. The high concentration of sodium lauroyl sarcosine instead of sodium lauroyl sulfate in the phosphate hybridization buffer allows dropping the reaction from room temperature down to 12° C. Similarly, the 4–6×SSC, 10% sodium lauroyl sarcosine buffer allows hybridization at temperatures as low as 2° C. The detergent in these buffers is for obtaining tolerable background with up to 40 nM concentrations of labelled probe. Preliminary characterization of the thermal stability of short oligonucleotide hybrids was determined on a prototype octamer with 50% G+C content, i.e. probe of sequence TGCTCATG. The theoretical expectation is that this probe is among the less stable octamers. Its transition enthalpy is similar to those of more stable heptamers or, even to probes 6 nucleotides in length (Bresslauer et al., *Proc. Natl. Acad. Sci.* U.S.A. 83:3746 (1986)). Parameter $T_d$, the temperature at which 50% of the hybrid is melted in unit time of a minute is 18° C. The result shows that $T_d$ is 15° C. lower for the 8 bp hybrid than for an 11 bp duplex [Wallace et al., *Nucleic Acids Res.* 6:3543 (1979)].

In addition to experiments with model oligonucleotides, an M13 vector was chosen as a system for a practical demonstration of short oligonucleotide hybridization. The main aim was to show useful end-mismatch discrimination with a target similar to the ones which will be used in various applications of the method of the invention. Oligonucleotide probes for the M13 model were chosen in such a way that the M13 vector itself contains the end mismatched base. Vector IF, an M13 recombinant containing a 921 bp human interferon gene insert, carries single perfectly matched target. Thus, IF has either the identical or a higher number of mismatched targets in comparison to the M13 vector itself.

Using low temperature conditions and dot blots, sufficient differences in hybridization signals were obtained between tie dot containing the perfect and the mismatched targets and the dot containing the mismatched targets only. This was true for the 6-mer oligonucleotides and was also true for the 7 and 8-mer oligonucleotides hybridized to the large IF-M13 pair of nucleic acids.

The hybridization signal depends on the amount of target available on the filter for reaction with the probe. A necessary control is to show that the difference in sign intensity is not a reflection of varying amounts of nucleic acid in the two dots. Hybridization with a probe that has the same number and kind of targets in both IF and M13 shows that there is an equal amount of DNA in the dots. Since the efficiency of hybrid formation increases with hybrid length, the signal for a duplex having six nucleotides was best detected with a high mass of oligonucleotide target bound to the filter. Due to their lower molecular weight, a larger number of oligonucleotide target molecules can be bound to a given surface area when compared to large molecules of nucleic acid that serves as target.

To measure the sensitivity of detection with unpurified DNA, various amounts of phage supernatants were spotted on the filter and hybridized with a $^{32}$P-labelled octamer. As little as 50 million unpurified phage containing no more than 0.5 ng of DNA gave a detectable signal indicating that sensitivity of the short oligonucleotide hybridization method is sufficient. Reaction time is short, adding to the practicality.

As mentioned in the theoretical section above, the equilibrium yield of hybrid depends oil probe concentration and/or temperature of reaction. For instance, the signal level for the same amount of target with 4 nM octamer at 13° C. is 3 times lower than with a probe concentration of 40 nM, and is decreased 4.5-times by raising the hybridization temperature to 25° C.

The utility of the low temperature wash for achieving maximal discrimination is demonstrated. To make the phenomenon visually obvious, 50 times more DNA was put in the M13 dot than in the IF dot using hybridization with a vector specific probe. In this way, the signal after the hybridization step with the actual probe was made stronger in the, mismatched that in the matched case. The $H_p/H_i$ ratio was 1:4. Inversion of signal intensities after prolonged washing at 7° C. was achieved without a massive loss of perfect hybrid, resulting in a ratio of 2:1. In contrast, it is impossible to achieve any discrimination at 25° C., since the matched target signal is already brought down to the background level with 2 minute washing; at the same time, the signal from the mismatched hybrid is still detectable. The loss of discrimination at 13° C. compared to 7° C. is not so great but is clearly visible. If one considers the 90 minute point at 7° C. and the 15 minute point at 13° C. when, the mismatched hybrid signal is near the background level, which represents optimal washing times for the respective conditions, it is obvious that the amount of several times greater at 7° C. than at 13° C. To illustrate this further, the time course of the change discrimination with washing of the same amount of starting hybrid at the two temperatures shows the higher maximal D at the lower temperature. These results confirm the trend in the change of D with temperature and the ratio of amounts of the two types of hybrid at the start of the washing step.

In order to show the general utility of the short oligonucleotide hybridization conditions, we have looked hybridization of 4 heptamers, 10 octamers and an additional 14 probes up to 12 nucleotides in length in our simple M13 system. These include-the nonamer GTTTTTTAA and octamer GGCAGGCG representing the two extremes of GC content. Although GC content and sequence are expected to influence the stability of short hybrids [Bresslauer et al., Proc. Natl. Acad. Sci. U.S.A. 83:3746 (1986)], the low temperature short oligonucleotide conditions were applicable to all tested probes in achieving sufficient discrimination. Since the best discrimination value obtained with probes 13 nucleotides in length was 20, a several fold drop due to sequence variation is easily tolerated.

The M13 system has the advantage of showing the effects of target DNA complexity on the levels of discrimination. For two octamers having either none or five mismatched targets and differing in only one GC pair the observed discriminations were 18.3 and 1.7, respectively.

In order to show the utility of this method, three probes 8 nucleotides in length were tested on a collection of 51 plasmid DNA dots made from a library in Bluescript vector. One probe was present and specific for Bluescript vector but was absent in M13, while the other two probes had targets that were inserts of known sequence. This system allowed the use of hybridization negative or positive control DNAs with each probe. This probe sequence (CTCCCTTT) also had a complementary target in the interferon insert. Since the M13 dot is negative while the interferon insert in either M13 or Bluescript was positive, the hybridization is sequence specific. Similarly, probes that detect the target sequence in only one of 51 inserts, or in none of the examined inserts along with controls that confirm that hybridization would have occurred if the appropriate targets were present in the clones.

Thermal stability curves for very short oligonucleotide hybrids that are 6–8 nucleotides in length are at least 15° C. lower than for hybrids 11–12 nucleotides in length [Wallace et al., Nucleic Acids Res. 6: 3543–3557 (1979)]. However, performing the hybridization reaction at a low temperature and with a very practical 0.4–40 nM concentration of oligonucleotide probe allows the detection of complementary sequence in a known or unknown nucleic acid target. To determine an unknown nucleic acid sequence completely, an entire set containing 65,535 8-mer probes may be used. Sufficient amounts of nucleic acid for this purpose are present in convenient biological samples such as a few microliters of M13 culture, a plasmid prep from 10 ml of bacterial culture or a single colony of bacteria, or less than 1 ml of a standard PCR reaction.

Short oligonucleotides 6–10 nucleotides long give excellent discrimination. The relative decrease in hybrid stability with a single end mismatch is greater than for longer probes. Results with the octamer TGCTCATG support this conclusion. In the experiments, the target with a G/T end mismatch, hybridization to the target of this type of mismatch is the most stable of all other types of oligonucleotide. This discrimination achieved is the same as or greater than an internal G/T mismatch in a 19 base paired duplex greater than an internal G/T mismatch in a 19 paired duplex [Ikuta et al., Nucl. Acids res. 15: 797 (1987)]. Exploiting these discrimination properties using the described hybridization conditions for short oligonucleotide hybridization allows a very precise determination of oligonucleotide targets. In contrast to the ease of detecting discrimination between perfect and imperfect hybrids, a problem that may exist with using very short oligonucleotides is the preparation of sufficient amounts of hybrids. In practice, the need to discriminate $H_p$ and $H_i$ is aided by increasing the amount of DNA in the dot and/or the probe concentration, or by decreasing the hybridization temperature. However, higher probe concentrations usually increase background. Moreover, there are limits to the amounts of target nucleic acid that are practical to use. This problems was solved by the higher concentration of the detergent Sarcosyl which gave an effective background with 4 nM of probe. Further improvements may be effected either in the use of competitors for unspecific binding of probe to filter, or by changing the hybridization support material. Moreover, for probes having $E_a$ less than 45 Kcal/mol (e.g. for many heptamers and a majority of hexamers, modified oligonucleotides give a more stable hybrid [Asseline, et al., *Proc. Nat'l Acad. Sci.* 81: 3297 (1984)] than their Unmodified counterparts. The hybridization conditions described in this invention for short oligonucleotide hybridization using low temperatures give better discriminating for all sequences and duplex hybrid inputs. The only price paid in achieving uniformity in hybridization conditions for different sequences is an increase in washing time from minutes to up to 24 hours depending on the sequence. Moreover, the washing time can be further reduced by decreasing the salt concentration.

Although there is excellent discrimination of one matched hybrid over a mismatched hybrids, in short oligonucleotide hybridization, signals from mismatched hybrids exist, with the majority of the mismatch hybrids resulting from end mismatch. This may limit insert sizes that may be effectively examined by a probe of a certain length.

The influence of sequence complexity on discrimination cannot be ignored. However, the complexity effects are more significant when defining sequence information by short oligonucleotide hybridization for specific, nonrandom sequences, and can be overcome by using an appropriate probe to target length ratio. The length ratio is chosen to make unlikely, on statistical grounds, the occurrence of specific sequences which have a number of end-mismatches which would be able to eliminate or falsely invert discrimination. Results suggest the use of oligonucleotides 6, 7, and 3 nucleotides in length on target nucleic acid inserts shorter than 0.6, 2.5, and 10 kb, respectively.

EXAMPLE 11

DNA Sequencing

An array of subarrays allows for efficient sequencing of a small set of samples arrayed in the form of replicated subarrays; For example, 64 samples may be arrayed on a 8×8 mm subarray and 16×24 subarrays may be replicated on a 15×23 cm membrane with 1 mm wide spacers between the subarrays. Several replica membranes may be made. For example, probes from a universal set of three thousand seventy-two 7-mers may be divided in thirty-two 96-well plates and labeled by kinasing. Four membranes may be processed in parallel during one hybridization cycle. On each membrane, 384 probes may be scored. All probes may be scored in two hybridization cycles. Hybridization intensities may be scored and the sequence assembled as described below.

If a single sample subarray or subarrays contains several unknowns, especially when similar samples are used, a smaller number of probes may be sufficient if they are intelligently selected on the basis of results of previously scored probes. For example, if probe AAAAAAA is not positive, there is a small chance that any of 8 overlapping probes are positive. If AAAAAAA is positive, then two probes are usually positive. The sequencing process in this case consists of first hybridizing a subset of minimally overlapped probes to define positive anchors and then to successively select probes which confirms one of the most likely hypotheses about the order of anchors and size and type of gaps between them. In this second phase, pools of 2–10 probes may be used where each probe is selected to be positive in only one DNA sample which is different from the samples expected to be positive with other probes from the pool.

The subarray approach allows efficient implementation of probe competition (overlapped probes) or probe cooperation (continuous stacking of probes) in solving branching problems. After hybridization of a universal set of probes the sequence assembly program determines candidate sequence subfragments (SFs). For the further assembly of SFs, additional information has to be provided (from overlapped sequences of DNA fragments, similar sequences, single pass gel sequences, or from other hybridization or restriction mapping data). Competitive hybridization and continuous stacking interactions have been proposed for SF assembly. These approaches are of limited practical value for sequencing of large numbers of samples by SBH wherein a labeled probe is applied to a sample affixed to an array if a uniform array is used. Fortunately, analysis of small numbers of samples using replica subarrays allows efficient implementation of both approaches. On each of the replica subarrays, one branching point may be tested for one or more DNA samples using pools of probes similarly as in solving mutated sequences in different samples spotted in the same subarray (see above).

If in each of 64 samples described in this example, there are about 100 branching points, and if 8 samples are analyzed in parallel in each subarray, then at least 800 subarray probings solve all branches. This means that for the 3072 basic probings an additional 800 probings (25%) are employed. More preferably, two probings are used for one branching point. If the subarrays are smaller, less additional probings are used. For example, if subarrays consist of 16 samples, 200 additional probings may be scored (6%). By using 7-mer probes ($N_{1-2}B_7N_{1-2}$) and competitive or collaborative branching solving approaches or both, fragments of about 1000 bp fragments may be assembled by about 4000 probings. Furthermore, using 8-mer probes ($NB_4N$) 4 kb or longer fragments may be assembled with 12,000 probings. Gapped probes, for example, $NB_4NB_3N$ or $NB_4NB_4N$ may be used to reduce the number of branching points.

EXAMPLE 12

DNA Analysis by Transient Attachment to Subarrays of Probes and Ligation of Labelled Probes Oligonucleotide probes having an informative length of four to 40 bases are synthesized by standard chemistry and stored in tubes or in multiwell plates. Specific sets of probes comprising one to 10,000 probes are arrayed by deposition or in situ synthesis on separate supports or distinct sections of a larger support. In the last case, sections or subarrays may be separated by physical or hydrophobic barriers. The probe arrays may be prepared by in situ synthesis. A sample DNA of appropriate size is hybridized with one or more specific arrays. Many samples may be interrogated as pools at the same subarrays or independently with different subarrays within one support. Simultaneously with the sample or subsequently, a single labeled probe or a pool of labeled probes is added on each of the subarrays. If attached and labeled probes hybridize back to back on the complementary target in the sample DNA they are ligated. Occurrence of ligation will be measured by detecting a label from the probe.

This procedure is a variant of the described DNA analysis process in which DNA samples are not permanently attached to the support. Transient attachment is provided by probes fixed to the support. In this case there is no need for a target DNA arraying process. In addition, ligation allows detection of longer oligonucleotide sequences by combining short labeled probes with short fixed probes.

The process has several unique features. Basically, the transient attachment of the target allows its reuse. After ligation occur the target may be released and the label will stay covalently attached to the support. This feature allows cycling the target and production of detectable signal with a small quantity of the target. Under optimal conditions, targets do not need to be amplified, e.g. natural sources of the DNA samples may be directly used for diagnostics and sequencing purposes. Targets may be released by cycling the temperature between efficient hybridization and efficient melting of duplexes. More preferably, there is no cycling. The temperature and concentrations of components may be defined to have an equilibrium between free targets and targets entered in hybrids at about 50:50% level. In this case there is a continuous production of ligated products. For different purposes different equilibrium ratios are optimal.

An electric field may be used to enhance target use. At the beginning, a horizontal field pulsing within each subarray may be employed to provide for faster target sorting. In this phase, the equilibrium is moved toward hybrid formation, and unlabeled probes may be used. After a target sorting phase, an appropriate washing (which may be helped by a vertical electric field for restricting movement of the samples) may be performed. Several cycles of discriminative hybrid melting, target harvesting by hybridization and ligation and removing of unused targets may be introduced to increase specificity. In the next step, labeled probes are added and vertical electrical pulses may be applied. By increasing temperature, an optimal free and hybridized target ratio may be achieved. The vertical electric field prevents diffusion of the sorted targets.

The subarrays of fixed probes and sets of labeled probes (specially designed or selected from a universal probe set) may be arranged in various ways to allow an efficient and flexible sequencing and diagnostics process. For example, if a short fragment (about 100–500 bp) of a bacterial genome is to be partially or completely sequenced, small arrays of probes (5–30 bases in length) designed on the bases of known sequence may be used. If interrogated with a different pool of 10 labeled probes per subarray, an array of 10 subarrays each having 10 probes, allows checking of 200 bases, assuming that only two bases connected by ligation are scored. Under the conditions where mismatches are discriminated throughout the hybrid, probes may be displaced by more than one base to cover the longer target with the same number of probes. By using long probes, the target may be interrogated directly without amplification or isolation from the rest of DNA in the sample. Also, several targets may be analyzed (screened for) in one sample simultaneously. If the obtained results indicate occurrence of a mutation (or a pathogen), additional pools of probes may be used to detect type of the mutation or subtype of pathogen. This is a desirable feature of the process which may be very cost effective in preventive diagnosis where only a small fraction of patients is expected to have an infection or mutation.

In the processes described in the examples, various detection methods may be used, for example, radiolabels, fluorescent labels, enzymes or antibodies (chemiluminescence), large molecules or particles detectable by light scattering or interferometric procedures.

EXAMPLE 13

Sequencing a Target Using Octamers and Nonamers

Data resulting from the hybridization of octamer and nonamer oligonucleotides shows that sequencing by hybridization provides an extremely high degree of accuracy. In this experiment, a known sequence was used to predict a series of contiguous overlapping component octamer and nonamer oligonucleotides.

In addition to the perfectly matching oligonucleotides, mismatch oligonucleotides, mismatch oligonucleotides wherein internal or end mismatches occur in the duplex formed by the oligonucleotide and the target were examined. In these analyses, the lowest practical temperature was used to maximize hybridization formation. Washes were accomplished at the same or lower temperatures to ensure maximal discrimination by utilizing the greater dissociation rate of mismatch versus matched oligonucleotide/target hybridization. These conditions are shown to be applicable to all sequences although the absolute hybridization yield is shown to be sequence dependent.

The least destabilizing mismatch that can be postulated is a simple end mismatch, so that the test of sequencing by hybridization is the ability to discriminate perfectly matched oligonucleotide/target duplexes from end-mismatched oligonucleotide/target duplexes.

The discriminative values for 102 of 105 hybridizing oligonucleotides in a dot blot format were greater than 2 allowing a highly accurate generation of the sequence. This system also allowed an analysis of the effect of sequence on hybridization formation and hybridization instability.

One hundred base pairs of a known portion of a human-interferon genes prepared by PCR, i.e. a 100 bp target sequence, was generated with data resulting from the hybridization of 105 oligonucleotides probes of known sequence to the target nucleic acid. The oligonucleotide probes used included 72 octamer and 21 nonamer oligonucleotides whose sequence was perfectly complementary to the target. The set of 93 probes provided consecutive overlapping frames of the target sequence e displaced by one or two bases.

To evaluate the effect of mismatches, hybridization was examined for 12 additional probes that contained at least one end mismatch when hybridized to the 100 bp test target sequence. Also tested was the hybridization of twelve probes with target end-mismatched to four other control nucleic acid sequences chosen so that the 12 oligonucleotides formed perfectly matched duplex hybrids with the four control DNAs. Thus, the hybridization of internal mismatched, end-mismatched and perfectly matched duplex pairs of oligonucleotide and target were evaluated for each oligonucleotide used in the experiment. The effect of absolute DNA target concentration on the hybridization with the test octamer and nonamer oligonucleotides was determined by defining target DNA concentration by detecting hybridization of a different oligonucleotide probe to a single occurrence non-target site within the co-amplified plasmid DNA.

The results of this experiment showed that all oligonucleotides containing perfect matching complementary sequence to the target or control DNA hybridized more strongly than those oligonucleotides having mismatches. To come to this conclusion, we examined $H_p$ and D values for each probe. $H_p$ defines the amount of hybrid duplex formed between a test target and an oligonucleotide probe. By assigning values of between 0 and 10 to the hybridization obtained for the 105 probes, it was apparent that 68.5% of the 105 probes had an $H_p$ greater than 2.

Discrimination (D) values were obtained where D was defined as the ratio of signal intensities between 1) the dot containing a perfect matched duplex formed between test oligonucleotide and target or control nucleic acid and 2) the dot containing a mismatch duplex formed between the same oligonucleotide and a different site within the target or control nucleic acid. Variations in the value of D result from either 1) perturbations in the hybridization efficiency which allows visualization of signal over background, or 2) the type of mismatch found between the test oligonucleotide and the target. The D values obtained in this experiment were between 2 and 40 for 102 of the 105 oligonucleotide probes examined. Calculations of D for the group of 102 oligonucleotides as a whole showed the average D was 10.6.

There were 20 case where oligonucleotide/target duplexes exhibited an end-mismatch. In five of these, D was greater than 10. The large D value in these cases is most likely due to hybridization destabilization caused by other than the most stable (G/T and G/A) end mismatches. The other possibility is there was an error in the sequence of either the oligonucleotides or the target.

Error in the target for probes with low $H_p$ was excluded as a possibility because such an error would have affected the hybridization of each of the other eight overlapping oligonucleotides. There was no apparent instability due to sequence mismatch for the other overlapping oligonucleotides, indicating the target sequence was correct. Error in the oligonucleotide sequence was excluded as a possibility after the hybridization of seven newly synthesized oligonucleotides was re-examined. Only 1 of the seven oligonucleotides resulted in a better D value. Low hybrid formation values may result from hybrid instability or from an inability to form hybrid duplex. An inability to form hybrid duplexes would result from either 1) self complementarity of the chosen probe or 2) target/target self hybridization. Oligonucleotide/oligonucleotide duplex formation may be favored over oligonucleotide/target hybrid duplex formation if the probe was self-complementary. Similarly, target/target association may be favored if the target was self-complementary or may form internal palindromes. In evaluating these possibilities, it was apparent from probe analysis that the questionable probes did not form hybrids with themselves. Moreover, in examining the contribution of target/target hybridization, it was determined that one of the questionable oligonucleotide probes hybridized inefficiently with two different DNAs containing the same target. The low probability that two different DNAs have a self-complementary region for the same target sequence leads to the conclusion that target/target hybridization did not contribute to low hybridization formation. Thus, these results indicate that hybrid instability and not the inability to form hybrids was the cause of the low hybrid formation observed for specific oligonucleotides. The results also indicate that low hybrid formation is due to the specific sequences of certain oligonucleotides. Moreover, the results indicate that reliable results may be obtained to generate sequences if octamer and nonamer oligonucleotides are used.

These results show that using the methods described long sequences of any specific target nucleic acid may be generated by maximal and unique overlap of constituent oligonucleotides. Such sequencing methods are dependent on the content of the individual component oligomers regardless of their frequency and their position.

The sequence which is generated using the algorithm described below is of high fidelity. The algorithm tolerates false positive signals from the hybridization dots as is indicated from the fact the sequence generated from the 105 hybridization values, which included four less reliable values, was correct. This fidelity in sequencing by hybridization is due to the "all or none" kinetics of short oligonucleotide hybridization and the difference in duplex stability that exists between perfectly matched duplexes and mismatched duplexes. The ratio of duplex stability of matched and end-mismatched duplexes increases with decreasing duplex length. Moreover, binding energy decreases with decreasing duplex length resulting in a lower hybridization efficiency. However, the results provided show that octamer hybridization allows the balancing of the factors affecting duplex stability and discrimination to produce a highly accurate method of sequencing by hybridization. Results presented in other examples show that oligonucleotides that are 6, 7, or 8 nucleotides can be effectively used to generate reliable sequence on targets that are 0.5 kb (for hexamers) 2 kb (for septamers) and 6 kb (for octamers). The sequence of long fragments may be overlapped to generate a complete genome sequence.

EXAMPLE 14

Analyzing the Data Obtained

Image files are analyzed by an image analysis program, like DOTS program (Drmanac et al., 1993), and scaled and evaluated by statistical functions included, e.g., in SCORES program (Drmanac et al. 1994). From the distribution of the signals an optimal threshold is determined for transforming signal into +/− output. From the position of the label detected, F+P nucleotide sequences from the fragments would be determined by combining the known sequences of the immobilized and labeled probes corresponding to the labeled positions. The complete nucleic acid sequence or sequence subfragments of the original molecule, such as a human chromosome, would then be assembled from the overlapping F+P sequence determined by computational deduction.

One option is to transform hybridization signals e.g., scores, into +/− output during the sequence assembly process. In this case, assembly will start with a F+P sequence with a very high score, for example F+P sequence AAAAAATTTTTT (SEQ ID NO:11). Scores of all four possible overlapping probes AAAAATTTTTA (SEQ ID NO: 12), AAAAATTTTTT (SEQ ID NO:13), AAAAATTTTTC (SEQ ID NO:14) and AAAAATTTTTG (SEQ ID NO:15) and three additional probes that are different at the beginning (TAAAAATTTTTT (SEQ ID NO: 16),; CAAAAATTTTTT (SEQ ID NO:17), ; GAAAAATTTTTT (SEQ ID NO:18), are compared and three outcomes defined: (i) only the starting probe and only one of the four overlapping proves have scores that are significantly positive relatively to the other six probes, in this case the AAAAAATTTTTT (SEQ ID NO:11) sequence will be extended for one nucleotide to the right; (ii) no one probe except the starting probe has a significantly positive score, assembly will stop, e.g., the AAAAAATTTTT (SEQ ID NO:19) sequence is at the end of the DNA molecule that is sequenced; (iii) more than one significantly positive probe among the overlapped and/or other three probes is found; assembly is stopped because of the error or branching (Drmanac et al., 1989).

The processes of computational deduction would employ computer programs using existing algorithms (see, e.g., Pevzner, 1989; Drmanac et al., 1991; Labat and Drmanac, 1993; each incorporated herein by reference).

If, in addition to F+P, F (space 1)P, F (space 2)P, F(space 3)P or F(space 4)P are determined, algorithms will be used to match all data sets to correct potential errors or to solve the situation where there is a branching problem (see, e.g., Drmanac et al., 1989; Bains et al., 1988; each incorporated herein by reference).

EXAMPLE 15

Conducting Sequencing by Two Step Hybridization

Following the certain examples to describe the execution of the sequencing methodology contemplated by the inventor. First, the whole chip would be hybridized with mixture of DNA as complex as 100 million of bp (one human chromosome). Guidelines for conducting hybridization can be found in papers such as Drmanac et al. (1990); Khrapko et al. (1991); and Broude et al. (1994). These articles teach the ranges of hybridization temperatures, buffers and washing steps that are appropriate for use in the initial steps of Format 3 SBH.

The present inventor particularly contemplates that hybridization is to be carried out for up to several hours in high salt concentrations at a low temperature (−2° C. to 5° C.) because of a relatively low concentration of target DNA that can be provided. For this purpose, SSC buffer is used instead of sodium phosphate buffer (Drmanac et al, 1990), which precipitates at 10° C. Washing does not have to be extensive (a few minutes) because of the second step, and can be completely eliminated when the hybridization cycling is used for the sequencing of highly complex DNA samples. The same buffer is used for hybridization and washing steps to be able to continue with the second hybridization step with labeled probes.

After proper washing using a simple robotic device on each array, e.g., a 8×8 mm array, one labeled, probe, e.g., a 6-mer, would be added. A 96-tip or 96-pin device would be used, performing this in 42 operations. Again, a range of discriminatory conditions could be employed, as previously described in the scientific literature.

The present inventor particularly contemplates the use of the following conditions. First, after adding labeled probes and incubating for several minutes only (because of the high concentration of added oligonucleotides) at a low temperature (0–5° C.), the temperature is increased to 3–10° C., depending on F+P length, and the washing buffer is added. At this time, the washing buffer used is one compatible with any ligation reaction (e.g., 100 mM salt concentration range). After adding ligase, the temperate is increased again to 15–37° C. to allow fast ligation (less than 30 min) and further discrimination of full match and mismatch hybrids.

The use of cationic detergents is also contemplated for use in Format 3 SBH, as described by Pontius & Berg (1991, incorporated herein by reference). These authors describe the use of two simple cationic detergents, dodecy- and cetyltrimethylammonium bromide (DTAB and CTAB) in DNA renaturation.

DTAB and CTAB are variants of the quaternary amine tetramethylammonium bromide (TMAB) in which one of the methyl groups is replaced by either a 12-carbon (DTAB) or a 16-carbon (CTAB) alkyl group. TMAB is the bromide salt of the tetramethylammonium ion, a reagent used in nucleic acid renaturation experiments to decrease the G-C content bias of the melting temperature. DTAB and CTAB are similar in structure to sodium dodecyl sulfate (SDS), with the replacement of the negatively charged sulfate of SDS by a positively charged quaternary amine. While SDS is commonly used in hybridization buffers to reduce non-specific binding and inhibit nucleases, it does not greatly affect the rate of renaturation.

When using a ligation process, the enzyme could be added with the labeled probes or after the proper washing step to reduce the background. Although not previously proposed for use in any SBH method, ligase technology is well established within the field of molecular biology. For example, Hood and colleagues described a ligase-mediated gene detection technique (Landegren et al., 1988), the methodology of which can be readily adapted for use in Format 3 SBH. Wu & Wallace also describe the use of bacteriophage T4 DNA ligase to join two adjacent, short synthetic oligonucleotides. Their oligo ligation reactions were carried out in 50 mM Tris HCl pH 7.6, 10 mM $MgCl_2$, 1 mM ATP, 1 mM DTT, and 5% PEG. Ligation reactions were heated to 100° C. for 5–10 min followed by cooling to 0° C. prior to the addition of T4 DNA ligase (1 unit; Bethesda Research Laboratory). Most ligation reactions were carried out at 30° C. and terminated by heating to 100° C. for 5 min.

Final washing appropriate for discriminating detection of hybridized adjacent, or ligated, oligonucleotides of length (F+P), is then performed. This washing step is done in water for several minutes at 40–60° C. to wash out all the non-ligated labeled probes, and all other compounds, to maximally reduce background. Because of the covalently bound labeled oligonucleotides, detection is simplified (it does not have time and low temperature constrains).

Depending on the label used, imaging of the chips is done with different apparati. For radioactive labels, phosphor storage screen technology and PhosphorImager as a scanner may be used (Molecular Dynamics, Sunnyvale, Calif.). Chips are put in a cassette and covered by a phosphorous screen. After 1–4 hours of exposure, the screen is scanned and the image file stored at a computer hard disc. For the detection of fluorescent labels, CCD cameras and epifluorescent or confocal microscopy are used. For the chips generated directly on the pixels of a CCD camera, detection can be performed as described by Eggers et al. (1994, incorporated herein by reference).

Charge-coupled device (CCD) detectors serve as active solid supports that quantitatively detect and image the distribution of labeled target molecules in probe-based assays. These devices use the inherent characteristics of microelectronics that accommodate highly parallel assays, ultrasensitive detection, high throughput, integrated data acquisition and computation. Eggers et al. (1994) describe CCDs for use with probe-based assays, such as Format 3 SBH of the present invention, that allow quantitative assessment within seconds due to the high sensitivity and direct coupling employed.

The integrated CCD detection approach enables the detection of molecular binding events on chips. The detector rapidly generates a two-dimensional pattern that uniquely characterizes the sample. In the specific operation of the CCD-based molecular detector, distinct biological probes are immobilized directly on the pixels of a CCD or can be attached to a disposable cover slip placed on the CCD surface. The sample molecules can be labeled with radioisotope, chemiluminescent or fluorescent tags.

Upon exposure of the sample to the CCD-based probe array, photons or radioisotope decay products are emitted at the pixel locations where the sample has bound, in the case of Format 3, to two complementary probe. In turn, electron-hole pairs are generated in the silicon when the charged particles, or radiation from the labeled sample, are incident on the CCD gates. Electrons are then collected beneath on adjacent CCD gates and sequentially read out on a display module. The number of photoelectrons generated at each pixel is directly proportional to the number of molecular binding events in such proximity. Consequently, molecular binding can be quantitatively determined (Eggers et al., 1994).

By placing the imaging array in proximity to the sample, the collection efficiency is improved by a factor of at least 10 over lens-based techniques such as those found in conventional CCD cameras. That is, the sample (emitter) is in near contact with the detector (imaging array), and this eliminates conventional imaging optics such as lenses and mirrors.

When radioisotopes are attached as reporter groups to the target molecules, energetic particles are detected. Several reporter groups that emit particles of varying energies have been successfully utilized with the micro-fabricated detectors, including $^{32}P$, $^{33}P$, $^{35}S$, $^{14}C$ and $^{125}L$. The higher energy particles, such as from $^{32}P$, provide the highest molecular detection sensitivity, whereas the lower energy particles, such as from $^{35}S$, provide better resolution. Hence the choice of the radioisotope reporter can be tailored as required. Once the particular radioisotope label is selected, the detection performance can be predicted by calculating the signal-to-noise ration (SNR), as described by Eggers et al. (1994).

An alternative luminescent detection procedure involves the use of fluorescent or chemiluminescent reporter groups attached to the target molecules. The fluorescent labels can be attached covalently or through interaction. Fluorescent dyes, such as ethidium bromide, with intense absorption bands in the near UV (300–350 nm) range and principal emission bands in the visible (500–650 nm) range, are most suited for the CCD devices employed since the quantum efficiency is several orders of magnitude lower at the excitation wavelength then at the fluorescent signal wavelength.

From the perspective of detecting luminescence, the polysilicon CCD gates have the built-in capacity to filter away the contribution of incident light in the UV range, yet are very sensitive to the visible luminescence generated by the fluorescent reporter groups. Such inherently large discrimination against UV excitation enables large SNRs (greater than 100) to be achieved by the CCDs as formulated in the incorporated paper by Eggers et al. (1994).

For probe immobilization on the detector, hybridization matrices may be produced on inexpensive $SiO_2$ wafers, which are subsequently placed on the surface of the CCD following hybridization and drying. This format is economically efficient since the hybridization of the DNA is conducted on inexpensive disposable $SiO_2$ wafers, thus allowing reuse of the more expensive CCD detector. Alternatively, the probes can be immobilized directly on the CCD to create a dedicated probe matrix.

To immobilize probes upon the $SiO_2$ coating, a uniform epoxide layer is linked to the film surface, employing an epoxy-silane reagent and standard $SiO_2$ modification chemistry. Amine-modified oligonucleotide probes are then linked to the $SiO_2$ surface by means of secondary amine formation with the epoxide ring. The resulting linkage provides 17 rotatable bonds of separation between the 3 base of the oligonucleotide and the $SiO_2$ surface. To ensure complete amine deprotonation and to minimize secondary structure formation during coupling, the reaction is performed in 0.1 M KOH and incubated at 37° C. for 6 hours.

In Format 3 SBH in general, signals are scored per each of billion points. It would not be necessary to hybridize all arrays, e.g., 4000 5×5 mm, at a time and the successive use of smaller number of arrays is possible.

Cycling hybridizations are one possible method for increasing the hybridization signal. In one cycle, most of the fixed probes will hybridize with DNA fragments with tail sequences non-complementary for labeled probes. By increasing the temperature, those hybrids will be melted. In the next cycle, some of them (~0.1%) will hybridize with an appropriate DNA fragment and additional labeled probes will be ligated. In this case, there occurs a discriminative melting of DNA hybrids with mismatches for both probe sets simultaneously.

In the cycle hybridization, all components are added before the cycling starts, at the 37° C. for T4, or a higher temperature for a thermostable ligase. Then the temperature is decreased to 15–37° C. and the chip is incubated for up to 10 minutes, and then the temperature is increased to 37° C. or higher for a few minutes and then again reduced. Cycles can be repeated up to 10 times. In one variant, an optimal higher temperature (10–50° C.) can be used without cycling and longer ligation reaction can be performed (1–3 hours).

The procedure described herein allows complex chip manufacturing using standard synthesis and precise spotting of oligonucleotides because a relatively small number of oligonucleotides are necessary. For example, if all 7-mer oligos are synthesized (16384 probes), lists of 256 million 4-mers can be determined.

One important variant of the invented method is to use more than one differently labeled probe per base array. This can be executed with two purposes in mind; multiplexing to reduce number of separately hybridized arrays; or to determine a list of even longer oligosequences such as 3×6 or 3×7. In this case, if two labels are used, the specificity of the 3 consecutive oligonucleotides can be almost absolute because positive sites must have enough signals of both labels.

A further and additional variant is to use chips containing BxNy probes with y being from 1 to 4. Those chips allow sequence reading in different frames. This can also be achieved by using appropriate sets of labeled probes or both F and P probes could have some unspecified end positions (i.e., some element of terminal degeneracy). Universal bases may also be employed as part of a linker to join the probes of defined sequence to the solid support. This makes the probe more available to hybridization and makes the construct more stable. If a probe has 5 bases, one may, e.g., use 3 universal bases as a linker.

EXAMPLE 16

Determining Sequence from Hybridization Data

Sequence assembly may be interrupted where ever a given overlapping (N–1) mer is duplicated two or more times. Then either of the two N-mers differing in the last nucleotide may be used in extending the sequence. This branching point limits unambiguous assembly of sequence.

Reassembling the sequence of known oligonucleotides that hybridize to the target nucleic acid to generate the complete sequence of the target nucleic acid may not be accomplished in some cases. This is because some information may be lost if the target nucleic acid is not in fragments of appropriate size in relation to the size of oligonucleotide that is used for hybridizing. The quantity of information lost is proportional to the length of a target being sequenced. However, if sufficiently short targets are used, their sequence may be unambiguously determined.

The probable frequency of duplicated sequences that would interfere with sequence assembly which is distributed along a certain length of DNA may be calculated. This derivation requires the introduction of the definition of a parameter having to do with sequence organization: the sequence subfragment (SF). A sequence subfragment results if any part of the sequence of a target nucleic acid starts and ends with an (N−1)mer that is repeated two or more times within the target sequence. Thus, subfragments are sequences generated between two points of branching in the process of assembly of the sequences in the method of the invention. The sum of all subfragments is longer than the actual target nucleic acid because of overlapping short ends. Generally, subfragments may not be assembled in a linear order without additional information since they have shared (N−1)mers at their ends and starts. Different numbers of subfragments are obtained for each nucleic acid target depending on the number of its repeated (N−1) mers. The number depends on the value of N−1 and the length of the target.

Probability calculations can estimate the interrelationship of the two factors. If the ordering of positive N-mers is accomplished by using overlapping sequences of length N−1 or at an average distance of $A_o$, the N−1 of a fragment Lf bases long is given by equation one:

$$N_{sf} = 1 + A_o \times K \times P(K, Lf)$$

Where K greater than or =2, and P (K, $L_f$) represents the probability of an N-mer occurring K-times on a fragment $L_f$ base long. Also, a computer program that is able to form subfragments from the content of N-mers for any given sequence is described below in Example 18.

The number of subfragments increases with the increase of lengths of fragments for a given length of probe. Obtained subfragments may not be uniquely ordered among themselves. Although not complete, this information is very useful for comparative sequence analysis and the recognition of functional sequence characteristics. This type of information may be called partial sequence. Another way of obtaining partial sequence is the use of only a subset of oligonucleotide probes of a given length.

There may be relatively good agreement between predicted sequence according to theory and a computer simulation for a random DNA sequence. For instance, for N−1=7, [using an 8-mer or groups of sixteen 10-mers of type 5' (A,T,C,G) $B_8$ (A,T,C,G) 3'] a target nucleic acid of 200 bases will have an average of three subfragments. However, because of the dispersion around the mean, a library of target nucleic acid should have inserts of 500 bp so that less than 1 in 2000 targets have more than three subfragments. Thus, in an ideal case of sequence determination of a long nucleic acid of random sequence, a representative library with sufficiently short inserts of target nucleic acid may be used. For such inserts, it is possible to reconstruct the individual target by the method of the invention. The entire sequence of a large nucleic acid is then obtained by overlapping of the defined individual insert sequences.

To reduce the need for very short fragments, e.g. 50 bases for 8-mer probes. The information contained in the overlapped fragments present in every random DNA fragmentation process like cloning, or random PCR is used. It is also possible to use pools of short physical nucleic acid fragments. Using 8-mers or 11-mers like 5' (A, T, C, G) $N_8$ (A, T, C, G)3' for sequencing 1 megabase, instead of needing 20,000 50 bp fragments only 2,100 samples are sufficient. This number consists of 700 random 7 kb clones (basic library), 1250 pools of 20 clones of 500 bp (subfragments ordering library) and 150 clones from jumping (or similar) library. The developed algorithm (see Example 18) regenerates sequence using hybridization data of these described samples.

EXAMPLE 17

Algorithm

This example describes an algorithm for generation of a long sequence written in a four letter alphabet from constituent k-tuple words in a minimal number of separate, randomly defined fragments of a starting nucleic acid sequence where K is the length of an oligonucleotide probe. The algorithm is primarily intended for use in the sequencing by hybridization (SBH) process. The algorithm is based on subfragments (SF), informative fragments (IF) and the possibility of using pools of physical nucleic sequences for defining informative fragments.

As described, subfragments may be caused by branch points in the assembly process resulting from the repetition of a K−1 oligomer sequence in a target nucleic acid. Subfragments are sequence fragments found between any two repetitive words of the length K−1 that occur in a sequence. Multiple occurrences of K−1 words are the cause of interruption of ordering the overlap of K-words in the process of sequence generation. Interruption leads to a sequence remaining in the form of subfragments. Thus, the unambiguous segments between branching points whose order is not uniquely determined are called sequence subfragments.

Informative fragments are defined as fragments of a sequence that are determined by the nearest ends of overlapped physical sequence fragments.

A certain number of physical fragments may be pooled without losing the possibility of defining informative fragments. The total length of randomly pooled fragments depends on the length of k-tuples that are used in the sequencing process.

The algorithm consists of two main units. The first part is used for generation of subfragments from the set of k-tuples contained in a sequence. Subfragments may be generated within the coding region of physical nucleic acid sequence of certain sizes, or within the informative fragments defined within long nucleic acid sequences. Both types of fragments are members of the basic library. This algorithm does not describe the determination of the content of the k-tuples of the informative fragments of the basic library, i.e. the step of preparation of informative fragments to be used in the sequence generation process.

The second part of the algorithm determines the linear order of obtained subfragments with the purpose of regenerating the complete sequence of the nucleic acid fragments of the basic library. For this purpose a second, ordering library is used, made of randomly pooled fragments of the starting sequence. The algorithm does not include the step of combining sequences of basic fragments to regenerate an entire, megabase plus sequence. This may be accomplished using the link-up of fragments of the basic library which is a prerequisite for informative fragment generation. Alternatively, it may be accomplished after generation of sequences of fragments of the basic library by this algorithm, using search for their overlap, based on the presence of common end-sequences.

The algorithm requires neither knowledge of the number of appearances of a given k-tuple in a nucleic acid sequence of the basic and ordering libraries, nor does it require the information of which k-tuple words are present on the ends of a fragment. The algorithm operates with the mixed content of k-tuples of various length. The concept of the algorithm enables operations with the k-tuple sets that contain false positive and false negative k-tuples. Only in specific cases does the content of the false k-tuples primarily influence the completeness and correctness of the generated sequence. The algorithm may be used for optimization of parameters in simulation experiments, as well as for sequence generation in the actual SBH experiments e.g. generation of the genomic DNA sequence. In optimization of parameters, the choice of the oligonucleotide probes (k-tuples) for practical and convenient fragments and/or the choice of the optimal lengths and the number of fragments for the defined probes are especially important.

This part of the algorithm has a central role in the process of the generation of the sequence from the content of k-tuples. It is based on the unique ordering of k-tuples by means of maximal overlap. The main obstacles in sequence generation are specific repeated sequences and false positive and/or negative k-tuples. The aim of this part of the algorithm is to obtain the minimal number of the longest possible subfragments, with correct sequence. This part of the algorithm consists of one basic, and several control steps. A two-stage process is necessary since certain information can be used only after generation of all primary subfragments.

The main problem of sequence generation is obtaining a repeated sequence from word contents that by definition do not carry information on the number of occurrences of the particular k-tuples. The concept of the entire algorithm depends on the basis on which this problem is solved. In principle, there are two opposite approaches: 1) repeated sequences may be obtained at the beginning, in the process of generation of pSFs, or 2) repeated sequences can be obtained later, in the process of the final ordering of the subfragments. In the first case, pSFs contain an excess of sequences and in the second case, they contain a deficit of sequences. The first approach requires elimination of the excess sequences generated, and the second requires permitting multiple use of some of the subfragments in the process of the final assembling of the sequence.

The difference in the two approaches in the degree of strictness of the rule of unique overlap of k-tuples. The less severe rule is: k-tuple X is unambiguously maximally overlapped with k-tuple Y if and only if, the rightmost k−1 end of k-tuple X is present only on the leftmost end of k-tuple Y. This rule allows the generation of repetitive sequences and the formation of surplus sequences.

A stricter rule which is used in the second approach has an addition caveat: k-tuple X is unambiguously maximally overlapped with k-tuple Y if and only if, the rightmost K−1 end of k-tuple X is present only on the leftmost end of k-tuple Y and if the leftmost K−1 end of k-tuple Y is not present on the rightmost end of any other k-tuple. The algorithm based on the stricter rule is simpler, and is described herein.

The process of elongation of a given subfragment is stopped when the right k−1 end of the last k-tuple included is not present on the left end of any k-tuple or is present on two or more k-tuples. If it is present on only one k-tuple the second part of the rule is tested. If in addition there is a k-tuple which differs from the previously included one, the assembly of the given subfragment is terminated only on the first leftmost position. If this additional k-tuple does not exist, the conditions are met for unique k−1 overlap and a given subfragment is extended to the right by one element.

Beside the basic rule, a supplementary one is used to allow the usage of k-tuples of different lengths. The maximal overlap is the length of k−1 of the shorter k-tuple of the overlapping pair. Generation of the pSFs is performed starting from the first k-tuple from the file in which k-tuples are displayed randomly and independently from their order in a nucleic acid sequence. Thus, the first k-tuple in the file is not necessarily on the beginning of the sequence, nor on the start of the particular subfragment. The process of subfragment generation is performed by ordering the k-tuples by means of unique overlap, which is defined by the described rule. Each used k-tuple is erased from the file. At the point when there are no further k-tuples unambiguously overlapping with the last one included, the building of subfragment is terminated and the buildup of another pSF is started. Since generation of a majority of subfragments does not begin from their actual starts, the formed pSF are added to the k-tuple file and are considered as a longer k-tuple. Another possibility is to form subfragments going in both directions from the starting k-tuple. The process ends when further overlap, i.e. the extension of any of the subfragments, is not possible.

The pSFs can be divided in three groups: 1) Subfragments of the maximal length and correct sequence in cases of exact k-tuple set; 2) short subfragments, formed due to the used of the maximal and unambiguous overlap rule on the incomplete set, and/or the set with some false positive k-tuples; and 3) pSFs of an incorrect sequence. The incompleteness of the set in 2) is caused by false negative results of a hybridization experiment, as well as by using an incorrect set of k-tuples. These are formed due to the false positive and false negative k-tuples and can be: a) misconnected subfragments; b) subfragments with the wrong end; and c) false positive k-tuples which appears as false minimal subfragments.

Considering false positive k-tuples, there is the possibility for the presence of a k-tuple containing more than one wrong base or containing one wrong base somewhere in the middle, as well as the possibility for a k-tuple with a wrong base on the end. Generation of short, erroneous or misconnected subfragments is caused by the latter k-tuples. The k-tuples of the former two kinds represent wrong pSFs with length equal to k-tuple length.

In the case of one false negative k-tuple, pSFs are generated because of the impossibility of maximal overlapping. In the case of the presence of one false positive k-tuple with the wrong base on its leftmost or rightmost end, pSFs are generated because of the impossibility of unambiguous overlapping. When both false positive and false negative k-tuples with a common k−1 sequence are present in the file, pSFs are generated, and one of these pSFs contains the wrong k-tuple at the relevant end.

The process of correcting subfragments with errors in sequence and the linking of unambiguously connected pSF is performed after subfragment generation and in the process of subfragment ordering. The first step which consists of cutting the misconnected pSFs and obtaining the final subfragments by unambiguous connection of pSFs is described below.

There are two approaches for the formation of misconnected subfragments. In the first a mistake occurs when an erroneous k-tuple appears on the points of assembly of the repeated sequences of lengths k−1. In the second, the repeated sequences are shorter than k−1. These situations can occur in two variants each. In the first variant, one of the repeated sequences represents the end of a fragment. In the second variant, the repeated sequence occurs at any position within the fragment. For the first possibility, the absence of some k-tuples from the file (false negatives) is required to generate a misconnection. The second possibility requires the presence of both false negative and false positive k-tuples in the file. Considering the repetitions of k−1 sequence, the lack of only one k-tuple is sufficient when either end is repeated internally. The lack of two is needed for strictly internal repetition. The reason is that the end of a sequence can be considered informatically as an endless linear array of false negative k-tuples. From the "smaller than k−1 case", only the repeated sequence of the length of k−2, which requires two or three specific erroneous k-tuples, will be considered. It is very likely that these will be the only cases which will be detected in a real experiment, the others being much less frequent.

Recognition of the misconnected subfragments is more strictly defined when a repeated sequence does not appear at the end of the fragment. In this situation, one can detect further two subfragments, one of which contains on its leftmost, and the other on its rightmost end k−2 sequences which are also present in the misconnected subfragment. When the repeated sequence is on the end of the fragment, there is only one subfragment which contains k−2 sequence causing the mistake in subfragment formation on its leftmost or rightmost end.

The removal of misconnected subframents by their cutting is performed according to the common rule: If the leftmost or rightmost sequence of the length of k−2 of any subfragments is present in any other subfragment, the subfragment is to be cut into two subfragments, each of them containing k−2 sequence. This rule does not cover rarer situations of a repeated end when there are more than one false negative k-tuple on the point of repeated k−1 sequence. Misconnected subfragments of this kind can be recognized by using the information from the overlapped fragments, or informative fragments of both the basic and ordering libraries. In addition, the misconnected subfragment will remain when two or more false negative k-tuples occur on both positions which contain the identical k−1 sequence. This is a very rare situation since it requires at least 4 specific false k-tuples. An additional rule can be introduced to cut these subfragments on sequences of length k if the given sequence can be obtained by combination of sequences shorter than k−2 from the end of one subfragment and the start of another.

By strict application of the described rule, some completeness is lost to ensure the accuracy of the output. Some of the subfragments will be cut although they are not misconnected since they fit into the pattern of a misconnected subfragment. There are several situations of this kind. For example, a fragment, beside at least two identical k−1 sequences, contains any k−2 sequence from k−1 or a fragment contains k−2 sequence repeated at least twice and at least one false negative k-tuple containing given k−1 sequence in the middle, etc.

The aim of this part of the algorithm is to reduce the number of pSFs to a minimal number of longer subfragments with correct sequence. The generation of unique longer subfragments or a complete sequence is possible in two situations. The first situation concerns the specific order of repeated k−1 words. There are cases in which some or all maximally extended pSFs (the first group of pSFs) can be uniquely ordered. For example, in fragment S-R1-a-R2-b-R1-c-R2-E where S and E are the start and end of a fragment, a, b, and c are different sequences specific to respective subfragments and R1 and R2 are two k−1 sequences that are tandemly repeated, five subfragments are generated (S-R1, R1-a-R2, R2-b-R1, R1-c-R2, and R-E). They may be ordered in two ways; the original sequence above or S-R1-c-R-b-R1-a-R-E. In contrast, in a fragment with the same number and types of repeated sequences but ordered differently, i.e. S-R1-a-R1-b-R-c-R-E, there is no other sequence which includes all subfragments. Examples of this type can be recognized only after the process of generation of pSFs. They represent the necessity for two steps in the process of pSF generation. The second situation of generation of false short subfragments on positions of nonrepeated k−1 sequences when the files contain false negative and/or positive k-tuples is more important.

The solution for both pSF groups consists of two parts. First, the false positive k-tuples appearing as the nonexisting minimal subfragments are eliminated. All k-tuple subfragments of length k which do not have an overlap on either end, of the length of longer than k−a on one end and longer than k−b on the other end, are eliminated to enable formation of the maximal number of connections. In our experiments, the values for a and b of 2 and 3, respectively, appeared to be adequate to eliminate a sufficient number of false positive k-tuples.

The merging of subfragments that can be uniquely connected is accomplished in the second step. The rule for connection is: two subfragments may be unambiguously connected if, and only if, the overlapping sequence at the relevant end or start of two subfragments is not present at the start and/or end of any other subfragment.

The exception is if one subfragment from the considered pair has the identical beginning and end. In that case connection is permitted, even if there is another subfragment with the same end present in the file. The main problem here is the precise definition of overlapping sequence. The connection is not permitted if the overlapping sequence unique for only one pair of subfragments is shorter than k−2, of it is k−2 or longer but an additional subfragment exists with the overlapping sequence of any length longer than k−4. Also, both the canonical ends of pSFs and the ends after omitting one (or few) last bases are considered as the overlapping sequences.

After this step some false positive k-tuples (as minimal subfragments) and some subfragments with a wrong end may survive. In addition, in very rare occasions where a certain number of some specific false k-tuples are simultaneously present, an erroneous connection may take place. These cases will be detected and solved in the subfragment ordering process, and in the additional control steps along with the handling of uncut "misconnected" subfragments.

The short subfragments that are obtained are of two kinds. In the common case, these subfragments may be unambiguously connected among themselves because of the distribution of repeated k−1 sequences. This may be done after the process of generation of pSFs and is a good example of the necessity for two steps in the process of pSF generation. In the case of using the file containing false positive and/or false negative k-tuples, short pSFs are obtained on the sites of nonrepeated k−1 sequences. Considering false positive k-tuples, a k-tuple may contain more than one wrong base (or containing one wrong base somewhere in the middle), as well as k-tuple on the end. Generation of short and erroneous (or misconnected) subfragments is caused by the latter k-tuples. The k-tuples of the former kind represent wrong pSFs with length equal to k-tuple length.

The aim of merging pSF part of the algorithm is the reduction of the number of pSFs to the minimal number of longer subfragments with the correct sequence. All k-tuple subfragments that do not have an overlap on either end, of the length of longer than k-a on one, and longer than k-b on the other end, are eliminated to enable the maximal number of connections. In this way, the majority of false positive k-tuples are discarded. The rule for connection is: two subfragments can be unambiguously connected if, and only if the overlapping sequence of the relevant end or start of two subfragments is not present on the start and/or end of any other subfragment. The exception is a subfragment with the identical beginning and end. In that case connection is permitted, provided that there is another subfragment with the same end present in the file. The main problem here is of precise definition of overlapping sequence. The presence of at least two specific false negative k-tuples on the points of repetition of k–1 or k–2 sequences, as well as combining of the false positive and false negative k-tuples may destroy or "mask" some overlapping sequences and can produce an unambiguous, but wrong connection of pSFs. To prevent this, completeness must be sacrificed on account of exactness: the connection is not permitted on the end-sequences shorter than k–2, and in the presence of an extra overlapping sequence longer than k–4. The overlapping sequences are defined from the end of the pSFs, or omitting one, or few last bases.

In the very rare situations, with the presence of a certain number of some specific false positive and false negative k-tuples, some subfragments with the wrong end can survive, some false positive k-tuples (as minimal subfragments) can remain, or the erroneous connection can take place. These cases are detected and solved in the subfragments ordering process, and in the additional control steps along with the handling of uncut, misconnected subfragments.

The process of ordering of subfragments is similar to the process of their generation. If one considers subfragments as longer k-tuples, ordering is performed by their unambiguous connection via overlapping ends. The informational basis for unambiguous connection is the division of subfragments generated in fragments of the basic library into groups representing segments of those fragments. The method is analogous to the biochemical solution of this problem based on hybridization with longer oligonucleotides with relevant connecting sequence. The connecting sequences are generated as subfragments using the k-tuple sets of the appropriate segments of basic library fragments. Relevant segments are defined by the fragments of the ordering library that overlap with the respective fragments of the basic library. The shortest segments are informative fragments of the ordering library. The longer ones are several neighboring informative fragments or total overlapping portions of fragments corresponding of the ordering and basic libraries. In order to decrease the number of separate samples, fragments of the ordering library are randomly pooled, and the unique k-tuple content is determined.

By using the large number of fragments in the ordering library very short segments are generated, thus reducing the chance of the multiple appearance of the k–1 sequences which are the reasons for generation of the subfragments. Furthermore, longer segments, consisting of the various regions of the given fragment of the basic library, do not contain some of the repeated k–1 sequences. In every segment a connecting sequence (a connecting subfragment) is generated for a certain pair of the subfragments from the given fragment. The process of ordering consists of three steps: (1) generation of the k-tuple contents of each segment; (2) generation of subfragments in each segment; and (3) connection of the subfragments of the segments. Primary segments are defined as significant intersections and differences of k-tuple contents of a given fragment of the basic library with the k-tuple contents of the pools of the ordering library. Secondary (shorter) segments are defined as intersections and differences of the k-tuple contents of the primary segments.

There is a problem of accumulating both false positive and negative k-tuples in both the differences and intersections. The false negative k-tuples from starting sequences accumulate in the intersections (overlapping parts), as well as false positive k-tuples occurring randomly in both sequences, but not in the relevant overlapping region. On the other hand, the majority of false positives from either of the starting sequences is not taken up into intersections. This is an example of the reduction of experimental errors from individual fragments by using information from fragments overlapping with them. The false k- tuples accumulate in the differences for another reason. The set of false negatives from the original sequences are enlarged for false positives from intersections and the set of false positives for those k-tuples which are not included in the intersection by error, i.e. are false negative in the intersection. If the starting sequences contain 10% false negative data, the primary and secondary intersections will contain 19% and 28% false negative k-tuples, respectively. On the other hand, a mathematical expectation of 77 false positives may be predicted if the basic fragment and the pools have lengths of 500 bp and 10,000 bp, respectively. However, there is a possibility of recovering most of the "lost" k-tuples and of eliminating most of the false positive k-tuples.

First, one has to determine a basic content of the k-tuples for a given segment as the intersection of a given pair of the k-tuple contents. This is followed by including all k-tuples of the starting k-tuple contents in the intersection, which contain at one end k–1 and at the other end k–+ sequences which occur at the ends of two k-tuples of the basic set. This is done before generation of the differences thus preventing the accumulation of false positives in that process. Following that, the same type of enlargement of k-tuple set is applied to differences with the distinction that the borrowing is from the intersections. All borrowed k-tuples are eliminated from the intersection files as false positives.

The intersection, i.e. a set of common k-tuples, is defined for each pair (a basic fragment)×(a pool of ordering library). If the number of k-tuples in the set is significant it is enlarged with the false negatives according to the described rule. The primary difference set is obtained by subtracting from a given basic fragment the obtained intersection set. The false negative k-tuples are appended to the difference set by borrowing from the intersection set according to the described rule and, at the same time, removed from the intersection set as false positive k-tuples. When the basic fragment is longer than the pooled fragments, this difference can represent the two separate segments which somewhat reduces its utility in further steps. The primary segments are all generated intersections and differences of pairs (a basic fragment)×(a pool of ordering library) containing the significant number of k-tuples. K-tuple sets of secondary segments are obtained by comparison of k-tuple sets of all possible pairs of primary segments. The two differences are defined from each pair which produces the intersection with the significant number of k-tuples. The majority of available information from overlapped fragments is recovered in this step so that there is little to be gained from the third round of forming intersections. and differences.

(2) Generation of the subfragments of the segments is performed identically as described for the fragments of the basic library.

(3) The method of connection of subfragments consists of sequentially determining the correctly linked pairs of subfragments among the subfragments from a given basic library fragment which have some overlapped ends. In the case of 4 relevant subfragments, two of which contain the same beginning and two having the same end, there are 4 different pairs of subfragments that can be connected. In general 2 are correct and 2 are wrong. To find correct ones, the presence of the connecting sequences of each pair is tested in the subfragments generated from all primary and secondary segments for a given basic fragment. The length and the position of the connecting sequence are chosen to avoid interference with sequences which occur by chance. They are k+2 or longer, and include at least one element 2 beside overlapping sequence in both subfragments of a given pair. The connection is permitted only if the two connecting sequences are found and the remaining two do not exist. The two linked subfragments replace former subfragments in the file and the process is cyclically repeated.

Repeated sequences are generated in this step. This means that some subfragments are included in linked subfragments more than once. They will be recognized by finding the relevant connecting sequence which engages one subfragment in connection with two different subfragments.

The recognition of misconnected subfragments generated in the processes of building pSFs and merging pSFs into longer subfragments is based on testing whether the sequences of subfragments from a given basic fragment exist in the sequences of subfragments generated in the segments for the fragment. The sequences from an incorrectly connected position will not be found indicating the misconnected subfragments.

Beside the described three steps in ordering of subfragments some additional control steps or steps applicable to specific sequences will be necessary for the generation of more complete sequence without mistakes.

The determination of which subfragment belongs to which segment is performed b comparison of contents of k-tuples in segments and subfragments. Because of the errors in the k-tuple contents (due to the primary error in pools and statistical errors due to the frequency of occurrences of k-tuples) the exact partitioning of subfragments is impossible. Thus, instead of "all or none" partition, the chance of coming from the given segment (P(sf,s)) is determined for each subfragment. This possibility is the function of the lengths of k-tuples, the lengths of subfragments, the lengths of fragments of ordering library, the size of the pool, and of the percentage of false k-tuples in the file:

$$P(sf,s)=(Ck-F)/Lsf,$$

where Lsf is the length of subfragment, Ck is the number of common k-tuples for a given subfragment/segment pair and F is the parameter that includes relations between lengths of k-tuples, fragments of basic library, the size of the pool, and the error percentage.

Subfragments attributed to a particular segment are treated as redundant short pSFs and are submitted to a process of unambiguous connection. The definition of unambiguous connection is slightly different in this case, since it is based on a probability that subfragments with overlapping end(s) belong to the segment considered. Besides, the accuracy of unambiguous connection is controlled by following the connection of these subfragments in other segments. After the connection in different segments, all of the obtained subfragments are merged together, shorter subfragments included within longer ones are eliminated, and the remaining ones are submitted to the ordinary connecting process. If the sequence is not regenerated completely, the process of partition and connection of subfragments is repeated with the same or less severe criterions of probability of belonging to the particular segment, followed by unambiguous connection.

Using severe criteria for defining unambiguous overlap, some information is not used. Instead of a complete sequence, several subfragments that define a number of possibilities for a given fragment are obtained. Using less severe criteria an accurate and complete sequence is generated. In a certain number of situations, e.g. an erroneous connection, it is possible to generate a complete, but an incorrect sequence, or to generate "monster" subfragments with no connection among them. Thus, for each fragment of the basic library one obtains: a) several possible solutions where one is correct and b) the most probable correct solution. Also, in a very small number of cases, due to the mistake in the subfragment generation process or due to the specific ratio of the probabilities of belonging, no unambiguous solution is generated or one, the most probable solution. These cases remain as incomplete sequences, or the unambiguous solution is obtained by comparing these data with other, overlapped fragments of basic library.

The described algorithm was tested on a randomly generated, 50 kb sequence, containing 40% GC to simulate the GC content of the human genome. In the middle part of this sequence were inserted various All, and some other repetitive sequences, of a total length of about 4 kb. To simulate an in vitro SBH experiment, the following operations were performed to prepare appropriate data.

Positions of sixty 5 kb overlapping "clones" were randomly defined, to simulate preparation of a basic library:

Positions of one thousand 500 bp "clones" were randomly determined to simulate making the ordering library. These fragments were extracted from the sequence. Random pools of 20 fragments were made, and k-tuple sets of pools were determined and stored on the hard disk. These data are used in the subfragment ordering phase: For the same density of clones 4 million clones in basic library and 3 million clones in ordering library are used for the entire human genome. The total number of 7 million clones is several fold smaller than the number of clones a few kb long for random cloning of almost all of genomic DNA and sequencing by a gel-based method.

From the data on the starts and ends of 5 kb fragments, 117 "informative fragments" were determined to be in the sequence. This was followed by determination of sets of overlapping k-tuples of which the single "informative fragment" consist. Only the subset of k-tuples matching a predetermined list were used. The list contained 65% 8-mers, 30% 9-mers, and 5% 10–12-mers. Processes of generation and the ordering of subfragments were performed on these data.

The testing of the algorithm was performed on the simulated data in two experiments. The sequence of 50 informative fragments was regenerated with the 100% correct data set (over 20,000 bp), and 26 informative fragments (about 10,000 bp) with 10% false k-tuples (5% positive and 5% negative ones).

In the first experiment, all subfragments were correct and in only one out of 50 informative fragments the sequence was not completely regenerated but remained in the form of 5 subfragments. The analysis of positions of overlapped fragments of ordering library has shown that they lack the information for the unique ordering of the 5 subfragments. The subfragments may be connected in two ways based on overlapping ends, 1-2-3-4-5 and 1-4-3-2-5. The only the exchange of positions of subfragments 2 and 4. Since subfragments 2, 3, and 4 are relatively short (total of about 100 bp), the relatively greater chance existed, and occurred in this case, that none of the fragments of ordering library started or ended in the subfragment 3 region.

To simulate real sequencing, some false ("hybridization") data was included as input in a number of experiments. In oligomer hybridization experiments, under proposed conditions, the only situation producing unreliable data is the end mismatch versus full match hybridization. Therefore, in simulation only those k-tuples differing in a single element on either end from the real one were considered to be false positives. These "false" sets are made as follows. On the original set of a k-tuples of the informative fragment, a subset of 5% false positive k-tuples are added. False positive k-tuples are made by randomly picking a k-tuple from the set, copying it and altering a nucleotide on its beginning or end. This is followed by subtraction of a subset of 5% randomly chosen k-tuples. In this way the statistically expected number of the most complicated cases is generated in which the correct k-tuple is replaced with a k-tuple with the wrong base on the end.

Production of k-tuple sets as described leads to up to 10% of false data. This value varies from case to case, due to the randomness of choice of k-tuples to be copied altered, and erased. Nevertheless, this percentage 3–4 times exceeds the amount of unreliable data in real hybridization experiments. The introduced error of 10% leads to the two fold increase in the number of subfragments both in fragments of basic library (basic library informative fragments) and in segments. About 10% of the final subfragments have a wrong base at the end as expected for the k-tuple set which contains false positives (see generation of primary subfragments). Neither the cases of misconnection of subfragments nor subfragments with the wrong sequence were observed. In 4 informative fragments out of 26 examined in the ordering process the complete sequence was not regenerated. In all 4 cases the sequence was obtained in the form of several longer subfragments and several shorter subfragments contained in the same segment. This result shows that the algorithmic principles allow working with a large percentage of false data.

The success of the generation of the sequence from its k-tuple content may be described in terms of completeness and accuracy. In the process of generation, two particular situations can be defined: 1) Some part of the information is missing in the generated sequence, but one knows where the ambiguities are and to which type they belong, and 2) the regenerated sequence that is obtained does not match the sequence from which the k-tuple content is generated, but the mistake can not be detected. Assuming the algorithm is developed to its theoretical limits, as in the use of the exact k-tuple sets, only the first situation can take place. There the incompleteness results in a certain number of subfragments that may not be ordered unambiguously and the problem of determination of the exact length of monotonous sequences, i.e. the number of perfect tandem repeats.

With false k-tuples, incorrect sequence may be generated. The reason for mistakes does not lie in the shortcomings of the algorithm, but in the fact that a given content of k-tuples unambiguously represents the sequence that differs from the original one. One may define three classes of error, depending on the kind of the false k-tuples present in the file. False negative k-tuples (which are not accompanied with the false positives) produce "deletions". False positive k-tuples are producing "elongations (unequal crossing over)". False positives accompanied with false negatives are the reason for generation of "insertions", alone or combined with "deletions". The deletions are produced when all of the k-tuples (or their majority) between two possible starts of the subfragments are false negatives. Since every position in the sequence is defined by k k-tuples, the occurrence of the deletions in a common case requires k consecutive false negatives. (With 10% of the false negatives and k=8, this situation takes place after every 108 elements). This situation is extremely infrequent even in mammalian genome sequencing using random libraries containing ten genome equivalents.

Elongation of the end of the sequence caused by false positive k-tuples is the special case of "insertions", since the end of the sequence can be considered as the endless linear array of false negative k-tuples. One may consider a group of false positive k-tuples producing subfragments longer than one k-tuple. Situations of this kind may be detected if subfragments are generated in overlapped fragments, like random physical fragments of the ordering library. An insertion, or insertion in place of a deletion, can arise as a result of specific combinations of false positive and false negative k-tuples. In the first case, the number of consecutive false negatives is smaller than k. Both cases require several overlapping false positive k-tuples. The insertions and deletions are mostly theoretical possibilities without sizable practical repercussions since the requirements in the number and specificity of false k-tuples are simply too high.

In every other situation of not meeting the theoretical requirement of the minimal number an the kind of the false positive and/or negatives, mistakes in the k-tuples content may produce only the lesser completeness of a generated sequence.

SBH, a sample nucleic acid is sequenced by exposing the sample to a support-bound probe of known sequence and a labeled probe or probes in solution. Wherever the probes ligase is introduced into the mixture of probes and sample, such that, wherever a support has a bound probe and a labeled probe hybridized back to back along the sample, the two probes will be chemically linked by the action of the ligase. After washing, only chemically linked support-bound and labeled probes are detected by the presence of the labeled probe. By knowing the identity of the support-bound probe at a particular location in an array, and the identity of the labeled probe, a portion of the sequence of the sample may be determined by the presence of a label at a point in an array on a Format with a sample of three substrate. And not chances not working are maximally overlapping sequences of all of the ligated probe pairs, the sequence of the sample may be reconstructed. Not of the sample to be sequenced may be a nucleic acid fragment or oligonucleotide of ten base pairs ("bp"). The sample is preferably four to one thousand bases in length.

The length of the probe is a fragment less than ten bases in length, and, preferably, is between four and nine bases in length. In this way, arrays of support-bound probes may include all oligonucleotides of a given length or may include only oligonucleotides selected for a particular test. Where all oligonucleotides of a given length are used, the number of central oligonucleotides may be calculated by $4^N$ where N is the length of the probe.

EXAMPLE 18

Re-Using Sequencing Chips

When ligation is employed in the sequencing process, then the ordinary oligonucleotide chip cannot be immediately reused. The inventor contemplates that this may be overcome in various ways.

One may employ ribonucleotides for the second probe, probe P, so that this probe may subsequently be removed by RNAse treatment. RNAse treatment may utilize RNAse A an endoribonuclease that specifically attacks single-stranded RNA 3 to pyrimidine residues and cleaves the phosphate linkage to the adjacent nucleotide. The end products are pyrimidine 3 phosphates and oligonucleotides with terminal pyrimidine 3 phosphates. RNAse A works in the absence of cofactors and divalent cations.

To utilize an RNAse, one would generally incubate the chip in any appropriate RNAse-containing buffer, as described by Sambrook et al. (1989; incorporated herein by reference). The use of 30–50 ul of RNAse-containing buffer per 8x8 mm or 9x9 mm array at 37° C. for between 10 and 60 minutes is appropriate. One would then wash with hybridization buffer.

Although not widely applicable, one could also use the uracil base, as described by Craig et al. (1989), incorporated herein by reference, in specific embodiments. Destruction of the ligated probe combination, to yield a re-usable chip, would be achieved by digestion with the E. Coli repair enzyme, uracil-DNA glycosylase which removes uracil from DNA.

One could also generate a specifically cleavable bond between the probes and then cleave the bond after detection. For example, this may be achieved by chemical ligation as described by Shabarova et al., (1991) and Dolinnaya et al., (1988), both references being specifically incorporated herein by reference.

Shabarova et al. (1991) describe the condensation of oligodeoxyribo nucleotides with cyanogen bromide as a condensing agent. In their one step chemical ligation reaction, the oligonucleotides are heated to 97° C., slowly cooled to 0° C., then 1 ul 10 mM BrCN in acetonitrile is added.

Dolinnaya et al. (1988) show how to incorporate phosphoramidiate and pyrophosphate internucleotide bonds in DNA duplexes. They also use a chemical ligation method for modification of the sugar phosphate backbone of DNA, with a water-soluble carbodiimide (CDI) as a coupling agent. The selective cleavage of a phosphoamide bond involves contact with 15% $CH_3COOH$ for 5 min at 95° C. The selective cleavage of a pyrophosphate bond involves contact with a pyridine-water mixture (9:1) and freshly distilled $(CF_3CO)_2O$.

EXAMPLE 19

Diagnostics—Scoring Known Mutations or Full Gene Resequencing

In a simple case, the goal may be to discover whether selected, known mutations occur in a DNA segment. Less than 12 probes may suffice for this purpose, for example, 5 probes positive for one allele, 5 positive for the other, and 2 negative for both. Because of the small number of probes to be scored per sample, large numbers of samples may be analyzed in parallel. For example, with 12 probes in 3 hybridization cycles, 96 different genomic loci or gene segments from 64 patient may be analyzed on one 6x9 in membrane containing 12x24 subarrays each with 64 dots representing the same DNA segment from 64 patients. In this example, samples may be prepared in sixty-four 96-well plates. Each plate may represent one patient, and each well may represent one of the DNA segments to be analyzed. The samples from 64 plates may be spotted in four replicas as four quarters of the same membrane.

A set of 12 probes may be selected by single channel pipetting or by a single pin transferring device (or by an array of individually-controlled pipets or pins) for each of the 96 segments, and the selected probes may be arrayed in twelve 96-well plates. Probes may be labelled, if they are not prelabelled, and then probes from four plates may be mixed with hybridization buffer and added to the subarrays preferentially by a 96-channel pipeting device. After one hybridization cycle it is possible to strip off previously-applied probes by incubating the membrane at 37° to 55° C. in the preferably undiluted hybridization or washing buffer.

The likelihood that probes positive for one allele are positive and probes positive for the other allele are negative may be used to determine which of the two alleles is present. In this redundant scoring scheme, some level (about 10%) of errors in hybridization of each probe may be tolerated.

An incomplete set of probes may be used for scoring most of the alleles, especially if the smaller redundancy is sufficient, e.g. one or two probes which prove the presence or absence in a sample of one of the two alleles. For example, with a set of four thousand 8-mers there is a 91% chance of finding at least one positive probe for one of the two alleles for a randomly selected locus. The incomplete set of probes may be optimized to reflect G+C content and other biases in the analyzed samples.

For full gene sequencing, genes may be amplified in an appropriate number of segments. For each segment, a set of probes (about one probe per 2–4 bases) may be selected and hybridized. These probes may identify whether there is a mutation anywhere in the analyzed segments. Segments (i.e., subarrays which contain these segments) where one or more mutated sites are detected may be hybridized with additional probes to find the exact sequence at the mutated sites. If a DNA sample is tested by every second 6-mer, and a mutation is localized at the position that is surrounded by positively hybridized probes TGCAAA and TATTCC and covered by three negative probes: CAAAAC, AAACTA and ACTATT, the mutated nucleotides must be A and/or C occurring in the normal sequence at that position. They may be changed by a single base mutation, or by a one or two nucleotide deletion and/or insertion between bases AA, AC or CT.

One approach is to select a probe that extends the positively hybridized probe TGCAAA for one nucleotide to the right, and which extends the probe TATTCC one nucleotide to the left. With these 8 probes (GCAAAA, GCAAAT, GCAAAC, GCAAAG and ATATTC, TTATTC, CTATTC, GTATTC) two questionable nucleotides are determined.

The most likely hypothesis about the mutation may be determined. For example, A is found to be mutated to G. There are two solutions satisfied by these results. Either replacement of A with G is the only change or there is in addition to that change an insertion of some number of bases between newly determined G and the following C. If the result with bridging probes is negative these options may then be checked first by at least one bridging probe comprising the mutated position (AAGCTA) and with an additional 8 probes: CAAAGA, CAAAGT, CAAAGC, CAAAGG and ACTATT, TCTATT, CCTATT, GCTATT, I There are many other ways to select mutation-solving probes.

In the case of diploid, particular comparisons of scores for the test samples and homozygotic control may be performed to identify heterozygotes (see above). A few consecutive probes are expected to have roughly twice smaller signals if the segment covered by these probes is mutated on one of the two chromosomes.

EXAMPLE 20

Identification of Genes (Mutations) Responsible for Genetic Disorders and Other Traits Using universal sets of longer probes (8-mers or 9-mers) on immobilized arrays of samples, DNA fragments as long as 5–20 kb may be sequenced without subcloning. Furthermore, the speed of sequencing readily may be about 10 million bp/day/hybridization instrument. This performance allows for resequencing a large fraction of human genes or the human genome repeatedly from scientifically or medically interesting individuals. To resequence 50% of the human genes, about 100 million bp is checked. That may be done in a relatively short period of time at an affordable cost.

This enormous resequencing capability may be used in several ways to identify mutations and/or genes that encode for disorders or any other traits. Basically, mRNAs (which may be converted into cDNAs) from particular tissues or genomic DNA of patients with particular disorders may be used as starting materials. From both sources of DNA, separate genes or genomic fragments of appropriate length may be prepared either by cloning procedures or by in vitro amplification procedures (for example by PCR). If cloning is used, the minimal set of clones to be analyzed may be selected from the libraries before sequencing. That may be done efficiently by hybridization of a small number of probes, especially if a small number of clones longer than 5 kb is to be sorted. Cloning may increase the amount of hybridization data about two times, but does not require tens of thousands of PCR primers.

In one variant of the procedure, gene or genomic fragments may be prepared by restriction cutting with enzymes like Hga I which cuts DNA in following way: GACGC(N5')/ CTGCG(N10'). Protruding ends of five bases are different for different fragments. One enzyme produces appropriate fragments for a certain number of genes. By cutting cDNA or genomic DNA with several enzymes in separate reactions, every gene of interest may be excised appropriately. In one approach, the cut DNA is fractionated by size. DNA fragments prepared in this way (and optionally treated with Exonuclease III which individually removes nucleotides from the 3' end and increases length and specificity of the ends) may be dispensed in the tubes or in multiwell plates. From a relatively small set of DNA adapters with a common portion and a variable protruding end of appropriate length, a pair of adapters may be selected for every gene fragment that needs to be amplified. These adapters are ligated and then PCR is performed by universal primers. From 1000 adapters, a million pairs may be generated, thus a million different fragments may be specifically amplified in the identical conditions with a universal pair of primers complementary to the common end of the adapters.

If a DNA difference is found to be repeated in several patients, and that sequence change is nonsense or can change function of the corresponding protein, then the mutated gene may be responsible for the disorder. By analyzing a significant number of individuals with particular traits, functional allelic variations of particular genes could be associated by specific traits.

This approach may be used to eliminate the need for very expensive genetic mapping on extensive pedigrees and has special value when there is no such genetic data or material.

EXAMPLE 21

Scoring Single Nucleotide Polymorphisms in Genetic Mapping

Techniques disclosed in this application are appropriate for an efficient identification of genomic fragments with single nucleotide polymorphisms (SNUPs). In 10 individuals by applying the described sequencing process on a large number of genomic fragments of known sequence that may be amplified by cloning or by in vitro amplification, a sufficient number of DNA segments with SNUPs may be identified. The polymorphic fragments are further used as SNUP markers. These markers are either mapped previously (for example they represent mapped STSs) or they may be mapped through the screening procedure described below.

SNUPs may be scored in every individual from relevant families or populations by amplifying markers and arraying them in the form of the array of subarrays. Subarrays contain the same marker amplified from the analyzed individuals. For each marker, as in the diagnostics of known mutations, a set of 6 or less probes positive for one allele and 6 or less probes positive for the other allele may be selected and scored. From the significant association of one or a group of the markers with the disorder, chromosomal position of the responsible gene(s) may be determined. Because of the high throughput and low cost, thousands of markers may be scored for thousands of individuals. This amount of data allows localization of a gene at a resolution level of less than one million bp as well as localization of genes involved in polygenic diseases. Localized genes may be identified by sequencing particular regions from relevant normal and affected individuals to score a mutation(s).

PCR is preferred for amplification of markers from genomic DNA. Each of the markers require a specific pair of primers. The existing markers may be convertible or new markers may be defined which may be prepared by cutting genomic DNA by Hga I type restriction enzymes, and by ligation with a pair of adapters.

SNUP markers can be amplified or spotted as pools to reduce the number of independent amplification reactions. In this case, more probes are scored per one sample. When 4 markers are pooled and spotted on 12 replica membranes, then 48 probes (12 per marker) may be scored in 4 cycles.

EXAMPLE 22

Detection and Verification of Identity of DNA Fragments

DNA fragments generated by restriction cutting, cloning or in vitro amplification (e.g. PCR) frequently may be identified in a experiment. Identification may be performed by verifying the presence of a DNA band of specific size on gel electrophoresis. Alternatively, a specific oligonucleotide may be prepared and used to verify a DNA sample in question by hybridization. The procedure developed here allows for more efficient identification of a large number of samples without preparing a specific oligonucleotide for each fragment. A set of positive and negative probes may be selected from the universal set for each fragment on the basis of the known sequences. Probes that are selected to be positive usually are able to form one or a few overlapping groups and negative probes are spread over the whole insert.

This technology may be used for identification of STSs in the process of their mapping on the YAC clones. Each of the STSs may be tested on about 100 YAC clones or pools of YAC clones. DNAs from these 100 reactions possibly are spotted in one subarray. Different STSs may represent consecutive subarrays. In several hybridization cycles, a signature may be generated for each of the DNA samples, which signature proves or disproves existence of the particular STS in the given YAC clone with necessary confidence.

To reduce the number of independent PCR reactions or the number of independent samples for spotting, several STSs may be amplified simultaneously in a reaction or PCR samples may be mixed, respectively. In this case more probes have to be scored per one dot. The pooling of STSs is independent of pooling YACs and may be used on single YACs or pools of YACs. This scheme is especially attractive when several probes labelled with different colors are hybridized together.

In addition to confirmation of the existence of a DNA fragment in a sample, the amount of DNA may be estimated using intensities of the hybridization of several separate probes or one or more pools of probes. By comparing obtained intensities with intensities for control samples having a known amount of DNA, the quantity of DNA in all spotted samples is determined simultaneously. Because only a few probes are necessary for identification of a DNA fragment, and there are N possible probes that may be used for DNA N bases long, this application does not require a large set of probes to be sufficient for identification of any DNA segment. From one thousand 8-mers, on average about 30 full matching probes may be selected for a 1000 bp fragment.

EXAMPLE 23

Identification of Infectious Disease Organisms and their Variants

DNA-based tests for the detection of viral, bacterial, fungal and other parasitic organisms in patients are usually more reliable and less expensive than alternatives. The major advantage of DNA tests is to be able to identify specific strains and mutants, and eventually be able to apply more effective treatment. Two applications are described below.

The presence of 12 known antibiotic resistance genes in bacterial infections may be tested by amplifying these genes. The amplified products from 128 patients may be spotted in two subarrays and 24 subarrays for 12 genes may then be repeated four times on a 8×12 cm membrane. For each gene, 12 probes may be selected for positive and negative scoring. Hybridizations may be performed in 3 cycles. For these tests, a much smaller set of probes is most likely to be universal. For example, from a set of one thousand 8-mers, on average 30 probes are positive in 1000 bp fragments, and 10 positive probes are usually sufficient for a highly reliable identification. As described in Example 9, several genes may be amplified and/or spotted together and the amount of the given DNA may be determined. The amount of amplified gene may be used as an indicator of the level of infection.

Another example involves possible sequencing of one gene or the whole genome of an HIV virus. Because of rapid diversification, the virus poses many difficulties for selection of an optimal therapy. DNA fragments may be amplified from isolated viruses from up to 64 patients and resequenced by the described procedure. On the basis of the obtained sequence the optimal therapy may be selected. If there is a mixture of two virus types of which one has the basic sequence (similar to the case of heterozygotes), the mutant may be identified by quantitative comparisons of its hybridization scores with scores of other samples, especially control samples containing the basic virus type only. Scores twice as small may be obtained for three to four probes that cover the site mutated in one of the two virus types present in the sample (see above).

EXAMPLE 24

Forensic and Parental Identification

Sequence polymorphisms make an individual genomic DNA unique. This permits analysis of blood or other body fluids or tissues from a crime scene and comparison with samples from criminal suspects. A sufficient number of polymorphic sites are scored to produce a unique signature of a sample. SBH may easily score single nucleotide polymorphisms to produce such signatures.

A set of DNA fragments (10–1000) may be amplified from samples and suspects. DNAs from samples and suspects representing one fragment are spotted in one or several subarrays and each subarray may be replicated 4 times. In three cycles, 12 probes may determine the presence of allele A or B in each of the samples, including suspects, for each DNA locus. Matching the patterns of samples and suspects may lead to discovery of the suspect responsible for the crime.

The same procedure may be applicable to prove or disprove the identity of parents of a child. DNA may be prepared and polymorphic loci amplified from the child and adults; patterns of A or B alleles may be determined by hybridization for each. Comparisons of the obtained patterns, along with positive and negative controls, aide in the determination of familial relationships. In this case, only a significant portion of the alleles need match with one parent for identification. Large numbers of scored loci allow for the avoidance of statistical errors in the procedure or of masking effects of de novo mutations.

EXAMPLE 25

Assessing Genetic Diversity of Populations or Species and Biological Diversity of Ecological Niches Measuring the frequency of allelic variations on a significant number of loci (for example, several genes or entire mitochondrial DNA) permits development of different types of conclusions, such as conclusions regarding the impact of the environment on the genotypes, history and evolution of a population or its susceptibility to diseases or extinction, and others. These assessments may be performed by testing specific known alleles or by full resequencing of some loci to be able to define de novo mutations which may reveal fine variations or presence of mutagens in the environment.

Additionally, biodiversity in the microbial world may be surveyed by resequencing evolutionarily conserved DNA sequences, such as the genes for ribosomal RNAs or genes for highly conservative proteins. DNA may be prepared from the environment and particular genes amplified using primers corresponding to conservative sequences. DNA fragments may be cloned preferentially in a plasmid vector (or diluted to the level of one molecule per well in multiwell plates and than amplified in vitro). Clones prepared this way may be resequenced as described above. Two types of information are obtained. First of all, a catalogue of different species may be defined as well as the density of the individuals for each species. Another segment of information may be used to measure the influence of ecological factors or pollution on the ecosystem. It may reveal whether some species are eradicated or whether the abundance ratios among species is altered due to the pollution. The method also is applicable for sequencing DNAs from fossils.

EXAMPLE 26

Detection or Quantification of Nucleic Acid Species

DNA or RNA species may be detected and quantified by employing a probe pair including an unlabeled probe fixed to a substrate and a labeled probe in a solution. The species may be detected and quantified by exposure to the unlabeled probe in the presence of the labeled probe and ligase. Specifically, the formation of an extended probe by ligation of the labeled and unlabeled probe on the sample nucleic acid backbone is indicative of the presence of the species to be detected. Thus, the presence of label at a specific point in the array on the substrate after removing unligated labeled probe indicates the presence of a sample species while the quantity of label indicates the expression level of the species.

Alternatively, one or more unlabeled probes may be arrayed on a substrate as first members of pairs with one or more labeled probes to be introduced in solution. According to one method, multiplexing of the label on the array may be carried out by using dyes which fluoresce at distinguishable wavelengths. In this manner, a mixture of cDNAs applied to an array with pairs of labeled and unlabeled probes specific for species to be identified may be examined for the presence of and expression level of cDNA species. According to a preferred embodiment this approach may be carried out to sequence portions of cDNAs by selecting pairs of unlabeled and labeled probes pairs comprising sequences which overlap along the sequence of a cDNA to be detected.

Probes may be selected to detect the presence and quantity of particular pathogenic organisms genome by including in the composition selected probe pairs which appear in combination only in target pathogenic genome organisms. Thus, while no single probe pair may necessarily be specific for the pathogenic organism genome, the combination of pairs is. Similarly, in detecting or sequencing cDNAs, it might occur that a particular probe is not be specific for a cDNA or other type of species. Nevertheless, the presence and quantity of a particular species may be determined by a result wherein a combination of selected probes situated at distinct array locations is indicative of the presence of a particular species.

An infectious agent with about 10 kb or more of DNA may be detected using a support-bound detection chip without the use of polymerase chain reaction (PCR) or other target amplification procedures. According to other methods, the genomes of infectious agents including bacteria and viruses are assayed by amplification of a single target nucleotide sequence through PCR and detection of the presence of target by hybridization of a labelled probe specific for the target sequence. Because such an assay is specific for only a single target sequence it therefore is necessary to amplify the gene by methods such as PCR to provide sufficient target to provide a detectable signal.

According to this example, an improved method of detecting nucleotide sequences characteristic of infectious agents through a Format 3-type reaction is provided wherein a solid phase detection chip is prepared which comprises an array of multiple different immobilized oligonucleotide probes specific for the infectious agent of interest. A single dot comprising a mixture of many unlabeled probes complementary to the target nucleic acid concentrates the label specific to a species at one location thereby improving sensitivity over diffuse or single probe labeling. Such multiple probes may be of overlapping sequences of the target nucleotide sequence but may also be non-overlapping sequences as well as non-adjacent. Such probes preferably have a length of about 5 to 12 nucleotides.

A nucleic acid sample exposed to the probe array and target sequences present in the sample will hybridize with the multiple immobilized probes. A pool of multiple labeled probes selected to specifically bind to the target sequences adjacent to the immobilized probes is then applied with the sample to an array of unlabeled oligonucleotide probe mixtures. Ligase enzyme is then applied to the chip to ligate the adjacent probes on the sample. The detection chip is then washed to remove unhybridized and unligated probe and sample nucleic acids and the presence of sample nucleic acid may be determined by the presence or absence of label. This method provides reliable sample detection with about a 1000-fold reduction of molarity of the sample agent.

As a further aspect of the invention, the signal of the labelled probes may be amplified by means such as providing a common tail to the free probe which itself comprises multiple chromogenic, enzymatic or radioactive labels or which is itself susceptible to specific binding by a further probe agent which is multiply labelled. In this way, a second round of signal amplification may be carried out. Labeled or unlabeled probes may be used in a second round of amplification. In this second round of amplification, a lengthy DNA sample with multiple labels may result in an increased amplification intensity signal between 10 to 100 fold which may result in a total signal amplification of 100,000 fold. Through the use of both aspects of this example, an intensity signal approximately 100,000 fold may give a positive result of probe-DNA ligation without having to employ PCR or other amplification procedures.

According to a further aspect of the invention an array or super array may be prepared which consists of a complete set of probes, for example 4096 6-mer probes. Arrays of this type are universal in a sense that they can be used for detection or partial to complete sequencing of any nucleic acid species. Individual spots in an array may contain single probe species or mixtures of probes, for example N(1–3) B(4–6) N(1–b 3) type of mixtures that are synthesized in the single reaction (N represents all four nucleotides, B one specific nucleotide and where the associated numbers are a range of numbers of bases i.e., 1–3 means "from one to three bases".) These mixtures provide stronger signal for a nucleic acid species present at low concentration by collecting signal from different parts of the same long nucleic acid species molecule. The universal set of probes may be subdivided in many subsets which are spotted as unit arrays separated by barriers that prevent spreading of hybridization buffer with sample and labeled probe(s).

For detection of a nucleic acid species with a known sequence one of more oligonucleotide sequences comprising both unlabelled fixed and labeled probes in solution may be selected. Labeled probes are synthesized or selected from the presynthesized complete sets of, for example, 7-mers. The labeled probes are added to corresponding unit arrays of fixed probes such that a pair of fixed and labeled probes will adjacently hybridize to the target sequence such that upon administration of ligase the probes will be covalently bound.

If a unit array contains more than one fixed probe (as separated spots or within the same spot) that are positive in a given nucleic acid species all corresponding labeled probes may be mixed and added to the same unit array. The mixtures of labeled probes are even more important when mixtures of nucleic acid species are tested. One example of a complex mixture of nucleic acid species are mRNAs in one cell or tissue.

According to one embodiment of the invention unit arrays of fixed probes allow use of every possible immobilized probe with cocktails of a relatively small number of labeled probes. More complex cocktails of labeled probes may be used if a multiplex labeling scheme is implemented. Preferred multiplexing methods may use different fluorescent dyes or molecular tags that may be separated by mass spectroscopy.

Alternatively, according to a preferred embodiment of the invention, relatively short fixed probes may be selected which frequently hybridize to many nucleic acid sequences. Such short probes are used in combination with a cocktail of labeled probes which may be prepared such that at least one labeled probe corresponds to each of the fixed proves. Preferred cocktails are those in which none of the labeled probes corresponds to more than one fixed probe.

EXAMPLE 27

Interrogation of Segments of the HIV Virus with All Possible 10-mers

In this example of Format III SBH, an array was generated on nylon membranes (e.g., Gene Screen) of all possible bound 5-mers (1024 possible pentamers). The bound 5-mer oligonucleotides were synthesized with 5' tails of 5'-TTTTTT-NNN-3' (N=all four bases A, C, G, T, at this step in the synthesis equal molar amounts of all four bases are added). These oligonucleotides were precisely spotted onto the nylon membrane, the spots were allowed to dry, and the oligonucleotides were immobilized by treating the dried spots with UV light. Oligonucleotide densities of up to 18 oligonucleotides per square nanometer were obtained using this method. After the UV treatment, the nylon membranes were treated with a detergent containing buffer at 60–80° C. The spots of oligonucleotides were gridded in subarrays of 10 by 10 spots, and each subarray has 64 5-mer spots and 36 control spots. 16 subarrays give 1024 5-mers which encompasses all possible 5-mers.

The subarrays in the array were partitioned from each other by physical barriers, e.g., a hydrophobic strip, that allowed each subarray to be hybridized to a sample without cross-contamination from adjacent subarrays. In a preferred embodiment, the hydrophobic strip is made from a solution of silicone (e.g., household silicone glue and seal paste) in an appropriate solvent (such solvents are well known in the art). This solution of silicone grease is applied between the subarrays to form lines which after the solvent evaporates act as hydrophobic strips separating the cells.

In this Format III example, the free or solution (nonbound) 5-mers were synthesized with 3' tails of 5'-NN-3' (N=all four bases A, C, G, T). In this embodiment, the free 5-mers and the bound 5-mers are combined to produce all possible 10-mers for sequencing a known DNA sequence of less than 20 kb. 20 kb of double stranded DNA is denatured into 40 kb of single-stranded DNA. This 40 kb of ss DNA hybridizes to about 4% of all possible 10-mers. This low frequency of 10-mer binding and the known target sequence allow the pooling of free or solution (nonbound) 5-mers for treatment of each subarray, without a loss of sequence information. In a preferred embodiment, 16 probes are pooled for each subarray, and all possible 5-mers are represented in 64 total pools of free 5-mers. Thus, all possible 10-mers may be probed against a DNA sample using 1024 subarrays (16 subarrays for each pool of free 5-mers).

The target DNA in this embodiment represents two-600 bp segments of the HIV virus. These 600 bp segments are represented by pools of 60 overlapping 30-mers (the 30-mers overlap each adjacent 30 mer by 20 nucleotides). The pools of 30-mers mimic a target DNA that has been treated using techniques well known in the art to shear, digest, and/or random PCR the target DNA to produce a random pool of very small fragments.

As described above in the previous Format III examples, the free 5-mers are labeled with radioactive isotopes, biotin, fluorescent dyes, etc. The labeled free 5-mers are then hybridized along with the bound 5-mers to the target DNA, and ligated. In a preferred embodiment, 300–1000 units of ligase are added to the reaction. The hybridization conditions were worked out following the teachings of the previous examples. Following ligation and removal of the target DNA and excess free probe, the array is assayed to determine the location of labeled probes (using the techniques described in the examples above).

The known DNA sequence of the target, and the known free and bound 5-mers in each subarray, predict which bound 5-mers will be ligated to a labeled free 5-mer in each subarray. The signal from 20 of these predicted dots were lost and 20 new signals were gained for each change in the target DNA from the predicted sequence. The overlapping sequence of the bound 5-mers in these ten new dots identifies which free, labeled 5-mer is bound in each new dot.

Using the described methods, arrays and pools of free, labeled 5-mers, the test HIV DNA sequence was probed with all possible 10-mers. Using this Format III approach, we properly identified the "wild-type" sequence of the segments tested, as well as several sequence "mutants" that were introduced into these segments.

EXAMPLE 28

Sequencing of Repetitive DNA Sequences

In one embodiment, repetitive DNA sequences in the target DNA are sequenced with "spacer oligonucleotides" in a modified Format III approach. Spacer oligonucleotides of varying lengths of the repetitive DNA sequence (the repeating sequence is identified on a first SBH run) are hybridized to the target DNA along with a first known adjoining oligonucleotide and a second known, or group of possible oligonucleotides adjoining the other side of the spacer (known from the first SBH run). When a spacer matching the length of the repetitive DNA segment is hybridized to the target, the two adjacent oligonucleotides can be ligated to the spacer. If the first known oligonucleotide is fixed to a substrate, and the second known or possible oligonucleotide(s) is labeled, a bound ligation product including the labeled second known or possible oligonucleotide(s) is formed when a spacer of the proper length is hybridized to the target DNA.

EXAMPLE 29

Sequencing Through Branch Points with Format III SBH

In one embodiment, branch points in the target DNA are sequenced using a third set of oligonucleotides and a modified Format III approach. After a first SBH run, several branch points may be identified when the sequence is compiled. These can be solved by hybridizing oligonucleotide(s) that overlap partially with one of the known sequences leading into the branch point and then hybridizing to the target an additional oligonucleotide that is labeled and corresponds to one of the sequences that comes out of the branch point. When the proper oligonucleotides are hybridized to the target DNA, the labeled oligonucleotide can be ligated to the other(s). In a preferred embodiment, a first oligonucleotide that is offset by one to several nucleotides from the branch point is selected (so that it reads into one of the branch sequences), a second oligonucleotide reading from the first and into the branch point sequence is also selected, and a set of third oligonucleotides that correspond to all the possible branch sequences with an overlap of the branch point sequence by one or a few nucleotides (corresponding to the first oligonucleotide) is selected. These oligonucleotides are hybridized to the target DNA, and only the third oligonucleotide with the proper branch sequence (that matches the branch sequence of the first oligonucleotide) will produce a ligation product with the first and second oligonucleotides.

EXAMPLE 30

Multiplexing Probes for Analyzing a Target Nucleic Acid

In this Example, sets of probes are labeled with different labels so that each probe of a set can be differentiated from the other probes in the set. Thus, the set of probes may be contacted with target nucleic acid in a single hybridization reaction without the loss of any probe information. In preferred embodiments, the different labels are different radioisotopes, or different flourescent labels, or different EMLs. These sets of probes may be used in either Format I, Format II or Format III SBH.

In Format I SBH, the set of differently lableled probes are hybridized to target nucleic acid which is fixed to a substrate under conditions that allow differentiation between perfect matches one base-pair mismatches. Specific probes which bind to the target nucleic acid are identified by their different labels and perfect matches are determined, at least in part, from this binding information.

In Format II SBH, the target nucleic acids are labeled with different probes and hybridized to arrays of probes. Specific target nucleic acids which bind to the probes are identified by their different labels and perfect matches are determined, at least in part, form this binding information.

In Format III SBH, the set of differently labeled probes and fixed probes are hybridized to a target nucleic acid under conditions that allow perfect matches to be differentiated from one base-pair mismatches. Labeled probes that are adjacent, on the target, to a fixed probe are bound to the fixed probe, and these products are detected and differentiated by their different labels.

In a preferred embodiment, the different labels are EMLs, which can be detected by electron capture mass spectrometry (EC-MS). EMLs may be prepared from a variety of backbone molecules, with certain aromatic backbones being particularly preferred, e.g., see Xu et al., J. Chromatog. 764:95–102 (1997). The EML is attached to a probe in a reversible and stable manner, and after the probe is hybridized to target nucleic acid, the EML is removed from the probe and identified by standard EC-MS (e.g., the EC-MS may be done by a gas chromotograph-mass spectrometer).

EXAMPLE 31

Detection of Low Frequency Target Nucleic Acids

Format III SBH has sufficient discrimination power to identify a sequence that is present in a sample at 1 part to 99 parts of a similar sequence that differs by a single nucleotide. Thus, Format III can be used to identify a nucleic acid present at a very low concentration in a sample of nucleic acids, e.g., a sample derived from blood.

In one embodiment, the two sequences are for cystic fibrosis and the sequences differ from each other by a deletion of three nucleotides. Probes for the two sequences were as follows, probes distinguishing the deletion from wild type were fixed to a substrate, and a labeled contiguous probe was common to both. Using these targets and probes, the deletion mutant could be detected with Format III SBH when it was present at one part to ninety nine parts of the wild-type.

EXAMPLE 32

Polaroid Apparatus and Method for Analyzing a Target Nucleic Acid

An apparatus for analyzing a nucleic acid can be constructed with two arrays of nucleic acids, and an optional material that prevents the nucleic acids of the two arrays from mixing until such mixing is desired. The arrays of the apparatus may be supported by a variety of substrates, including but not limited to, nylon membranes, nitrocellulose membranes, or other materials disclosed above. In preferred embodiments, one of the substrate is a membrane separated into sectors by hydrophobic strips, or a suitable support material with wells which may contain a gel or sponge. In this embodiment, probes are placed on a sector of the membrane, or in the well, the gel, or sponge, and a solution (with or without target nucleic acids) is added to the membrane or well so that the probes are solubilized. The solution with the solubilized probes is then allowed to contact the second array of nucleic acids. The nucleic acids may be, but are not limited to, oligonucleotide probes, or target nucleic acids, and the probes or target nucleic acids may be labeled. The nucleic acids may be labeled with any labels conventionally used in the art, including but not limited to radioisotopes, flourscent labels or electrophore mass labels.

The material which prevents mixing of the nucleic acids may be disposed between the two arrays in such a way that when the material is removed the nucleic acids of the two arrays mix together. This material may be in the form of a sheet, membrane, or other barrier, and this material may be comprised of any material that prevents the mixing of the nucleic acids.

This apparatus may be used in Format I SBH as follows: a first array of the apparatus has target nucleic acids that are fixed to the substrate, and a second array of the apparatus has nucleic acid probes that are labeled and can be removed to interrogate the target nucleic acid of the first array. The two arrays are optionally separated by a sheet of material that prevents the probes from contacting the target nucleic acid, and when this sheet is removed the probes can interrogate the target. After appropriate incubation and (optionally) washing steps the array of targets may be "read" to determine which probes formed perfect matches with the target. This reading may be automated or can be done manually (e.g., by eye with an autoradiogram). In Format II SBH, the procedure followed would be similar to that described above except that the target is labeled and the probes are fixed.

Alternatively, the apparatus may be used in Format III SBH as follows: two arrays of nucleic acid probes are formed, the nucleic acid probes of either or both arrays may be labeled, and one of the arrays may be fixed to its substrate. The two arrays are separated by a sheet of material that prevents the probes from mixing. A Format II reaction is initiated by adding target nucleic acid and removing the sheet allowing the probes to mix with each other and the target. Probes which bind to adjacent sites on the target are bound together (e.g., by base-stacking interactions or by covalently joining the backbones), and the results are read to determine which probes bound to the target at adjacent sites. When one set of probes is fixed to the substrate, the fixed array can be read to determine which probes from the other array are bound together with the fixed probes. As with the above method, this reading may be automated (e.g., with an ELISA reader) or can be done manually (e.g., by eye with an autoradiogram).

EXAMPLE 33

Polynucleotides Encoding a Chemokine Receptor Obtained from a cDNA Library of Fetal Liver-Spleen A plurality of novel nucleic acids were obtained from the b²HFLS20W cDNA library prepared from human fetal liver-spleen tissue, as described in Bonaldo et al., Genome Res. 6:791–806 (1996), using standard pcr, SBH sequence signature analysis and Sanger sequencing techniques.

The inserts of the library were amplified with PCR using primers specific for vector sequences which flank the inserts. These samples were spotted onto nylon membranes and interrogated with oligonucleotide probes to give sequence signatures. The clones were clustered into groups of similar or identical sequences, and single representative clones were selected from each group for gel sequencing. The 5' sequence of the amplified inserts was then deduced using the reverse M13 sequencing primer in a typical Sanger sequencing protocol. PCR products were purified and subjected to flourescent dye terminator cycle sequencing. Single pass gel sequencing was done using a 377 Applied Biosystems (ABI) sequencer. One of these inserts was identified as a novel sequence not previously obtained from this library, and not previously reported in public databases. This sequence is shown in FIG. 1 as SEQ ID NO:1.

FIG. 1 also shows SEQ ID NO:2, which represents an extension of the original cDNA sequence, SEQ ID NO:1. This sequence was obtained, in the 3' direction, using additional gene specific primers based on SEQ ID NO:1 (256A: 5'-CAGCAGGTGCTGGCGTAGGCG-3' (SEQ ID NO: 20); 256B: 5'-GACTCTGGTGGAGCGAGAGCA-3' (SEQ ID NO:21)) as sequencing primers for Sanger dideoxy sequencing using the BigDYETm terminator (Perkin Elmer ABI) cycle sequencing reactions. In the 5' direction, additional sequence was obtained by a PCR-based method of extending 5' sequence information from truncated cDNAs. Briefly, using a PCR based approach with gene-specific primers based on SEQ ID NO:1 and the 3' extended sequence (256A16-3: 5'-GGGGAGACGTGACTCTGGTGG-3' (SEQ ID NO:22); 256A16-5: 5'-ACCTTGAGCTGCGTGTTTGGG-3' (SEQ ID NO:23)), a fetal liver cDNA library was found to contain a relatively high level number of clones corresponding to this sequence. Half a million clones of this library were then screened in a traditional colony lifting method (Sambrook, J. et al., "Molecular Cloning, A Laboratory Manual", Cold Spring Harbor Laboratory Press, 1989) by hybridization with a gene-specific probe. The probe was made using a random primer labeling reaction incorporating alpha $^{33}$P dCTP and using a PCR product as the template. The PCR product was generated by amplifying the clone RTA00000256.a.16, which contains SEQ ID NO:1 and the 3' extended sequence, with the gene specific primers 256A16-3 and 256A16-5.

Clones that hybridized to the probe were pooled and sequenced using a 5' RACE—(Rapid Amplification of cDNA Ends) type of amplification strategy (Frohman, M. A., Dush, M. K. and Martin, G. R., (1988) *Proc. Natl. Acad. Sci. USA* 85, 8998–9002). More specifically, bacterial cells with positive hybridization signals were resuspended and served as template for PCR reactions using a vector primer corresponding to a sequence 5' of the cloning site (PCD2: 5'-ATGAATTCTAATACGACTCACTATA-3' (SEQ ID NO: 24)) and a gene-specific primer (256A': 5'-CGCCTACGCCAGCACCTGCTG-3' (SEQ ID NO:25)). By sequencing the longest of the PCR products using PCD2 and 256A' as sequencing primers in the BigDYE terminator (Perkin Elmer ABI) cycle sequencing reactions, additional sequence information was obtained to extend the original cDNA sequence 5' to give SEQ ID NO:2, which is approximately 1.6 kb in length.

EXAMPLE 34

Expression Study Using SEQ ID NO:2

To study the role of SEQ ID NO:2, gene expression was analyzed using a semi-quantatative polymerase chain reaction-based technique. cDNA libraries were used as sources of expressed genes from tissues of interest (three leukocyte preparations [two stimulated and one unstimulated], heart, lung, spleen, two placenta preparations, testes, fetal liver, fetal liver spleen, adult liver, bone marrow, lymph node, and macrophages). Gene specific primers were used to amplify a portion of the SEQ ID NO:2 sequence (corresponding to bases 1148 to 1375, as numbered from the 5' end of SEQ ID NO:2) from the samples.

Amplified products were separated on an agarose gel, transferred and chemically linked to a nylon filter. The filter was then hybridized with a radioactively labeled ($^{33}$P alpha-dCTP) double-stranded probe generated from the full-length SEQ ID NO:2 sequence using a Klenow polymerase, random prime method. The filters were washed (high stringency) and used to expose a phosphorimaging screen for several hours. Bands indicated the presence of cDNA including SEQ ID NO:2 sequences in a specific library, and thus mRNA expression in the corresponding cell type or tissue.

SEQ ID NO:2 was expressed in a very limited set of human tissues. Of the 15 human tissues tested, macrophages, fetal-liver spleen, and fetal liver were the only samples that provided a significant signal, indicating that expression of SEQ ID NO:2 is tightly regulated.

EXAMPLE 35

Chromosomal Localization Study Using SEQ ID NO:2

Chromosome mapping technologies allow investigators to link genes to specific regions of chromosomes. Chromosomal mapping was performed with the Stanford G3 Radiation Hybrid Panel (Research Genetics). The panel was screened with gene-specific primers that generated a sequence tag site (STS), and the results of the PCR screening were submitted to the Stanford Radiation Hybrid mapping email server at the Stanford Human Genome Center (SHGC). The gene position on the radiation hybrid framework map was provided by linking the STS corresponding to SEQ ID NO:2 with the SHGC marker with best linkage.

The results indicated that SEQ ID NO:2 is located on the short arm of chromosome 7 at 7p22. The STS was linked to the marker SHGC-34866 with a LOD (log of the odds) score of 1000 and cR-1000 of -0.00, indicating that the STS was within 24 kb (kilobases) of this marker.

Gene family members are often linked to specific regions of chromosomes owing to intrachromosomal gene duplication events that give rise to multimember gene families during the process of evolution. The IL-8 related receptor gene (also known as GPR30) has been localized to chromosome 7p22.

The present invention is not to be limited in scope by the exemplified embodiments which are intended as illustrations of single aspects of the invention, and compositions and methods which are functionally equivalent are within the scope of the invention. Indeed, numerous modifications and variations in the practice of the invention are expected to occur to those skilled in the art upon consideration of the present preferred embodiments. Consequently, the only limitations which should be placed upon the scope of the invention are those which appear in the appended claims.

All references cited within the body of the instant specification are hereby incorporated by reference in their entirety.

What is claimed is:

1. An isolated polynucleotide comprising:

(a) a polynucleotide encoding the amino acid sequence of SEQ ID NO: 3;

(b) the complement of (a); or (c) the nucleotide sequence of SEQ ID NO: 2.

2. The isolated polynucleotide of claim 1 wherein said polynucleotide comprises a polynucleotide encoding a polypeptide comprising SEQ ID NO: 3.

3. The isolated polynucleotide of claim 2 wherein said polynucleotide comprises DNA.

4. The isolated polynucleotide of claim 3 wherein said polynucleotide is SEQ ID NO: 2.

5. A vector comprising the polynucleotide of claim 1.

6. A host cell comprising the vector of claim 5.

7. A process for producing a polypeptide comprising culturing the host cell of claim 6 under conditions that allow expression of the polypeptide encoded by said polynucleotide in said vector.

8. An isolated polynucleotide comprising the nucleotide sequence of SEQ ID NO: 2.

9. The full complement of the polynucleotide of claim 2 or 8.

* * * * *